United States Patent

Miyake et al.

[11] Patent Number: 4,792,550
[45] Date of Patent: Dec. 20, 1988

[54] 13-AZA-14-OXO-TXA₂ ANALOGUES

[75] Inventors: Hajimu Miyake, Osaka; Tadao Okegawa, Kyoto; Akiyoshi Kawasaki, Osaka, all of Japan

[73] Assignee: Ono Pharmaceutical Co., Ltd., Osaka, Japan

[21] Appl. No.: 743,548

[22] Filed: Jun. 11, 1985

[30] Foreign Application Priority Data

Jun. 12, 1984 [JP] Japan .................. 59-119000

[51] Int. Cl.⁴ .................. C07C 177/00; A61K 31/557
[52] U.S. Cl. .................. 514/419; 514/529; 514/538; 514/562; 514/563; 548/492; 560/17; 560/48; 560/116; 560/118; 562/427; 562/457; 562/498; 562/500
[58] Field of Search .................. 560/118, 120, 17, 48, 560/116; 562/500, 502, 427, 457, 498; 548/492; 514/419, 538, 529, 562, 563

[56] References Cited

U.S. PATENT DOCUMENTS 4,389,413 6/1983 Nobyuki .................. 514/469
4,628,061 12/1986 Jones .................. 514/469

FOREIGN PATENT DOCUMENTS 44711 1/1982 European Pat. Off. .......... 560/119

Primary Examiner—Robert Gerstl
Attorney, Agent, or Firm—Sughrue, Mion, Zinn, Macpeak & Seas

[57] ABSTRACT

A novel 13-aza-14-oxo-TXA₂ analogue of general formula:

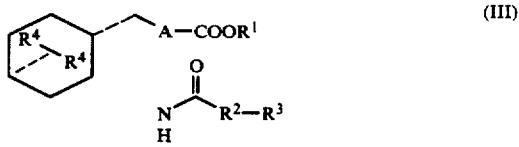

wherein symbol

A represents $-CH_2CH_2-(CH_2)_m-$, cis—$CH=CH-(CH_2)_m-$, $-CH_2O-(CH_2)_m-$, $-S-(CH_2)_m-$

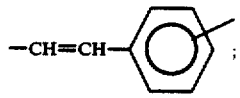

$R^2$ represents a bond or a straight or branched alkylene or alkenylene group of from 1 to 10 carbon atom(s) unsubstituted or substituted;

$R^3$ represents (i) a phenyl, phenoxy or phenylthio group unsubstituted or substituted, (ii) a straight or branched alkyl, alkenyl or alkynyl group of from 1 to 6 carbon atom(s) unsubstituted or substituted, (iii) a cycloalkyl, cycloalkyloxy or cycloalkylthio group of from 4 to 7 carbon atoms unsubstituted or substituted, (iv) a naphthyl, indolyl or indanyl group, or (v) an amino group unsubstituted or substituted $R^4$ represents a hydrogen atom or a methyl group.

87 Claims, No Drawings

13-AZA-14-OXO-TXA$_2$ ANALOGUES

SUMMARY

This invention is related to novel 13-aza-14-oxo-TXA$_2$ analogues.

More particularly, this invention is related to (1) novel 13-aza-14-oxo-TXA$_2$ analogues having an antagonistic activity on thromboxane A$_2$ (TXA$_2$);

(2) processes for the preparation of them; and (3) treating agent (including as use for prevention) for diseases induced by thromboxane A$_2$ containing them or it as active ingredient(s).

BACKGROUND

In 1975, Hamberg et al discovered an unstable intermediate in the conversion of prostaglandin G$_2$ into the hemiacetal derivative in platelets [Proc. Nat. Acad. Sci. U.S.A., Vol 72, No. 8 page 2994 (1975)]. The intermediates have been named as thromboxane A$_2$ and its structure has been proposed as follows:

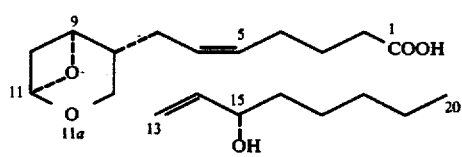

TXA$_2$ has been found to show various biological activities such as platelet aggregation, aorta contraction and thrombi formation and therefore is considered to be one of the cause by which diseases such as inflammation, thrombus and cardiac infarction are induced.

Some TXA$_2$ analogues are proposed as compounds having antagonistic activity on TXA$_2$; for example, compounds which replaced the oxygen atoms on 11a- and 9,11-epoxy-position of TXA$_2$ by carbon atoms [see Japanese Patent Kokai No. 55-143930], and compounds having pinane skelton [Proc. Nat. Acad. Sci. U.S.A. Vol. 76, No. 6, page 2566 (1979)].

Recently, Hamanaka et al have proposed a series of 13-aza-TXA$_2$ analogues which replaced the 13-position carbon atom by a nitrogen atom, [see Japanese Patent Kokai Nos. 57-108046, 57-24338, 58-13548 and 58-13551; i.e. European Patent No. 0044711 or U.S. Pat. No. 4,389,413.] of the general formula:

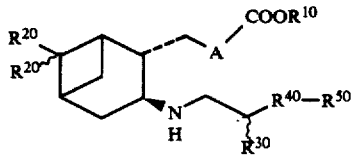

[wherein

A represents (i) —CH$_2$CH$_2$—(CH$_2$)$_m$—, (ii) cis—CH=CH—(CH$_2$)$_m$—, (iii) —CH$_2$—O—(CH$_2$)$_m$—, or

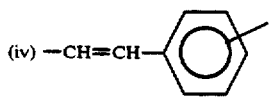

(wherein m represents an integer of from 1 to 6, double bond in the formula (iv) represents E, Z or EZ, and a phenylene group represents o-, m- or p-phenylene group.);

R$^{10}$ represents a hydrogen atom or a straight or branched alkyl group of from 1 to 12 carbon atom(s);

Each of R$^{20}$ represent hydrogen atoms or methyl groups;

R$^{30}$ represents a hydroxy group or a hydrogen atom;

R$^{40}$ represents a bond or a straight or branched alkylene group of from 1 to 5 carbon atom(s); and R$^{50}$ represents (i) an alkyl, alkoxy or alkylthio group of from 1 to 8 carbon atom(s), (ii) a cycloalkyl or cycloalkyloxy group of from 4 to 7 carbon atoms unsubstituted or substituted by at least one of straight or branched alkyl group of from 1 to 8 carbon atom(s), or (iii) a group of general formula:

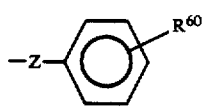

(wherein Z represents a bond, a oxygen atom or sulphur atom, and R$^{60}$ represents a hydrogen atom, a halogen atom, a hydroxy group, a straight or branched alkyl or alkoxy group of from 1 to 5 carbon atom(s), a triharomethyl, an amino group or a monoalkylamino or dialkylamino group of from 1 to 5 carbon atom(s));

And the wavy line (~) attached to 15-position carbon atom represents α- or β-configuration (i.e. S- or R-configuration), or mixture (i.e. RS) thereof.

With proviso that, R$^{50}$ should not be an alkoxy, alkylthio, cycloalkyloxy or cycloalkylthio group, when R$^{30}$ represent a hydroxy group and R$^4$ represents a bond.]

DISCLOSURE OF THE INVENTION

The present inventors have successed to synthesize novel thromboxane analogues, which are compounds introduced a modification to purge their "amino-acid structure (i.e. the structure means one wherein a carboxylic acid and amino group exist in one molecule.)" on 13-azathromboxane analogues, i.e. the replacement of secondary amine on 13-position thereof by an amide.

The compounds of the present invention (13,14-amide compounds) are unexpected ones which have novel chemical structure.

In addition, it have been confirmed that in comparision with 13-azathromboxane analogues, the compounds of the present invention have been largely improved demerits of 13-azathromboxane analogues about pharmaceutical formulation, (e.g. solubility) and have equivalent antagonistic activity on TXA$_2$, and then the present inventors have achieved the present invention.

Chemical Structure

Accordingly, the present invention resides in novel 13-aza-14-oxothromboxane analogues of the general formula:

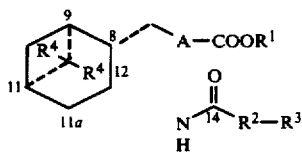

(III)

[wherein symbol

A represents
  (i) a group of general formula: —CH$_2$CH$_2$—(CH$_2$)$_m$—,
  (ii) a group of general formula: cis—CH=CH—(CH$_2$)$_m$—,
  (iii) a group of general formula: —CH$_2$O—(CH$_2$)$_m$—,
  (iv) a group of general formula: —S—(CH$_2$)$_m$— (wherein m represents an integer of from 1 to 6.) or
  (v) a group of general formula:

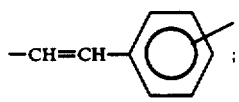

R$^1$ represents a hydrogen atom or a straight or branched alkyl group of from 1 to 12 carbon atom(s);

R$^2$ represents a bond or a straight or branched alkylene or alkenylene group of from 1 to 10 carbon atom(s) unsubstituted or substituted by at least one of hydroxy group, amino group, halogen atom or phenylthio group;

R$^3$ represents
  (i) a phenyl, phenoxy or phenylthio group unsubstituted or substituted by at least one of straight or branched alkyl or alkoxy group of from 1 to 6 carbon atom(s), halogen atom or hydroxy group,
  (ii) a straight or branched alkyl, alkenyl or alkynyl group of from 1 to 6 carbon atom(s) unsubstituted or substituted by at least one of halogen atom or hydroxy group,
  (iii) a cycloalkyl, cycloalkyloxy or cycloalkylthio group of from 4 to 7 carbon atoms unsubstituted or substituted by at least one of straight or branched alkyl group of from 1 to 6 carbon atom(s), halogen atom or hydroxy group,
  (iv) a naphthyl, indolyl or indanyl group, or
  (v) an amino group unsubstituted or substituted by at least one of straight or branched alkyl group of from 1 to 6 carbon atom(s); and R$^4$ represents a hydrogen atom or a methyl group.

With proviso that, the carbon atom neighbored with R$^3$ in R$^2$ should have no substituents, when R$^3$ represents a phenyloxy, phenylthio, cycloalkyloxy or cycloalkylthio group unsubstituted or substituted.]

and cyclodextrin clathrates thereof, and non-toxic salts thereof when R$^1$ represents a hydrogen atom; and processes for the preparation of them; and treating agent (including as use for prevention) diseases induced by thromboxane A$_2$ which contains them or it as active ingredient.

The indication of the formula (III) is natural form; nevertheless the formula (III) include enantiomeric form thereof, and the mixture of enantiomeric and natural forms, as is obvious to those skilled in the art.

And, in the structual formula of the specification including the formula (III) of the present invention, isomers generated by the existence of stereo-configuration unlimited (e.g. asymmetric carbon double bond) are included in the formula (III) or corresponding formula, respectively.

In the general formula (III), examples of the group represented by the general formula: —(CH$_2$)$_m$— are methylene, ethylene, trimethylene, tetramethylene, pentamethylene and hexamethylene groups; and trimethylene and tetramethylene groups are preferable.

In the general formula (III), examples of the alkyl group of from 1 to 12 carbon atom(s) represented by R$^1$ are methyl, ethyl, propyl, butyl, pentyl, hexyl, heptyl, octyl, nonyl, decyl, undecyl and dodecyl groups and isomeric groups thereof; and preferable groups as R$^1$ are a hydrogen atom and alkyl groups from 1 to 4 carbon atom(s) i.e. methyl, ethyl, propyl, butyl, isobutyl, sec-butyl and tert-butyl groups; and most preferable groups as R$^1$ are a hydrogen atom and a methyl group.

In the general formula (III), examples of the straight or branched alkylene group unsubstituted of from 1 to 10 carbon atom(s) represented by R$^2$ are methylene, ethylene, trimethylene, tetramethylene, pentamethylene, hexamethylene, heptamethylene, octamethylene, nonamethylene and decamethylene groups and isomeric groups thereof; and preferable groups as R$^2$ are methylene, ethylene, trimethylene, tetramethylene, pentamethylene, 1-methylethylene, 2-methylethylene, 2-methyltrimethylene, 1-methyltetramethylene, 3-methyltrimethylene, 3-methyltetramethylene, 4-methyltetramethylene, 2,4-dimethyltetramethylene, 1,1-dimethylethylene, 1,1-dimethyltrimethylene, 1,1-dimethyltetramethylene, 1,1-dimethylpentamethylene and 2,2-dimethyltrimethylene groups.

In the general formula (III), preferable groups as R$^2$, of the straight or branched alkylene group of from 1 to 10 carbon atom(s) substituted by at least one of hydroxy group, amino group, halogen atom or phenylthio group are 1-hydroxymethylene, 1-hydroxyethylene, 1-hydroxytrimethylene, 1-hydroxytetramethylene, 1-hydroxypentamethylene, 1-hydroxy-2-methylethylene, 1-hydroxy-3-methyltrimethylene, 1-aminoethylene, 1-chloromethylene, 1-chloroethylene and 2-phenylthiotrimethylene groups.

In the general formula (III), examples of the straight or branched alkenylene group of from 2 to 10 carbon atoms represented by R$^2$ are vinylene, propenylene, butenylene, pentenylene, hexenylene, heptenylene, octenylene, nonenylene and decenylene groups and isomeric groups thereof; and preferable groups are 1-methylvinylene, 1-butenylene and 2-butenylene groups.

In the general formula (III), a single bond as R$^2$ is also preferable.

In the general formula (III), preferable groups as R$^3$, of (i) phenyl, phenoxy or phenylthio groups unsubstituted or substituted by at least one of straight or branched alkyl or alkoxy group of from 1 to 6 carbon atom(s), halogen atom or hydroxy group are phenyl, 4-methoxyphenyl, 4-methylphenyl, 4-propylphenyl, 4-butylphenyl, phenoxy, phenylthio, 3-chlorophenyl and 4-chlorophenyl groups.

In the general formula (III), preferable groups as R$^3$, of (ii) straight or branched alkyl, alkenyl or alkynyl groups of from 1 to 6 carbon atom(s) unsubstituted or substituted by at least one of halogen atom or hydroxy group are methyl, chloromethyl, 2-methyl-1-propenyl and 1-propynyl groups.

In the general formula (III), examples of cycloalkyl groups of from 4 to 7 carbon atoms in $R^3$, of (iii) are cyclobutyl, cyclopentyl, cyclohexyl and cycloheptyl groups; and, preferable groups as $R^3$, of (iii) cycloalkyl, cycloalkyloxy or cycloalkylthio groups of from 4 to 7 carbon atoms unsubstituted or substituted by at least one of straight or branched alkyl group of from 1 to 6 carbon atom(s), halogen atom or hydroxy group are cyclopentyl, cyclohexyl, 3-butylcyclopentyl, 3-propylcyclopentyl, 1-hydroxycyclopentyl, cyclopentyloxy and cyclopentylthio groups.

In the general formula (III), naphthyl, indolyl, indanyl, propylamino and butylamino group as $R^3$ are also preferable.

In the general formula (III), examples of halogen atoms are fluorine, chlorine, iodine and bromine atom; and preferable halogen atom is chlorine atom.

With the proviso that, the carbon atom neighboured with $R^3$ in $R^2$ should have no substituents, when $R^3$ represents a phenoxy, phenylthio, cycloalkyloxy or cycloalkylthio group unsubstituted or substituted.

Process for the Preparation of the Present Invention (1)

The present invention includes not only the compounds per se, cyclodextrin clathrates thereof, non-toxic salts thereof, usage and method for use, but also processes for the preparation of them.

According to the present invention, the compounds of the present invention of the general formula (III) may be prepared by reacting an amine of general formula:

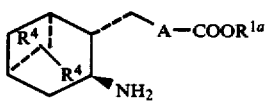 (IV)

[wherein $R^{1a}$ represents a straight or branched alkyl group of from 1 to 12 carbon atom(s), and the other symbols are as defined hereinbefore.]

and an acid of general formula:

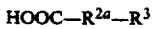

HOOC—$R^{2a}$—$R^3$ (V)

[wherein $R^{2a}$ represents a bond or a straight or branched alkylene or alkenylene group of from 1 to 10 carbon atom(s) unsubstituted or substituted by at least one of hydroxy group, benzyloxycarbonylamino group, halogen atom or phenylthio group. And the other symbols are as defined hereinbefore.]

or an isocyanate of general formula:

OCN—$R^5$ (VI)

[wherein $R^5$ represents a hydrogen atom or a straight or branched alkyl group of from 1 to 6 carbon atom(s).] to form amide (ureide) bond, and further, if desired, removing protecting group(s) i.e. benzyloxycarbonyl group, and/or subjecting a reaction of saponification.

Reactions to form amide-bond are well known, for example;

(A) by the method with using mixed acid anhydride
(B) by the method with using acid halide
(C) by the method with using DCC (dicyclohexylcarbodiimide) etc.

Concrete description of the methods described above are as follows:

(A) method with using mixed acid anhydride may be carried out, for example; an acid of the general formula (V) is reacted with an acid halide (pivaloyl chloride, tosyl chloride, mesyl chloride etc.) or an acid derivative (ethyl chloroformate, isobutyl chloroformate etc.) in an inert organic solvent (chloroform, methylene chloride, diethyl ether, THF etc.) in the presence of tertiary amine (pyridine, triethylamine, picoline etc.), at from 0° C. to 40° C. to give a mixed acid anhydride. The obtained acid mixed anhydride and an amine of the general formula (IV) are reacted in an inert organic solvent (described above), at from 0° C. to 40° C.

(B) method with using acid halide may be carried out, for example; an acid of the general formula (V) is reacted with an acid halide (thionyl chloride, oxalyl chloride etc.) in an inert organic solvent (described in above) or without solvents at from −20° C. to a refluxing temperature of the solvent used to give an acid halide. The obtained acid halide and an amine of the general formula (IV) are reacted in an inert organic solvent (described above) in the presence or absence of tertiary amine (described above) at from 0° C. to 40° C.

(C) method with using DCC may be carried out for example; an acid of the general formula (V) and an amine of the general formula (IV) are reacted in an inert organic solvent (described above) or without solvents in the presence or absence of tertiary amine (described above) using with DCC at from 0° C. to 40° C.

Preferably, the reactions (A), (B) and (C) described above are carried out in an atmosphere of inert gas (argon, nitrogen, etc.) on anhydrous condition.

The amine of the general formula (IV) may be prepared by saponification described hereafter, of an amide of general formula:

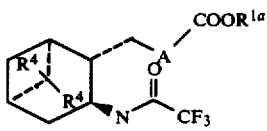 (VII)

[wherein all the symbols are as defined hereinbefore].

The amide of the general formula (VII) may be prepared by esterification described hereafter, of an acid of general formula:

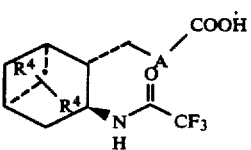 (VIII)

[wherein all the symbols are as defined hereinbefore].

Among the compounds of the general formula (VIII), compounds of general formula:

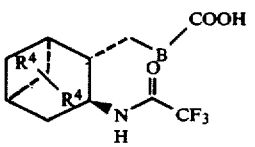 (VIIIa)

[wherein B represents a group of (i) the general formula —CH₂CH₂—(CH₂)$_m$—, (i) the general formula cis—CH=CH—(CH₂)$_m$— or (iii) the general formula

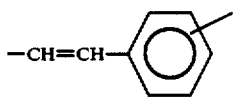

and the other symbols are as defined hereinbefore.] may be prepared by the series of reactions shown below in scheme [A].

Each symbol in the scheme [A] represents the following meaning respectively or as defined hereinbefore.

R⁶—tetrahydropyran-2-yl group, tetrahydrofuran-2-yl group or 1-ethoxyethyl group R⁷—phenyl group unsubstituted or substituted by straight or branched alkyl group of from 1 to 4 carbon atom(s) or an alkyl or alkoxy group of from 1 to 6 carbon atom(s)

T¹—p-toluenesulphonyl group or methanesulphonyl group

D—a group of general formula: —(CH₂)$_m$— or general formula:

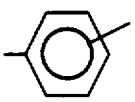

X¹—a halogen atom

B¹—a group of (i) general formula: cis—CH=CH—(CH₂)$_m$—, or (ii) general formula:

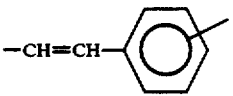

B²—a group of general formula: —CH₂—CH₂—(CH₂)$_m$—

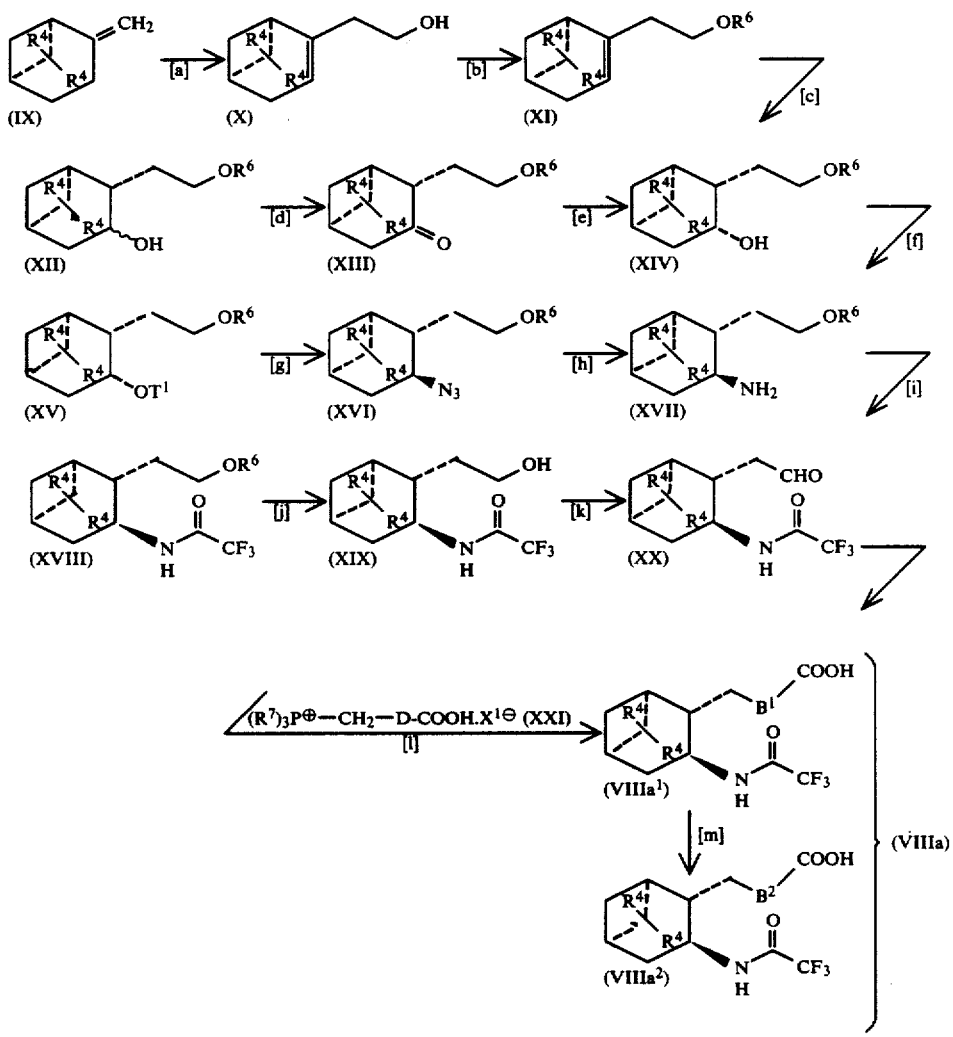

In the scheme [A], each step can be effected using methods known per se. Summarized descriptions are below:

Step [a] is additional reaction, and may be carried out, for example, the compound of the general formula (IX) is heated with paraformaldehyde in an sealed tube.

Step [b] is a reaction to induce a protecting group or hydroxy group, and may be carried out, for example, using with 2,3-dihydropyran, 2,3-dihydrofuran or ethyl vinyl ether, in an inert organic solvent (methylene chloride etc.) in the presence of a condensing agent (acid, e.g. p-toluenesulphonic acid).

Step [c] is hydroboration, and may be carried out, for example, using with diborane and hydroperoxide in a suitable inert organic solvent (tetrahydrofuran etc.) in alkaline condition.

Step [d] is oxidation, and may be carried out, for example, using a method of Jones oxidation with chromic acid, Collins oxidation or Swern oxidation, etc.

Step [e] is reduction, and may be carried out, for example, using with sodium borohydride in an alkanol.

Step [f] is tosylation or mesylation of hydroxy group, and may be carried out, for example, using with p-toluenesulphonyl chloride or methanesulphonyl chloride in a suitable inert organic solvent (methylene chloride etc.), in the presence of tertiary amine (triethylamine etc.).

Step [g] is azidation, and may be carried out, for example, using with sodium azide, in a suitable organic solvent (HMPA etc.) with heating.

Step [h] is reduction, and may be carried out, for example, using with a reducing agent (lithium aluminium hydride etc.) in an ether with heating.

Step [i] is a reaction to induce a protecting group on amine group (e.g. into trifluoroacetyl group) and may be carried out, for example, using the trifluoroacetic anhydride in a suitable inert organic solvent (methylene chloride etc.), in the presence of tertiary amine (pyridine etc.).

Step [j] is a reaction to remove a protecting group on hydroxy group, and may be carried out, for example, using with an acid (p-toluenesulphonic acid, acetic acid etc.) in a solvent (methanol, water etc.).

Step [k] is oxidation, and may be carried out, for example, using an oxidizing agent (oxalyl chloride, sulphuric anhydride-pyridine complex etc.) in a suitable organic solvent (DMSO etc.).

Step [l] is Wittig reaction, and may be carried out, for example, an aldehyde of the general formula (XX) is reacted with a Wittig reagent of the general formula (XXI) in a suitable organic solvent (DMSO, diethyl ether, toluene etc.) at from −50° C. to 80° C.

Step [m] is reduction, and may be carried out, for example, using hydrogen gas in an alkanol, in the presence of hydrogenation catalyst (palladium-carbon, nickel etc.).

The compounds of the general formula (XVII) may also be prepared from the compounds of the general formula (XIII) by oximizing, followed by reduction.

Oximation may be carried out, for example, using with hydroxylamine hydrochloride etc. in an organic solvent (methanol etc.), in the presence of an alkali (sodium carbonate, potassium carbonate, barium carbonate etc.) with refluxing.

Reduction may be carried out, for example, using with a catalyst (nickel etc.) in an atmosphere of hydrogen, in an organic solvent (methanol etc.); using with lithium aluminium hydride in an organic solvent (diethyl ether etc.); or using with metal sodium in an alcohol (propyl alcohol etc.) with refluxing.

Among the compounds of the general formula (VIII), compounds of general formula:

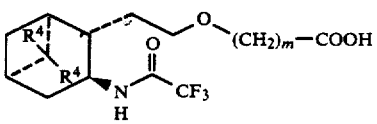

(VIIIb)

[wherein all the symbols are as defined hereinbefore.]

may be prepared by oxidating a compound of general formula:

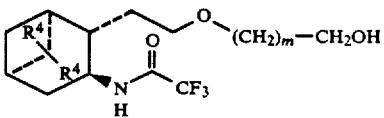

(XXII)

[wherein all the symbols are as defined hereinbefore.]

Oxidation may be carried out, for example, using the same method as step [d] in the scheme [A].

The compounds of the general formula (XXII) may be prepared by the same reactions as steps of from [c] to [j] using with a compound of general formula:

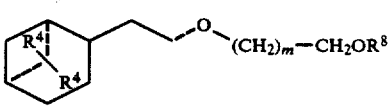

(XXIII)

[wherein $R^8$ represents tetrahydropyran-2-yl group, tetrahydrofuran-2-yl group or 1-ethoxyethyl group, and the other symbols are as defined hereinbefore.]

instead of the compound of the general formula (XI) in the [A].

The compounds of the general formula (XXIII) may be prepared by reacting a compound of the general formula (X) wwith a compound of general formula:

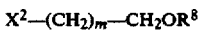

$X^2$—$(CH_2)_m$—$CH_2OR^8$ (XXIV)

[wherein $X^2$ represents a halogen atom, and the other symbols are as defined hereinbefore.]

The reaction is known per se, and may be carried out, for example, in the presence of a base (sodium hydride etc.) in a suitable organic solvent (DMSO etc.).

Among the compounds of the general formula (VIII), compounds of general formula:

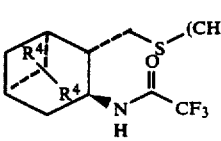

(VIIIc)

[wherein all the symbols are as defined hereinbefore.]

may be prepared by hydrolizing a compound of general formula:

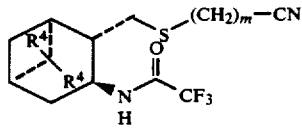 (XXV)

[wherein all the symbols are as defined hereinbefore.]

and further, inducing a protecting group on amino group (e.g. into trifluoroacetyl group), if desired.

Hydrolysis of cyano group into carboxy group is known reaction, and may be carried out, for example, using with a base (potassium hydroxide etc.) in an organic polar solvent which have high-boiling point (ethylene glycol etc.).

The reaction of inducing a protecting group into amino group may be carried out, for example, using the same method as step [i] in the scheme [A].

The compounds of the general formula (XXV) may be prepared by reacting a compound of general formula:

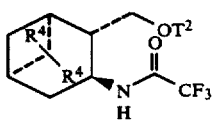 (XXVI)

[wherein $T^2$ represents p-toluenesulphonyl group or methanesulphonyl group, and the other symbols are as defined hereinbefore.]

with a compound of general formula:

HS—(CH$_2$)$_m$—CN  (XXVII)

[wherein all the symbols are as defined hereinbefore.]

The reaction is known per se, and may be carried out, for example, in the presence of a base (sodium hydride etc.) in a suitable organic solvent (DMSO, 1,2-dimethoxyethane etc.).

The compounds of the general formula (XXVI) may be prepared by tosylating or mesylating hydroxy group of a compound of general formula:

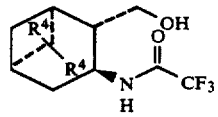 (XXVIII)

[wherein all the symbols are as defined hereinbefore.]

The reaction may be carried out, for example, using the same method as step [f] in the scheme [A].

The compound of the general formula (XXVIII) may be prepared by the same reactions as steps of from [b] to [j] using with a compound of general formula:

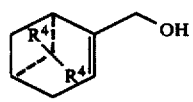 (XXIX)

[wherein all the symbols are as defined hereinbefore.]

instead of the compounds of the general formula (X).

Process for the Preparation of the Present Invention (2)

The compounds of the present invention of the general formula (III) may also be prepared by series of reactions in scheme [B] shown below, otherwise, by the process for the preparation (1) previously described.

Each symbols in the scheme [B] represents the following meaning respectively or as defined hereinbefore.

$R^{2b}$—a bond, a straight or branched alkylene or alkenylene group unsubstituted or substituted by at least one of protected hydroxy group (e.g. tetrahydropyran-2-yloxy group, tetrahydrofuran-2-yloxy group or 1-ethoxyethyl group), protected amino group (e.g. benzyloxycarbonylamino group), halogen atom or phenylthio group.

$R^9$—tetrahydropyran-2-yl group, tetrahydrofuran-2-yl group or 1-ethoxyethyl group.

Scheme [B]

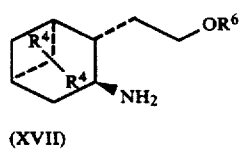 (XVII) → [n] → 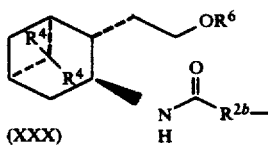 (XXX) → [o] →

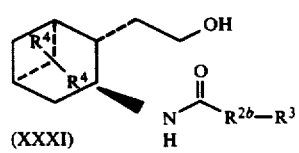 (XXXI) → [p] → 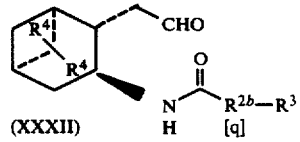 (XXXII) [q]

↓[s]  ↘[q]

-continued

Scheme [B]

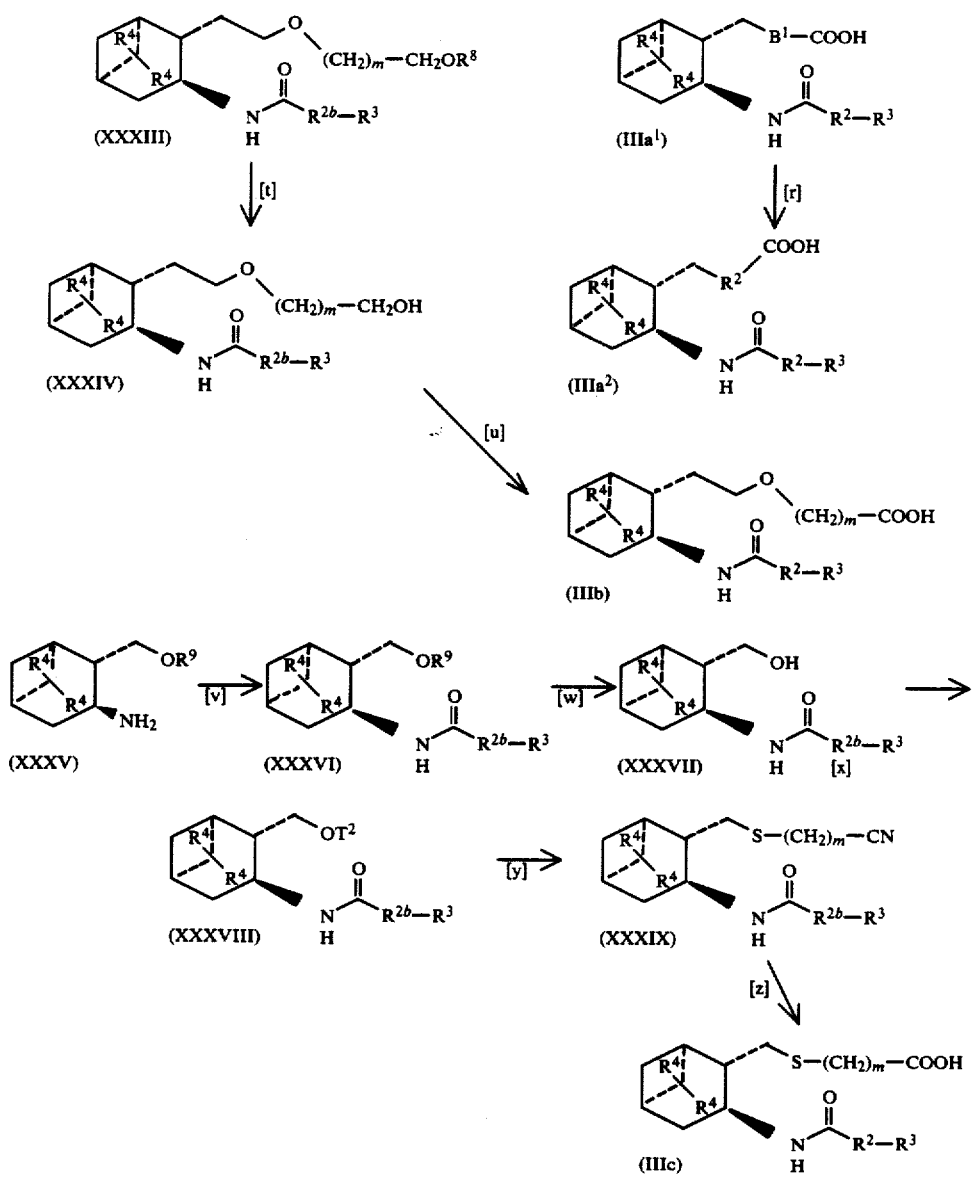

In the scheme [B], each step can be effected using methods known per se. Summarized descriptions are follows: Steps [n] and [v] are reactions to form amide-bonds respectively, and may be carried out, for example, using the same methods previously described to obtain the compounds of the general formula (III) from the compounds of the general formula (IV) and the compounds of the general formula (V), respectively.

Steps [o], [p], [q] and [r] may be carried out, for example, using the same methods as steps [j], [k], [l] and [m] in the scheme [A] previously described, respectively.

Step [s] is an additional reaction, and may be carried out, for example, using the same method to obtain the compounds of the general formula (XXIII) from the compounds of the general formula (X) and the compounds of the general formula (XXIV) previously described.

Steps [t] and [u] may be carried out, for example, using the same methods as steps [j] and [d] in the scheme [A] previously described, respectively.

Steps [w] and [x] may be carried out, for example, using the same methods as steps [j] and [f] in the scheme [A] previously described, respectively.

Step [y] and [z] may be carried out, for example, using the same method to obtain the compounds of the general formula (VIIIc) from the compounds of the general formula (XXVI) and the compounds of the general formula (XXVII) through the compounds of the general formula (XXV).

The Other Process for the Preparation of the Present Invention

The compounds of the general formula (III) of the present invention, wherein $R^1$ represents a straight or branched alkyl group of 1 to 12 carbon atom(s) (represented by $R^{1a}$) may be prepared by esterifying the compounds of the general formula (IIIa), (IIIb), (IIIc) or (IIId), previously described.

As a matter of course, a certain ester may be hydrolized to obtain corresponding acid or may be converted into another ester.

Conversion of a certain acid into a corresponding ester (i.e. esterification) is known reaction per se, and it may be carried out, for example;

(1) by the method using a diazoalkane
(2) by the method using an alkyl halide
(3) by the method using DMF-alkylacetal and
(4) by the method reacting with a corresponding alkanol Concrete descriptions of the reactions above mentioned are as follows:

(1) the method using a diazoalkane may be carried out, for example, in an inert organic solvent (diethyl ether, ethyl acetate, methylene chloride, acetone, methanol, ethanol etc.) using with corresponding diazoalkane.

(2) the method using an alkyl halide may be carried out, for example, in an organic solvent (acetone, N,N-dimethylformamide, DMSO etc.), in the presence of a base (potassium carbonate, sodium carbonate, sodium bicarbonate, potassium bicarbonate, calcium oxide etc.) using with a corresponding alkyl halide.

(3) the method using DMF-dialkylacetal may be carried out, for example, in an inert organic solvent (benzene, toluene etc.) using with a corresponding DMF-dialkylacetal.

(4) the method reacting with a corresponding alkanol may be carried out, for example, in a corresponding alkanol, using with an acid (hydrochloric acid, sulphuric acid, p-toluenesulphonic acid, hydrochloride etc.) or condensing agent (DCC, pivaloyl chloride, arylsulphonyl halide, alkylsulphonyl halide etc.).

Reactions mentioned above are carried out generally at from $-10°$ C. to $100°$ C.; and may be carried out further addition of inert organic solvent(s) (THF, methylene chloride etc.) not related to the reactions.

Conversion of a certain ester into corresponding acid (i.e. saponification) is known reaction per se, and it may be carried out, for example;

(1) using with an aqueous solution of an alkali (potassium hydroxide, sodium hydroxide, lithium hydroxide, potassium carbonate, sodium carbonate etc.) in a water-miscible organic solvent (THF, dioxane, ethanol, methanol etc.).

(2) using an alkali mentioned above, in an alkanol (methanol, ethanol etc.) in anhydrous condition.

The reactions above are carried out generally at from $-10°$ C. to $100°$ C.

In each reaction in the present specification, products may be purified by conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Starting Materials

Starting materials and reagents in the present invention are known compounds per se or may be prepared by known methods per se.

For example, a certain compound of the general formula (IX) wherein two $R^4$s are methyl groups is known as $\beta$-pinene; and a certain compound wherein two $R^4$s are hydrogen atoms may be prepared by the method described in J. Org. Chem., 28, 1128 (1963) from 2-oxonorpinane (described in Chem. Ber., 100, 3627 (1967)).

And, a certain compound of the general formula (XXIX) wherein two $R^4$s are methyl groups is known as myrtenol; and a certain compound of the general formula (XXIX) wherein two $R^4$s are hydrogen atoms may be prepared by reduction of 2-formyl-2-norpinene (described in J. Am. Chem. Soc., 102, 1404 (1980)).

And, Wittig reagents of the general formula (XXI), the halides of the general formula (XXIV), the thiols of the general formula (XXVII), the acids of the general formula (V) and the isocyanate of the general formula (VI) are also known compounds per se or may be prepared by known methods (e.g. method described in the specification of Japanese Patent Kokai No. 58-13548; i.e. European Patent No. 0044711 or U.S. Pat. No. 4,389,413).

And, the compounds of the general formula (XXXV) may be prepared by the series of reactions in the scheme [A] similar to the compounds of the general formula (XVII).

Cyclodextrin Clathrates and Salts

The cyclodextrin clathrates of 13-aza-14-oxo-TXA$_2$ analogues of the general formula (III) can be obtained by using $\alpha$-, $\beta$- or $\gamma$-cyclodextrin or a mixture thereof employing a method described in the specification of Japanese Patent Kokai Nos. 50-33620 or ibid 52-31404; i.e. British Patent Nos. 1,351,238 or 1,419,221.

By converting into cyclodextrin clathrates, the stability of 13-aza-14-oxo-TXA$_2$ analogues of the formula (III) can be increased.

The acids of the formula (III) wherein $R^1$ represents a hydrogen atom are converted into salts in known methods.

The salts are preferably non-toxic ones. The non-toxic salts herein referred mean salts of cations such that it is relatively innoxious to living body (animals including humans) tissues and that the effective pharmacological properties of the compound(s) of the general formula (III) are not impaired by side effect(s) resulting from the cations when used in an amount required for the treatment.

And water-soluble salts are preferable.

Suitable salts include, for example, a salt of an alkali metal (sodium, potassium etc.), a salt of an alkaline metal (calcium, magnesium etc.), an ammonium salt and a pharmaceutically acceptable (non-toxic) amine salt.

Amines suitable for forming such salts with carboxylic acid are well known, and include, for example, those amines which are theoretically obtained by substituting one or more of hydrogen atom(s) of ammonia by other groups.

Examples of such amine are, a sugar-amine (N-methylglucane, N-methylmannosamine, N-methylgalactosamine, N-methylfructosamine, N-methylarabinosamine, N-methylribsamine, N-methyllactosamine etc.) and another amine (ethanolamine, triethanolamine, triethylamine, meglumine etc.).

The salt can be obtained by known method per se, for example, by reacting an acid of the general formula (III) wherein $R^1$ represents a hydrogen atom with a suitable base (e.g. a hydroxide or carbonate of an alkali metal or an alkaline earth metal, ammonia or an amine) in theoretical amounts in an appropriate solvent.

The salt can be isolated by freeze-drying the solution, or by filtration if the salt is sufficiently insoluble to the reaction solution, or if necessary, by removing part of the solvent followed by filtation.

Pharmaceutical Activities

The compounds of the present invention of the general formula (III), cyclodextrin clathrates thereof, and non-toxic salts thereof possess an antagonistic activity on $TXA_2$, in particular, inhibit blood platelet aggregation and contraction of artery, and are, therefore, useful for prevention and/or treatment of inflammation, hypertension, thrombus, cerebral apoplexy, asthma, cardiac infarction, angina pectoris, cerebral infarction and death by acute cardiac diseases in mammals, in particular in humans which are induced by thromboxane $A_2$.

The compounds of the present invention of the general formula (III) possess antagonistic activity on $TXA_2$, in particular, inhibit blood platelet aggregation and contraction of artery.

In a standard laboratory test, for example, the compounds of the present invention of the general formula (III) showed the following pharmaceutical activities, in the below table I. In the table I, the following values are shown:

(i) concentrations required 50% inhibition ($IC_{50}$) on platelet aggregation using human blood induced by $STA_2$ (9,11-epithio-15-hydroxy-11a-carbathromb-5Z,13E-dienoic acid), and (ii) inhibitory percentages on contraction of artery induced by $STA_2$ in guinea pigs.

The methods employed in the test is described hereafter.

TABLE I

| Example No. of compounds | (i) concentrations required 50% inhibition on platelet aggregation ($IC_{50}$, $\mu M$) | (ii) Inhibitory ratios on contraction of artery (%) |
|---|---|---|
| 1(r) | 0.67 | 58.6 |
| 1(w) | 0.19 | 60.5 |
| 1(aa) | 0.29 | 66.4 |
| 3(c) | 0.43 | 78.1 |
| 3(g) | 0.63 | 60.5 |
| 1(dd) | 0.55 | 37.1 |
| 1(ee) | 0.38 | 39.0 |
| 1(hh) | 0.30 | 42.0 |
| 1(mm) | 0.26 | 48.8 |
| 2(j) | 0.56 | 27.3 |
| 6 | 0.67 | 78.1 |
| 1(o) | 0.56 | 34.2 |
| 2(g) | 0.42 | 39.0 |
| 1(cc) | 0.71 | — |
| 1(b) | 0.28 | 75.2 |
| 1(c) | 0.32 | 71.2 |
| 1(jj) | 0.30 | 46.8 |
| 1(kk) | 0.26 | 18.5 |
| 2(h) | 0.45 | 57.6 |
| 7(a) | 0.19 | 44.9 |
| 7(b) | 0.26 | 21.5 |

(i) Inhibitory activity on platelet aggregation induced by $STA_2$ in human blood and
(ii) Inhibitory activity on contraction of artery induced by $STA_2$ in guinea pig The experimental methods employed to measure each activity of the compound of the present invention are in the followings:

(i) Inhibitory activity of platelet aggregation induced by $STA_2$ in human blood Whole blood of healthy male human adult was collected with citric acid, and the mixture (20 ml) was centrifuged (180×g) for 10 min. The supernatant obtained was diluted with sufficient platelet poor plasma to obtain plasma which contains 300,000 platelet cells per $\mu l$.

A solution of tested compound in ethanol (1 $\mu l$) was added to the obtained plasma (250 $\mu l$), and then a solution of $STA_2$ in ethanol was added to the mixture. The measurement was carried out followed by the method of Born and then $IC_{50}$ was calculated.

(ii) Inhibitory activity of increasing of blood pressure

A glycine-sodium hydroxide buffer solution (pH 10) of tested compound was administered intravenously to a urethaneanaesthetized male guinea pig weighing 200–350 g, at a rate of 100 $\mu g/kg$ animal body weight via carotid vein.

And a solution of $STA_2$ in phosphate buffer (pH 7.4) was administered intravenously. Change of the blood pressure was measured at carotid artery and then inhibition ratio (%) was calculated.

Toxicity

On the other hand, it was conformed that the acute toxicity ($LD_{50}$) of all extent of the compounds of the present invention were more than 100 mg/Kg animal body weight by intravenous administration. Therefore, 13-aza-14-oxo-$TXA_2$ analogues of the present invention may be considered to be sufficiently safe and suitable for medical use. For example, the values of $LD_{50}$ of the compounds prepared in Example 10 and in Example 10(a) were 253 mg/Kg and 212 mg/Kg animal body weight by intravenous administration, in male mice, respectively.

Application for Pharmaceuticals

For the purpose hereinbefore described, the compounds of the present invention of the general formula (III), cyclodextrin clathrates thereof and non-toxic salts thereof may normally be administered systemically or partially; usually by oral or parenteral administration.

The doses to be administered is determined depending upon age, body weight, symptom, the desired therapeutic effect, the route of administration, and the duration of the treatment etc. In the human adult, the doses per person per dose are generally between 1 mg and 5 g, preferably between 10 mg and 500 mg, by oral administration, up to several times per day, and between 10 $\mu g$ and 1 g, preferably between 100 $\mu g$ and 100 mg, by parenteral administration up to several times per day.

As mentioned above, the doses to be used depend upon various conditions. Therefore, there are cases in which doses lower than or greater than the ranges specified above may be used.

Solid compositions according to the present invention for oral administration include compressed tablets, dispersible powders and granules. In such solid compositions, one or more of the active compound(s) is or are, admixed with at least one inert diluent such as lactose, mannitol, glucose, hydroxypropylcellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, disintegrating agents such as cellulose calcium gluconate, and assistant for dissolving e.g. arginine, glutamic acid or amino-acid such as aspartic acid. The tablets or pills may, if desired, be made into gastric film-coated or enteric film-coated tablets or pills, such as sugar-coated, gelatin-coated, hydroxypropylcellulose-coated or hydroxypropylmethyl cellulose phthalate-coated tablets or pills; two or more of layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise one or more of the active compound(s).

Preparations for injection according to the present invention for parenteral administration include sterile aqueous or non-aqueous solutions, suspensions or emulsions. Example of aqueous solvents or suspending media are distilled water for injection and physiological salt solution. Examples of non-aqueous solvents or suspending media are propylene glycol, polyethylene glycol, vegetable oils such as olive oil, alcohols such as ethanol, POLYSORBATE 80 (registered Trade Mark). These compositions may also include adjuvants such as preserving, wetting, emulsifying, dispersing agents and assistant agent for dissolving (e.g. arginine, glutamic acid or amino-acid such as aspartic acid). They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments, suppositories for rectal administration and pessaries for vaginal administration which comprise one or more of the active compound(s) and may be prepared by known methods.

Preferred Compounds

Among the compounds of the present invention represented by the general formula (III), preferred compounds are as follows:

(1) 9α,11α-dimethylmethano-13-aza-14-oxo-16-phenyl-17,18,19,20-tetranor-11a-carbathromb-5Z-enoic acid,
(2) 9α,11α-dimethylmethano-13-aza-14-oxo-16-(4-methylphenyl)-17,18,19,20-tetranor-11a-carbathromb-5Z-enoic acid,
(3) 9α,11α-dimethylmethano-13-aza-14-oxo-16-(4-propylphenyl)-17,18,19,20-tetranor-11a-carbathromb-5Z-enoic acid,
(4) 9α,11α-dimethylmethano-13-aza-14-oxo-16-(4-butylphenyl)-17,18,19,20-tetranor-11a-carbathromb-5Z-enoic acid,
(5) 9α,11α-dimethylmethano-13-aza-14-oxo-16-(4-methoxyphenyl)-17,18,19,20-tetranor-11a-carbathromb-5Z-enoic acid,
(6) 9α,11α-dimethylmethano-13-aza-14-oxo-16-(3-chlorophenyl)-17,18,19,20-tetranor-11a-carbathromb-5Z-enoic acid,
(7) 9α,11α-dimethylmethano-13-aza-14-oxo-17-phenyl-18,19,20-trinor-11a-carbathromb-5Z-enoic acid,
(8) 9α,11α-dimethylmethano-13-aza-14-oxo-17-(4-methylphenyl)-18,19,20-trinor-11a-carbathromb-5Z-enoic acid,
(9) 9α,11α-dimethylmethano-13-aza-14-oxo-17-(4-propylphenyl)-18,19,20-trinor-11a-carbathromb-5Z-enoic acid,
(10) 9α,11α-dimethylmethano-13-aza-14-oxo-17-(4-butylphenyl)-18,19,20-trinor-11a-carbathromb-5Z-enoic acid,
(11) 9α,11α-dimethylmethano-13-aza-14-oxo-17-(4-methoxyphenyl)-18,19,20-trinor-11a-carbathromb-5Z-enoic acid,
(12) 9α,11α-dimethylmethano-13-aza-14-oxo-17-(3-chlorophenyl)-18,19,20-trinor-11a-carbathromb-5Z-enoic acid,
(13) 9α,11α-dimethylmethano-13-aza-14-oxo-18-phenyl-19,20-dinor-11a-carbathromb-5Z-enoic acid,
(14) 9α,11α-dimethylmethano-13-aza-14-oxo-18-(4-methylphenyl)-19,20-dinor-11a-carbathromb-5Z-enoic acid,
(15) 9α,11α-dimethylmethano-13-aza-14-oxo-18-(4-propylphenyl)-19,20-dinor-11a-carbathromb-5Z-enoic acid,
(16) 9α,11α-dimethylmethano-13-aza-14-oxo-18-(4-butylphenyl)-19,20-dinor-11a-carbathromb-5Z-enoic acid,
(17) 9α,11α-dimethylmethano-13-aza-14-oxo-18-(4-methoxyphenyl)-19,20-dinor-11a-carbathromb-5Z-enoic acid,
(18) 9α,11α-dimethylmethano-13-aza-14-oxo-18-(4-chlorophenyl)-19,20-dinor-11a-carbathromb-5Z-enoic acid,
(19) 9α,11α-dimethylmethano-13-aza-14-oxo-15-methyl-16-phenyl-17,18,19,20-tetranor-11a-carbathromb-5Z-enoic acid,
(20) 9α,11α-dimethylmethano-13-aza-14-oxo-15-methyl-16-(4-methylphenyl)-17,18,19,20-tetranor-11a-carbathromb-5Z-enoic acid,
(21) 9α,11α-dimethylmethano-13-aza-14-oxo-15-methyl-16-(4-propylphenyl)-17,18,19,20-tetranor-11a-carbathromb-5Z-enoic acid,
(22) 9α,11α-dimethylmethano-13-aza-14-oxo-15-methyl-16-(4-butylphenyl)-17,18,19,20-tetranor-11a-carbathromb-5Z-enoic acid,
(23) 9α,11α-dimethylmethano-13-aza-14-oxo-15-methyl-16-(4-methoxyphenyl)-17,18,19,20-tetranor-11a-carbathromb-5Z-enoic acid,
(24) 9α,11α-dimethylmethano-13-aza-14-oxo-15-methyl-16-(3-chlorophenyl)-17,18,19,20-tetranor-11a-carbathromb-5Z-enoic acid,
(25) 9α,11α-dimethylmethano-13-aza-14-oxo-16-methyl-17-phenyl-18,19,20-trinor-11a-carbathromb-5Z-enoic acid,
(26) 9α,11α-dimethylmethano-13-aza-14-oxo-16-methyl-17-(4-methylphenyl)-18,19,20-trinor-11a-carbathromb-5Z-enoic acid,
(27) 9α,11α-dimethylmethano-13-aza-14-oxo-16-methyl-17-(4-propylphenyl)-18,19,20-trinor-11a-carbathromb-5Z-enoic acid,
(28) 9α,11α-dimethylmethano-13-aza-14-oxo-16-methyl-17-(4-butylphenyl)-18,19,20-trinor-11a-carbathromb-5Z-enoic acid,
(29) 9α,11α-dimethylmethano-13-aza-14-oxo-16-methyl-17-(4-methoxyphenyl)-18,19,20-trinor-11a-carbathromb-5Z-enoic acid,
(30) 9α,11α-dimethylmethano-13-aza-14-oxo-16-methyl-17-(3-chlorophenyl)-18,19,20-trinor-11a-carbathromb-5Z-enoic acid,

(31) 9α,11α-dimethylmethano-13-aza-14-oxo-16-methyl-18-phenyl-19,20-dinor-11a-carbathromb-5Z-enoic acid,

(32) 9α,11α-dimethylmethano-13-aza-14-oxo-16-methyl-18-(4-methylphenyl)-19,20-dinor-11a-carbathromb-5Z-enoic acid,

(33) 9α,11α-dimethylmethano-13-aza-14-oxo-16-methyl-18-(4-propylphenyl)-19,20-dinor-11a-carbathromb-5Z-enoic acid,

(34) 9α,11α-dimethylmethano-13-aza-14-oxo-16-methyl-18-(4-butylphenyl)-19,20-dinor-11a-carbathromb-5Z-enoic acid,

(35) 9α,11α-dimethylmethano-13-aza-14-oxo-16-methyl-18-(4-methoxyphenyl)-19,20-dinor-11a-carbathromb-5Z-enoic acid,

(36) 9α,11α-dimethylmethano-13-aza-14-oxo-16-methyl-18-(3-chlorophenyl)-19,20-dinor-11a-carbathromb-5Z-enoic acid,

(37) 9α,11α-dimethylmethano-13-aza-14-oxo-15,15-dimethyl-16-phenyl-17,18,19,20-tetranor-11a-carbathromb-5Z-enoic acid,

(38) 9α,11α-dimethylmethano-13-aza-14-oxo-15,15-dimethyl-16-(4-methylphenyl)-17,18,19,20-tetranor-11a-carbathromb-5Z-enoic acid,

(39) 9α,11α-dimethylmethano-13-aza-14-oxo-16-(4-propylphenyl)-17,18,19,20-tetranor-11a-carbathromb-5Z-enoic acid,

(40) 9α,11α-dimethylmethano-13-aza-14-oxo-16-(4-butylphenyl)-17,18,19,20-tetranor-11a-carbathromb-5Z-enoic acid,

(41) 9α,11α-dimethylmethano-13-aza-14-oxo-16-(4-methoxyphenyl)-17,18,19,20-tetranor-11a-carbathromb-5Z-enoic acid,

(42) 9α,11α-dimethylmethano-13-aza-14-oxo-16-(3-chlorophenyl)-17,18,19,20-tetranor-11a-carbathromb-5Z-enoic acid,

(43) 9α,11α-dimethylmethano-13-aza-14-oxo-15,15-dimethyl-17-phenyl-18,19,20-trinor-11a-carbathromb-5Z-enoic acid,

(44) 9α,11α-dimethylmethano-13-aza-14-oxo-15,15-dimethyl-17-(4-methylphenyl)-18,19,20-trinor-11a-carbathromb-5Z-enoic acid,

(45) 9α,11α-dimethylmethano-13-aza-14-oxo-15,15-dimethyl-17-(4-propylphenyl)-18,19,20-trinor-11a-carbathromb-5Z-enoic acid,

(46) 9α,11α-dimethylmethano-13-aza-14-oxo-15,15-dimethyl-17-(4-butylphenyl)-18,19,20-trinor-11a-carbathromb-5Z-enoic acid,

(47) 9α,11α-dimethylmethano-13-aza-14-oxo-15,15-dimethyl-17-(4-methoxyphenyl)-18,19,20-trinor-11a-carbathromb-5Z-enoic acid,

(48) 9α,11α-dimethylmethano-13-aza-14-oxo-15,15-dimethyl-17-(3-chlorophenyl)-18,19,20-trinor-11a-carbathromb-5Z-enoic acid,

(49) 9α,11α-dimethylmethano-13-aza-14-oxo-15,15-dimethyl-18-phenyl-19,20-dinor-11a-carbathromb-5Z-enoic acid,

(50) 9α,11α-dimethylmethano-13-aza-14-oxo-15,15-dimethyl-18-(4-methylphenyl)-19,20-dinor-11a-carbathromb-5Z-enoic acid,

(51) 9α,11α-dimethylmethano-13-aza-14-oxo-15,15-dimethyl-18-(4-propylphenyl)-19,20-dinor-11a-carbathromb-5Z-enoic acid,

(52) 9α,11α-dimethylmethano-13-aza-14-oxo-15,15-dimethyl-18-(4-butylphenyl)-19,20-dinor-11a-carbathromb-5Z-enoic acid,

(53) 9α,11α-dimethylmethano-13-aza-14-oxo-15,15-dimethyl-18-(4-methoxyphenyl)-19,20-dinor-11a-carbathromb-5Z-enoic acid,

(54) 9α,11α-dimethylmethano-13-aza-14-oxo-15,15-dimethyl-18-(3-chlorophenyl)-19,20-dinor-11a-carbathromb-5Z-enoic acid,

(55) 9α,11α-dimethylmethano-13-aza-14-oxo-15,15-dimethyl-19-phenyl-20-nor-11a-carbathromb-5Z-enoic acid,

(56) 9α,11α-dimethylmethano-13-aza-14-oxo-15,15-dimethyl-19-(4-methylphenyl)-20-nor-11a-carbathromb-5Z-enoic acid,

(57) 9α,11α-dimethylmethano-13-aza-14-oxo-15,15-dimethyl-19-(4-propylphenyl)-20-nor-11a-carbathromb-5Z-enoic acid,

(58) 9α,11α-dimethylmethano-13-aza-14-oxo-15,15-dimethyl-19-(4-butylphenyl)-20-nor-11a-carbathromb-5Z-enoic acid,

(59) 9α,11α-dimethylmethano-13-aza-14-oxo-15,15-dimethyl-19-(4-methoxyphenyl)-20-nor-11a-carbathromb-5Z-enoic acid,

(60) 9α,11α-dimethylmethano-13-aza-14-oxo-15,15-dimethyl-19-(3-chlorophenyl)-20-nor-11a-carbathromb-5Z-enoic acid,

(61) 9α,11α-dimethylmethano-13-aza-14-oxo-16,16-dimethyl-17-phenyl-18,19,20-trinor-11a-carbathromb-5Z-enoic acid,

(62) 9α,11α-dimethylmethano-13-aza-14-oxo-16,16-dimethyl-17-(4-methylphenyl)-18,19,20-trinor-11a-carbathromb-5Z-enoic acid,

(63) 9α,11α-dimethylmethano-13-aza-14-oxo-16,16-dimethyl-17-(4-propylphenyl)-18,19,20-trinor-11a-carbathromb-5Z-enoic acid,

(64) 9α,11α-dimethylmethano-13-aza-14-oxo-16,16-dimethyl-17-(4-butylphenyl)-18,19,20-trinor-11a-carbathromb-5Z-enoic acid,

(65) 9α,11α-dimethylmethano-13-aza-14-oxo-16,16-dimethyl-17-(4-methoxyphenyl)-18,19,20-trinor-11a-carbathromb-5Z-enoic acid,

(66) 9α,11α-dimethylmethano-13-aza-14-oxo-16,16-dimethyl-17-(3-chlorophenyl)-18,19,20-trinor-11a-carbathromb-5Z-enoic acid,

(67) 9α,11α-dimethylmethano-13-aza-14-oxo-15-methyl-16-phenyl-17,18,19,20-tetranor-11a-carbathromb-5Z,15E-dienoic acid,

(68) 9α,11α-dimethylmethano-13-aza-14-oxo-15-methyl-16-(4-methylphenyl)-17,18,19,20-tetranor-11a-carbathromb-5Z,15E-dienoic acid,

(69) 9α,11α-dimethylmethano-13-aza-14-oxo-15-methyl-16-(4-propylphenyl)-17,18,19,20-tetranor-11a-carbathromb-5Z,15E-dienoic acid,

(70) 9α,11α-dimethylmethano-13-aza-14-oxo-15-methyl-16-(4-butylphenyl)-17,18,19,20-tetranor-11a-carbathromb-5Z,15E-dienoic acid,

(71) 9α,11α-dimethylmethano-13-aza-14-oxo-15-methyl-16-(4-methoxyphenyl)-17,18,19,20-tetranor-11a-carbathromb-5Z,15E-dienoic acid,

(72) 9α,11α-dimethylmethano-13-aza-14-oxo-15-methyl-16-(3-chlorophenyl)-17,18,19,20-tetranor-11a-carbathromb-5Z,15E-dienoic acid,

(73) 9α,11α-dimethylmethano-13-aza-14-oxo-17-phenyl-18,19,20-trinor-11a-carbathromb-5Z,16E-dienoic acid,

(74) 9α,11α-dimethylmethano-13-aza-14-oxo-17-(4-methylphenyl)-18,19,20-trinor-11a-carbathromb-5Z,16E-dienoic acid,

(75) 9α,11α-dimethylmethano-13-aza-14-oxo-17-(4-propylphenyl)-18,19,20-trinor-11a-carbathromb-5Z,16E-dienoic acid,
(76) 9α,11α-dimethylmethano-13-aza-14-oxo-17-(4-butylphenyl)-18,19,20-trinor-11a-carbathromb-5Z,16E-dienoic acid,
(77) 9α,11α-dimethylmethano-13-aza-14-oxo-17-(4-methoxyphenyl)-18,19,20-trinor-11a-carbathromb-5Z,16E-dienoic acid,
(78) 9α,11α-dimethylmethano-13-aza-14-oxo-17-(3-chlorophenyl)-18,19,20-trinor-11a-carbathromb-5Z,16E-dienoic acid,
(79) 9α,11α-dimethylmethano-13-aza-14-oxo-15-phenoxy-16,17,18,19,20-pentanor-11a-carbathromb-5Z-enoic acid,
(80) 9α,11α-dimethylmethano-13-aza-14-oxo-15-(4-methylphenoxy)-16,17,18,19,20-pentanor-11a-carbathromb-5Z-enoic acid,
(81) 9α,11α-dimethylmethano-13-aza-14-oxo-15-(4-propylphenoxy)-16,17,18,19,20-pentanor-11a-carbathromb-5Z-enoic acid,
(82) 9α,11α-dimethylmethano-13-aza-14-oxo-15-(4-butylphenoxy)-16,17,18,19,20-pentanor-11a-carbathromb-5Z-enoic acid,
(83) 9α,11α-dimethylmethano-13-aza-14-oxo-15-(4-methoxyphenoxy)-16,17,18,19,20-pentanor-11a-carbathromb-5Z-enoic acid,
(84) 9α,11α-dimethylmethano-13-aza-14-oxo-15-(3-chlorophenoxy)-16,17,18,19,20-pentanor-11a-carbathromb-5Z-enoic acid,
(85) 9α,11α-dimethylmethano-13-aza-14-oxo-15-phenylthio-16,17,18,19,20-pentanor-11a-carbathromb-5Z-enoic acid,
(86) 9α,11α-dimethylmethano-13-aza-14-oxo-15-(4-methylphenylthio)-16,17,18,19,20-pentanor-11a-carbathromb-5Z-enoic acid,
(87) 9α,11α-dimethylmethano-13-aza-14-oxo-15-(4-propylphenylthio)-16,17,18,19,20-pentanor-11a-carbathromb-5Z-enoic acid,
(88) 9α,11α-dimethylmethano-13-aza-14-oxo-15-(4-butylphenylthio)-16,17,18,19,20-pentanor-11a-carbathromb-5Z-enoic acid,
(89) 9α,11α-dimethylmethano-13-aza-14-oxo-15-(4-methoxyphenylthio)-16,17,18,19,20-pentanor-11a-carbathromb-5Z-enoic acid,
(90) 9α,11α-dimethylmethano-13-aza-14-oxo-15-(3-chlorophenylthio)-16,17,18,19,20-pentanor-11a-carbathromb-5Z-enoic acid,
(91) 9α,11α-dimethylmethano-13-aza-14-oxo-16-phenylthio-17,18,19,20-tetranor-11a-carbathromb-5Z-enoic acid,
(92) 9α,11α-dimethylmethano-13-aza-14-oxo-16-(4-methylphenylthio)-17,18,19,20-tetranor-11a-carbathromb-5Z-enoic acid,
(93) 9α,11α-dimethylmethano-13-aza-14-oxo-16-(4-propylphenylthio)-17,18,19,20-tetranor-11a-carbathromb-5Z-enoic acid,
(94) 9α,11α-dimethylmethano-13-aza-14-oxo-16-(4-butylphenylthio)-17,18,19,20-tetranor-11a-carbathromb-5Z-enoic acid,
(95) 9α,11α-dimethylmethano-13-aza-14-oxo-16-(4-methoxyphenylthio)-17,18,19,20-tetranor-11a-carbathromb-5Z-enoic acid,
(96) 9α,11α-dimethylmethano-13-aza-14-oxo-16-(3-chlorophenylthio)-17,18,19,20-tetranor-11a-carbathromb-5Z-enoic acid,
(97) 9α,11α-dimethylmethano-13-aza-14-oxo-16,17,18,19,20-pentanor-11a-carbathromb-5Z-enoic acid,
(98) 9α,11α-dimethylmethano-13-aza-14-oxo-17,18,19,20-tetranor-11a-carbathromb-5Z-enoic acid,
(99) 9α,11α-dimethylmethano-13-aza-14-oxo-18,19,20-trinor-11a-carbathromb-5Z-enoic acid,
(100) 9α,11α-dimethylmethano-13-aza-14-oxo-19,20-dinor-11a-carbathromb-5Z-enoic acid,
(101) 9α,11α-dimethylmethano-13-aza-14-oxo-20-nor-11a-carbathromb-5Z-enoic acid,
(102) 9α,11α-dimethylmethano-13-aza-14-oxo-11a-carbathromb-5Z-enoic acid,
(103) 9Oα,11α-dimethylmethano-13-aza-14-oxo-20-methyl-11a-carbathromb-5Z-enoic acid,
(104) 9α,11α-dimethylmethano-13-aza-14-oxo-15-chloro-16,17,18,19,20-pentanor-11a-carbathromb-5Z-enoic acid,
(105) 9α,11α-dimethylmethano-13-aza-14-oxo-16-chloro-17,18,19,20-tetranor-11a-carbathromb-5Z-enoic acid,
(106) 9α,11α-dimethylmethano-13-aza-14-oxo-17-chloro-18,19,20-trinor-11a-carbathromb-5Z-enoic acid,
(107) 9α,11α-dimethylmethano-13-aza-14-oxo-18-chloro-19,20-dinor-11a-carbathromb-5Z-enoic acid,
(108) 9α,11α-dimethylmethano-13-aza-14-oxo-19-chloro-20-nor-11a-carbathromb-5Z-enoic acid,
(109) 9α,11α-dimethylmethano-13-aza-14-oxo-20-chloro-11a-carbathromb-5Z-enoic acid,
(110) 9α,11α-dimethylmethano-13-aza-14-oxo-15-methyl-17,18,19,20-tetranor-11a-carbathromb-5Z-enoic acid,
(111) 9α,11α-dimethylmethano-13-aza-14-oxo-16-methyl-18,19,20-trinor-11a-carbathromb-5Z-enoic acid,
(112) 9α,11α-dimethylmethano-13-aza-14-oxo-15-methyl-18,19,20-trinor-11a-carbathromb-5Z-enoic acid,
(113) 9α,11α-dimethylmethano-13-aza-14-oxo-17-methyl-19,20-dinor-11a-carbathromb-5Z-enoic acid,
(114) 9α,11α-dimethylmethano-13-aza-14-oxo-16-methyl-19,20-dinor-11a-carbathromb-5Z-enoic acid,
(115) 9α,11α-dimethylmethano-13-aza-14-oxo-15-methyl-19,20-dinor-11a-carbathromb-5Z-enoic acid,
(116) 9α,11α-dimethylmethano-13-aza-14-oxo-18-methyl-20-nor-11a-carbathromb-5Z-enoic acid,
(117) 9α,11α-dimethylmethano-13-aza-14-oxo-17-methyl-20-nor-11a-carbathromb-5Z-enoic acid,
(118) 9α,11α-dimethylmethano-13-aza-14-oxo-16-methyl-20-nor-11a-carbathromb-5Z-enoic acid,
(119) 9α,11α-dimethylmethano-13-aza-14-oxo-15-methyl-20-nor-11a-carbathromb-5Z-enoic acid,
(120) 9α,11α-dimethylmethano-13-aza-14-oxo-19-methyl-11a-carbathromb-5Z-enoic acid,
(121) 9α,11α-dimethylmethano-13-aza-14-oxo-18-methyl-11a-carbathromb-5Z-enoic acid,
(122) 9α,11α-dimethylmethano-13-aza-14-oxo-17-methyl-11a-carbathromb-5Z-enoic acid,
(123) 9α,11α-dimethylmethano-13-aza-14-oxo-16-methyl-11a-carbathromb-5Z-enoic acid,
(124) 9α,11α-dimethylmethano-13-aza-14-oxo-15-methyl-11a-carbathromb-5Z-enoic acid,
(125) 9α,11α-dimethylmethano-13-aza-14-oxo-15,16-dimethyl-18,19,20-trinor-11a-carbathromb-5Z-enoic acid,
(126) 9α,11α-dimethylmethano-13-aza-14-oxo-15,16-dimethyl-19,20-dinor-11a-carbathromb-5Z-enoic acid, (127) 9α,11α-dimethylmethano-13-aza-14-oxo-15,17-dimethyl-19,20-dinor-11a-carbathromb-5Z-enoic acid,
(128) 9α,11α-dimethylmethano-13-aza-14-oxo-16,17-dimethyl-19,20-dinor-11a-carbathromb-5Z-enoic acid,
(129) 9α,11α-dimethylmethano-13-aza-14-oxo-15,16-dimethyl-20-nor-11a-carbathromb-5Z-enoic acid,
(130) 9α,11α-dimethylmethano-13-aza-14-oxo-15,17-dimethyl-20-nor-11a-carbathromb-5Z-enoic acid,
(131) 9α,11α-dimethylmethano-13-aza-14-oxo-15,18-dimethyl-20-nor-11a-carbathromb-5Z-enoic acid,
(132) 9α,11α-dimethylmethano-13-aza-14-oxo-16,17-dimethyl-20-nor-11a-carbathromb-5Z-enoic acid,
(133) 9α,11α-dimethylmethano-13-aza-14-oxo-16,18-dimethyl-20-nor-11a-carbathromb-5Z-enoic acid,
(134) 9α,11α-dimethylmethano-13-aza-14-oxo-17,18-dimethyl-20-nor-11a-carbathromb-5Z-enoic acid,
(135) 9α,11α-dimethylmethano-13-aza-14-oxo-15,16-dimethyl-11a-carbathromb-5Z-enoic acid,
(136) 9α,11α-dimethylmethano-13-aza-14-oxo-15,17-dimethyl-11a-carbathromb-5Z-enoic acid,
(137) 9α,11α-dimethylmethano-13-aza-14-oxo-15,18-dimethyl-11a-carbathromb-5Z-enoic acid,
(138) 9α,11α-dimethylmethano-13-aza-14-oxo- 15,19-dimethyl-11a-carbathromb-5Z-enoic acid,
(139) 9α,11α-dimethylmethano-13-aza-14-oxo-16,17-dimethyl-11a-carbathromb-5Z-enoic acid,
(140) 9α,11α-dimethylmethano-13-aza-14-oxo-16,18-dimethyl-11a-carbathromb-5Z-enoic acid,
(141) 9α,11α-dimethylmethano-13-aza-14-oxo-16,19-dimethyl-11a-carbathromb-5Z-enoic acid,
(142) 9α,11α-dimethylmethano-13-aza-14-oxo-17,18-dimethyl-11a-carbathromb-5Z-enoic acid,
(143) 9α,11α-dimethylmethano-13-aza-14-oxo-17,19-dimethyl-11a-carbathromb-5Z-enoic acid,
(144) 9α,11α-dimethylmethano-13-aza-14-oxo-18,19-dimethyl-11a-carbathromb-5Z-enoic acid,
(145) 9α,11α-dimethylmethano-13-aza-14-oxo-15,15-dimethyl-18,19,20-trinor-11a-carbathromb-5Z-enoic acid,
(146) 9α,11α-dimethylmethano-13-aza-14-oxo-15,15-dimethyl-19,20-dinor-11a-carbathromb-5Z-enoic acid,
(147) 9α,11α-dimethylmethano-13-aza-14-oxo-16,16-dimethyl-19,20-dinor- 11a-carbathromb-5Z-enoic acid,
(148) 9α,11α-dimethylmethano-13-aza-14-oxo-15,15-dimethyl-20-nor-11a-carbathromb-5Z-enoic acid,
(149) 9α,11α-dimethylmethano-13-aza-14-oxo-16,16-dimethyl-20-nor-11a-carbathromb-5Z-enoic acid,
(150) 9α,11α-dimethylmethano-13-aza-14-oxo-17,17-dimethyl-20-nor-11a-carbathromb-5Z-enoic acid,
(151) 9α,11α-dimethylmethano-13-aza-14-oxo-15,15-dimethyl-11a-carbathromb-5Z-enoic acid,
(152) 9α,11α-dimethylmethano-13-aza-14-oxo-16,16-dimethyl-11a-carbathromb-5Z-enoic acid,
(153) 9α,11α-dimethylmethano-13-aza-14-oxo-17,17-dimethyl-11a-carbathromb-5Z-enoic acid,
(154) 9α,11α-dimethylmethano-13-aza-14-oxo-18,18-dimethyl-11a-carbathromb-5Z-enoic acid,
(155) 9α,11α-dimethylmethano-13-aza-14-oxo-15,15-dimethyl-20-nor-11a-carbathromb-5Z-en-17-ynoic acid,
(156) 9α,11α-dimethylmethano-13-aza-14-oxo-15,15-dimethyl-11a-carbathromb-5Z-en-17-ynoic acid,
(157) 9α,11α-dimethylmethano-13-aza-14-oxo-16,16-dimethyl-11a-carbathromb-5Z-en-17-ynoic acid,
(158) 9α,11α-dimethylmethano-13-aza-14-oxo-16,20,20-trimethyl-11a-carbathromb-5Z,19-dienoic acid,
(159) 9α,11α-dimethylmethano-13-aza-14-oxo-16,19-dimethyl-11a-carbathromb-5Z,18-dienoic acid,
(160) 9α,11α-dimethylmethano-13-aza-14-oxo-16,18-dimethyl-20-nor-11a-carbathromb-5Z,17-dienoic acid,
(161) 9α,11α-dimethylmethano-13-aza-14-oxo-14-cyclopentyl-15,16,17,18,19,20-hexanor-11a-carbathromb-5Z-enoic acid,
(162) 9α,11α-dimethylmethano-13-aza-14-oxo-14-(3-propylcyclopentyl)-15,16,17,18,19,20-hexanor-11a-carbathromb-5Z-enoic acid,
(163) 9α,11α-dimethylmethano-13-aza-14-oxo-14-(3-butylcyclopentyl)-15,16,17,18,19,20-hexanor-11a-carbathromb-5Z-enoic acid,
(164) 9α,11α-dimethylmethano-13-aza-14-oxo-15-cyclopentyl-16,17,18,19,20-pentanor-11a-carbathromb-5Z-enoic acid,
(165) 9α,11α-dimethylmethano-13-aza-14-oxo-15-(3-propylcyclopentyl)-16,17,18,19,20-pentanor-11a-carbathromb-5Z-enoic acid,
(166) 9α,11α-dimethylmethano-13-aza-14-oxo- 15-(3-butylcyclopentyl)-16,17,18,19,20-pentanor-11a-carbathromb-5Z-enoic acid,
(167) 9α,11α-dimethylmethano-13-aza-14-oxo-16-cyclopentyl-17,18,19,20-tetranor-11a-carbathromb-5Z-enoic acid,
(168) 9α,11α-dimethylmethano-13-aza-14-oxo-16-(3-propylcyclopentyl)-17,18,19,20-tetranor-11a-carbathromb-5Z-enoic acid,
(169) 9α,11α-dimethylmethano-13-aza-14-oxo-16-(3-butylcyclopentyl)-17,18,19,20-tetranor-11a-carbathromb-5Z-enoic acid,
(170) 9α,11α-dimethylmethano-13-aza-14-oxo-15-cyclopentylthio-16,17,18,99,20-pentanor-11a-carbathromb-5Z-enoic acid,
(171) 9α,11α-dimethylmethano-13-aza-14-oxo-15-(3-propylcyclopentylthio)-16,17,18,19,20-pentanor-11a-carbathromb-5Z-enoic acid,
(172) 9α,11α-dimethylmethano-13-aza-14-oxo-15-(3-butylcyclopentylthio)-16,17,18,19,20-pentanor-11a-carbathromb-5Z-enoic acid,
(173) 9α,11α-dimethylmethano-13-aza-14-oxo-16-cyclopentylthio-17,18,19,20-tetranor-11a-carbathromb-5Z-enoic acid,
(174) 9α,11α-dimethylmethano-13-aza-14-oxo-16-(3-propylcyclopentylthio)-17,18,19,20-tetranor-11a-carbathromb-5Z-enoic acid,
(175) 9α,11α-dimethylmethano-13-aza-14-oxo-16-(3-butylcyclopentylthio)-17,18,19,20-tetranor- 11a-carbathromb-5Z-enoic acid,
(176) 9α,11α-dimethylmethano-13-aza-14-oxo-17-cyclopentylthio-18,19,20-trinor-11a-carbathromb-5Z-enoic acid,
(177) 9α,11α-dimethylmethano-13-aza-14-oxo-17-(3-propylcyclopentylthio)-18,19,20-trinor-11a-carbathromb-5Z-enoic acid,
(178) 9α,11α-dimethylmethano-13-aza-14-oxo-17-(3-butylcyclopentylthio)-18,19,20-trinor-11a-carbathromb-5Z-enoic acid,
(179) 9α,11α-dimethylmethano-13-aza-14-oxo-15-cyclopentyloxy-16,17,18,19,20-pentanor-11a-carbathromb-5Z-enoic acid,
(180) 9α,11α-dimethylmethano-13-aza-14-oxo-15-(3-propylcyclopentyloxy)-16,17,18,19,20-pentanor-11a-carbathromb-5Z-enoic acid, (181) 9α,11α-dimethylmethano-13-aza-14-oxo-15-(3-butylcyclopentyloxy)-16,17,18,19,20-pentanor-11a-carbathromb-5Z-enoic acid, (182) 9α,11α-dimethylmethano-13-aza-14-oxo-16-cyclopentyloxy-16,17,18,19,20-pentanor-11a-carbathromb-5Z-enoic acid, (183) 9α,11α-dimethylmethano-13-aza-14-oxo-16-(3-propylcyclopentyloxy)-16,17,18,19,20-pentanor-11a-carbathromb-5Z-enoic acid, (184) 9α,11α-dimethylmethano-13-aza-14-oxo-16-(3-butylcyclopentyloxy)-16,17,18,19,20-pentanor-11a-carbathromb-5Z-enoic acid, (185) 9α,11α-dimethylmethano-13-aza-14-oxo-16-methyl-16-cyclopentyl-17,18,19,20-tetranor-11a-carbathromb-5Z-enoic acid, (186) 9α,11α-dimethylmethano-13-aza-14-oxo-16-methyl-16-(3-propylcyclopentyl)-17,18,19,20-tetranor-11a-carbathromb-5Z-enoic acid, (187) 9α,11α-dimethylmethano-13-aza-14-oxo-16-methyl-16-(3-butylcyclopentyl)-17,18,19,20-tetranor-11a-carbathromb-5Z-enoic acid, (188) 9α,11α-dimethylmethano-13-aza-14-oxo-17-methyl-17-cyclopentyl-18,19,20-trinor-11a-carbathromb-5Z-enoic acid, (189) 9α,11α-dimethylmethano-13-aza-14-oxo-17-methyl-17-(3-propylcyclopentyl)-18,19,20-trinor-11a-carbathromb-5Z-enoic acid, (190) 90α,11α-dimethylmethano-13-aza-14-oxo-17-methyl-17-(3-butylcyclopentyl)-18,19,20-trinor-11a-carbathromb-5Z-enoic acid, (191) 9α,11α-dimethylmethano-13-aza-14-oxo-16-methyl-17-cyclopentyl-18,19,20-trinor-11a-carbathromb-5Z-enoic acid, (192) 9α,11α-dimethylmethano-13-aza-14-oxo-16-methyl-17-(3-propylcyclopentyl)-18,19,20-trinor-11a-carbathromb-5Z-enoic acid, (193) 9α,11α-dimethylmethano-13-aza-14-oxo-16-methyl-17-(3-butylcyclopentyl)-18,19,20-trinor-11a-carbathromb-5Z-enoic acid, (194) 9α,11α-dimethylmethano-13-aza-14-oxo-14-(1-hydroxycyclopentyl)-15,16,17,18,19,20-pentanor-11a-carbathromb-5Z-enoic acid, (195) 9α,11α-dimethylmethano-13-aza-14-oxo-14-(1-hydroxy-3-propylcyclopentyl)-15,16,17,18,19,20-pentanor-11a-carbathromb-5Z-enoic acid, (196) 9α,11α-dimethylmethano-13-aza-14-oxo-14-(1-hydroxy-3-butylcyclopentyl)-15,16,17,18,19,20-pentanor-11a-carbathromb-5Z-enoic acid, (197) 9α,11α-dimethylmethano-13-aza-14-oxo-17-cyclopentyl-18,19,20-trinor-11a-carbathromb-5Z-enoic acid, (198) 9α,11α-dimethylmethano-13-aza-14-oxo-17-(3-propylcyclopentyl)-18,19,20-trinor-11a-carbathromb-5Z-enoic acid, (199) 9α,11α-dimethylmethano-13-aza-14-oxo-17-(3-butylcyclopentyl)-18,19,20-trinor-11a-carbathromb-5Z-enoic acid, (200) 9α,11α-dimethylmethano-13-aza-14-oxo-16-cyclopentyl-17,18,19,20-tetranor-11a-carbathromb-5Z-enoic acid, (201) 9α,11α-dimethylmethano-13-aza-14-oxo-16-(3-propylcyclopentyl)-17,18,19,20-tetranor-11a-carbathromb-5Z-enoic acid, (202) 9α,11α-dimethylmethano-13-aza-14-oxo-16-(3-butylcyclopentyl)-17,18,19,20-tetranor-11a-carbathromb-5Z-enoic acid, (203) 9α,11α-dimethylmethano-13-aza-14-oxo-15,15-dimethyl-16-cyclopentyl-17,18,19,20-tetranor-11a-carbathromb-5Z-enoic acid, (204) 9α,11α-dimethylmethano-13-aza-14-oxo-15,15-dimethyl-16-(3-propylcyclopentyl)-17,18,19,20-tetranor-11a-carbathromb-5Z-enoic acid, (205) 9α,11α-dimethylmethano-13-aza-14-oxo-15,15-dimethyl-16-(3-butylcyclopentyl)-17,18,19,20-tetranor-11a-carbathromb-5Z-enoic acid, (206) 9α,11α-dimethylmethano-13-aza-14-oxo-16,16-dimethyl-16-cyclopentyl-17,18,19,20-tetranor-11a-carbathromb-5Z-enoic acid, (207) 9α,11α-dimethylmethano-13-aza-14-oxo-16,16-dimethyl-16-(3-propylcyclopentyl)-17,18,19,20-tetranor-11a-carbathromb-5Z-enoic acid, (208) 9α,11α-dimethylmethano-13-aza-14-oxo-16,16-dimethyl-16-(3-butylcyclopentyl)-17,18,19,20-tetranor-11a-carbathromb-5Z-enoic acid, (209) 9α,11α-dimethylmethano-13-aza-14-oxo-16-cyclohexyl-17,18,19,20-tetranor-11a-carbathromb-5Z-enoic acid, (210) 9α,11α-dimethylmethano-13-aza-14-oxo-16-(4-propylcyclohexyl)-17,18,19,20-tetranor-11a-carbathromb-5Z-enoic acid, (211) 9α,11α-dimethylmethano-13-aza-14-oxo-16-(4-butylcyclohexyl)-17,18,19,20-tetranor-11a-carbathromb-5Z-enoic acid, (212) 9α,11α-dimethylmethano-13-aza-14-oxo-17-cyclohexyl-18,19,20-trinor-11a-carbathromb-5Z-enoic acid, (213) 9α,11α-dimethylmethano-13-aza-14-oxo-17-(4-propylcyclohexyl)-18,19,20-trinor-11a-carbathromb-5Z-enoic acid, (214) 9α,11α-dimethylmethano-13-aza-14-oxo-17-(4-butylcyclohexyl)-18,19,20-trinor-11a-carbathromb-5Z-enoic acid, (215) 9α,11α-dimethylmethano-13-aza-14-oxo-15-(2-naphthyl)-16,17,18,19,20-pentanor-11a-carbathromb-5Z-enoic acid, (216) 9α,11α-dimethylmethano-13-aza-14-oxo-16-(2-naphthyl)-17,18,19,20-tetranor-11a-carbathromb-5Z-enoic acid, (217) 9α,11α-dimethylmethano-13-aza-14-oxo-17-(2-naphthyl)-18,19,20-trinor-11a-carbathromb-5Z-enoic acid, (218) 9α,11α-dimethylmethano-13-aza-14-oxo-15-(3-indolyl)-16,17,18,19,20-pentanor-11a-carbathromb-5Z-enoic acid, (219) 9α,11α-dimethylmethano-13-aza-14-oxo-16-(3-indolyl)-17,18,19,20-tetranor-11a-carbathromb-5Z-enoic acid, (220) 9α,11α-dimethylmethano-13-aza-14-oxo-17-(3-indolyl)-88,19,20-trinor-11a-carbathromb-5Z-enoic acid, (221) 9α,11α-dimethylmethano-13-aza-14-oxo-15-(2-indanyl)-16,17,18,19,20-pentanor-11a-carbathromb-5Z-enoic acid, (222) 9α,11α-dimethylmethano-13-aza-14-oxo-16-(2-indanyl)-17,18,19,20-tetranor-11a-carbathromb-5Z-enoic acid, (223) 9α,11α-dimethylmethano-13-aza-14-oxo-17-(2-indanyl)-18,19,20-trinor-11a-carbathromb-5Z-enoic acid, (224) 9α,11α-dimethylmethano13,15-diaza-14-oxo-20-nor-11a-carbathromb-5Z-enoic acid, (225) 9α,11α-dimethylmethano-13,15-diaza-14-oxo-19,20-dinor-11a-carbathromb-5Z-enoic acid, (226) 9α,11α-dimethylmethano-13,15-diaza-14-oxo-18,19,20-trinor-11a-carbathromb-5Z-enoic acid,
(227) 9α,11α-dimethylmethano-13-aza-14-oxo-15-hydroxy-16-phenyl-17,18,19,20-tetranor-11a-carbathromb-5Z-enoic acid,
(228) 9α,11α-dimethylmethano-13-aza-14-oxo-15-hydroxy-16-(4-methylphenyl)-17,18,19,20-tetranor-11a-carbathromb-5Z-enoic acid,
(229) 9α,11α-dimethylmethano-13-aza-14-oxo-15-hydroxy-16-(4-propylphenyl)-17,18,19,20-tetranor-11a-carbathromb-5Z-enoic acid,
(230) 9α,11α-dimethylmethano-13-aza-14-oxo-15-hydroxy-16-(4-butylphenyl)-17,18,19,20-tetranor-11a-carbathromb-5Z-enoic acid,
(231) 9α,11α-dimethylmethano-13-aza-14-oxo-15-hydroxy-16-(4-methoxyphenyl)-17,18,19,20-tetranor-11a-carbathromb-5Z-enoic acid,
(232) 9α,11α-dimethylmethano-13-aza-14-oxo-15-hydroxy-16-(3-chlorophenyl)-17,18,19,20-tetranor-11a-carbathromb-5Z-enoic acid,
(233) 9α,11α-dimethylmethano-13-aza-14-oxo-15-hydroxy-17-phenyl-18,19,20-trinor-11a-carbathromb-5Z-enoic acid,
(234) 9α,11α-dimethylmethano-13-aza-14-oxo-15-hydroxy-17-(4-methylphenyl)-18,19,20-trinor-11a-carbathromb-5Z-enoic acid,
(235). 9α,11α-dimethylmethano-13-aza-14-oxo-15-hydroxy-17-(4-propylphenyl)-18,19,20-trinor-11a-carbathromb-5Z-enoic acid,
(236) 9α,11α-dimethylmethano-13-aza-14-oxo-15-hydroxy-17-(4-butylphenyl)-18,19,20-trinor-11a-carbathromb-5Z-enoic acid,
(237) 9α,11α-dimethylmethano-13-aza-14-oxo-15-hydroxy-17-(4-methoxyphenyl)-18,19,20-trinor-11a-carbathromb-5Z-enoic acid,
(238) 9α,11α-dimethylmethano-13-aza-14-oxo-15-hydroxy-17-(3-chlorophenyl)-18,19,20-trinor-11a-carbathromb-5Z-enoic acid,
(239) 9α,11α-dimethylmethano-13-aza-14-oxo-15-amino-16-phenyl-17,18,19,20-tetranor-11a-carbathromb-5Z-enoic acid,
(240) 9α,11α-dimethylmethano-13-aza-14-oxo-15-amino-16-(4-methylphenyl)-17,18,19,20-tetranor-11a-carbathromb-5Z-enoic acid,
(241) 9α,11α-dimethylmethano-13-aza-14-oxo-15-amino-16-(4-propylphenyl)-17,18,19,20-tetranor-11a-carbathromb-5Z-enoic acid,
(242) 9α,11α-dimethylmethano-13-aza-14-oxo-15-amino-16-(4-butylphenyl)-17,18,19,20-tetranor-11a-carbathromb-5Z-enoic acid,
(243) 9α,11α-dimethylmethano-13-aza-14-oxo-15-amino-16-(4-methoxyphenyl)-17,18,19,20-tetranor-11a-carbathromb-5Z-enoic acid,
(244) 9α,11α-dimethylmethano-13-aza-14-oxo-15-amino-16-(3-chlorophenyl)-17,18,19,20-tetranor-11a-carbathromb-5Z-enoic acid,
(245) 9α,11α-dimethylmethano-13-aza-14-oxo-15-hydroxy-17,18,19,20-tetranor-11a-carbathromb-5Z-enoic acid,
(246) 9α,11α-dimethylmethano-13-aza-14-oxo-15-hydroxy-18,19,20-trinor-11a-carbathromb-5Z-enoic acid,
(247) 9α,11α-dimethylmethano-13-aza-14-oxo-15-hydroxy-19,20-dinor-11a-carbathromb-5Z-enoic acid,
(248) 9α,11α-dimethylmethano-13-aza-14-oxo-15-hydroxy-20-nor-11a-carbathromb-5Z-enoic acid,
(249) 9α,11α-dimethylmethano-13-aza-14-oxo-15-hydroxy-11a-carbathromb-5Z-enoic acid,
(250) 9α,11α-dimethylmethano-13-aza-14-oxo-15-hydroxy-20-methyl-11a-carbathromb-5Z-enoic acid,
(251) 9α,11α-dimethylmethano-13-aza-14-oxo-15-hydroxy-16-methyl-18,19,20-trinor-11a-carbathromb-5Z-enoic acid,
(252) 9α,11α-dimethylmethano-13-aza-14-oxo-15-hydroxy-17-methyl-19,20-dinor-11a-carbathromb-5Z-enoic acid,
(253) 9α,11α-dimethylmethano-13-aza-14-oxo-15-hydroxy-18-methyl-20-nor-11a-carbathromb-5Z-enoic acid,
(254) 9α,11α-dimethylmethano-13-aza-14-oxo-15-hydroxy-19-methyl-11a-carbathromb-5Z-enoic acid,
(255) 9α,11α-dimethylmethano-13-aza-14-oxo-15-hydroxy-20,20-dimethyl-11a-carbathromb-5Z-enoic acid,
(256) 9α,11α-dimethylmethano-13-aza-14-oxo-15-hydroxy-16-methyl-19,20-dinor-11a-carbathromb-5Z-enoic acid,
(257) 9α,11α-dimethylmethano-13-aza-14-oxo-15-hydroxy-16-methyl-20-nor-11a-carbathromb-5Z-enoic acid,
(258) 9α,11α-dimethylmethano-13-aza-14-oxo-15-hydroxy-16-methyl-11a-carbathromb-5Z-enoic acid,
(259) 9α,11α-dimethylmethano-13-aza-14-oxo-15-hydroxy-16,20-dimethyl-11a-carbathromb-5Z-enoic acid,
(260) 9α,11α-dimethylmethano-13-aza-14-oxo-15-hydroxy-17-methyl-20-nor-11a-carbathromb-5Z-enoic acid,
(261) 9α,11α-dimethylmethano-13-aza-14-oxo-15-hydroxy-17-methyl-11a-carbathromb-5Z-enoic acid,
(262) 9α,11α-dimethylmethano-13-aza-14-oxo-15-hydroxy-17,20-dimethyl-11a-carbathromb-5Z-enoic acid,
(263) 9α,11α-dimethylmethano-13-aza-14-oxo-15-hydroxy-18-methyl-11a-carbathromb-5Z-enoic acid,
(264) 9α,11α-dimethylmethano-13-aza-14-oxo-15-hydroxy-18,20-dimethyl-11a-carbathromb-5Z-enoic acid,
(265) 9α,11α-dimethylmethano-13-aza-14-oxo-15-hydroxy-19,20-dimethyl-11a-carbathromb-5Z-enoic acid,
(266) 9α,11α-dimethylmethano-13-aza-14-oxo-15-hydroxy-15-cyclopentyl-16,17,18,19,20-pentanor-11a-carbathromb-5Z-enoic acid,
(267) 9α,11α-dimethylmethano-13-aza-14-oxo-15-hydroxy-15-(3-propylcyclopentyl)-16,17,18,19,20-pentanor-11a-carbathromb-5Z-enoic acid
(268) 9α,11α-dimethylmethano-13-aza-14-oxo-15-hydroxy-15-(3-butylcyclopentyl)-16,17,18,19,20-pentanor-11a-carbathromb-5Z-enoic acid,
(269) 9α,11α-dimethylmethano-13-aza-14-oxo-15-chloro-15-cyclopentyl-16,17,18,19,20-pentanor-11a-carbathromb-5Z-enoic acid,
(270) 9α,11α-dimethylmethano-13-aza-14-oxo- 15-chloro-15-(3-propylcyclopentyl)-16,17,18,19,20-pentanor-11a-carbathromb-5Z-enoic acid,
(271) 9α,11α-dimethylmethano-13-aza-14-oxo-15-chloro-15-(3-butylcyclopentyl)-16,17,18,19,20-pentanor-11a-carbathromb-5Z-enoic acid,
(272) 9α,11α-dimethylmethano-13-aza-14-oxo-15-phenylthio-15-cyclopentyl-16,17,18,19,20-pentanor-11a-carbathromb-5Z-enoic acid, (273) 9α,11α-dimethylmethano-13-aza-14-oxo-15-phenylthio-15-(3-propylcyclopentyl)-16,17,18,19,20-pentanor-11a-carbathromb-5Z-enoic acid, (274) 9α,11α-dimethylmethano-13-aza-14-oxo-15-phenylthio-15-(3-butylcyclopentyl)-16,17,18,19,20-pentanor-11a-carbathromb-5Z-enoic acid, (275) 9α,11α-dimethylmethano-13-aza-14-oxo-15-hydroxy-16-cyclopentyl-17,18,19,20-tetranor-11a-carbathromb-5Z-enoic acid, (276) 9α,11α-dimethylmethano-13-aza-14-oxo-15-hydroxy-16-(3-propylcyclopentyl)-17,18,19,20-tetranor-11a-carbathromb-5Z-enoic acid, (277) 9α,11α-dimethylmethano-13-aza-14-oxo-15-hydroxy-16-(3-butylcyclopentyl)-17,18,19,20-tetranor-11a-carbathromb-5Z-enoic acid, (278) 9α,11α-dimethylmethano-13-aza-14-oxo-15-chloro-16-cyclopentyl-17,18,19,20-tetranor-11a-carbathromb-5Z-enoic acid, (279) 9α,11α-dimethylmethano-13-aza-14-oxo-15-chloro-16-(3-propylcyclopentyl)-17,18,19,20-tetranor-11a-carbathromb-5Z-enoic acid, (280) 9α,11α-dimethylmethano-13-aza-14-oxo-15-chloro-16-(3-butylcyclopentyl)-17,18,19,20-tetranor-11a-carbathromb-5Z-enoic acid, (281) 9α,11α-dimethylmethano-13-aza-14-oxo-16-phenylthio-16-cyclopentyl-17,18,19,20-tetranor-11a-carbathromb-5Z-enoic acid, (282) -9α,11α-dimethylmethano-13-aza-14-oxo-16-phenylthio-16-(3-propylcyclopentyl)-17,18,19,20-tetranor-11a-carbathromb-5Z-enoic acid, (283) 9α,11α-dimethylmethano-13-aza-14-oxo-16-phenylthio-16-(3-butylcyclopentyl)-17,18,19,20-tetranor-11a-carbathromb-5Z-enoic acid, (284) 9α,11α-dimethylmethano-13-aza-14-oxo-15-hydroxy-17-cyclopentyl-18,19,20-trinor-11a-carbathromb-5Z-enoic acid, (285) 9α,11α-dimethylmethano-13-aza-14-oxo-15-hydroxy-17-(3-propylcyclopentyl)-18,19,20-trinor-11a-carbathromb-5Z-enoic acid, (286) 9α,11α-dimethylmethano-13-aza-14-oxo-15-hydroxy-17-(3-butylcyclopentyl)-18,19,20-trinor-11a-carbathromb-5Z-enoic acid, (287) 9α,11α-dimethylmethano-13-aza-14-oxo-15-chloro-17-cyclopentyl-18,19,20-trinor-11a-carbathromb-5Z-enoic acid, (288) 9α,11α-dimethylmethano-13-aza-14-oxo-15-chloro-17-(3-propylcyclopentyl)-18,19,20-trinor-11a-carbathromb-5Z-enoic acid, (289) 9α,11α-dimethylmethano-13-aza-14-oxo-15-chloro-17-(3-butylcyclopentyl)-18,19,20-trinor-11a-carbathromb-5Z-enoic acid, (290) 9α,11α-dimethylmethano-13-aza-14-oxo-15-phenylthio-17-cyclopentyl-18,19,20-trinor-11a-carbathromb-5Z-enoic acid, (291) 9α,11α-dimethylmethano-13-aza-14-oxo-15-phenylthio-17-(3-propylcyclopentyl)-18,19,20-trinor-11a-carbathromb-5Z-enoic acid, (292) 9α,11α-dimethylmethano-13-aza-14-oxo-16-phenylthio-17-(3-butylcyclopentyl)-18,19,20-trinor-11a-carbathromb-5Z-enoic acid, (293) 9α,11α-dimethylmethano-13-aza-14-oxo-15-hydroxy-15-cyclohexyl-16,17,18,19,20-pentanor-11a-carbathromb-5Z-enoic acid, (294) 9α,11α-dimethylmethano-13-aza-14-oxo-15-hydroxy-15-(4-propylcyclohexyl)-16,17,18,19,20-pentanor-11a-carbathromb-5Z-enoic acid, (295) 9α,11α-dimethylmethano-13-aza-14-oxo-15-hydroxy-15-(4-butylcyclohexyl)-16,17,18,19,20-pentanor-11a-carbathromb-5Z-enoic acid, (296) 9α,11α-dimethylmethano-13-aza-14-oxo-15-chloro-15-cyclohexyl-16,17,18,19,20-pentanor-11a-carbathromb-5Z-enoic acid, (297) 9α,11α-dimethylmethano-13-aza-14-oxo-15-chloro-15-(4-propylcyclohexyl)-16,17,18,19,20-pentanor-11a-carbathromb-5Z-enoic acid, (298) 9α,11α-dimethylmethano-13-aza-14-oxo-15-chloro-15-(4-butylcyclohexyl)-16,17,18,19,20-pentanor-11a-carbathromb-5Z-enoic acid, (299) 9α,11α-dimethylmethano-13-aza-14-oxo-15-phenylthio-15-cyclohexyl-16,17,18,19,20-pentanor-11a-carbathromb-5Z-enoic acid, (300) 9α,11α-dimethylmethano-13-aza-14-oxo-15-phenylthio-15-(4-propylcyclohexyl)-16,17,18,19,20-pentanor-11a-carbathromb-5Z-enoic acid, (301) 9α,11α-dimethylmethano-13-aza-14-oxo-15-phenylthio-15-(4-butylcyclohexyl)-16,17,18,19,20-pentanor-11a-carbathromb-5Z-enoic acid, (302) 9α,11α-dimethylmethano-13-aza-14-oxo-15-hydroxy-16-cyclohexyl-17,18,19,20-tetranor-11a-carbathromb-5Z-enoic acid, (303) 9α,11α-dimethylmethano-13-aza-14-oxo-15-hydroxy-16-(4-propylcyclohexyl)-17,18,19,20-tetranor-11a-carbathromb-5Z-enoic acid, (304) 9α,11α-dimethylmethano-13-aza-14-oxo-15-hydroxy-16-(4-butylcyclohexyl)-17,18,19,20-tetranor-11a-carbathromb-5Z-enoic acid, (305) 9α,11α-dimethylmethano-13-aza-14-oxo-15-chloro-16-cyclohexyl-17,18,19,20-tetranor-11a-carbathromb-5Z-enoic acid, (306) 9α,11α-dimethylmethano-13-aza-14-oxo-15-chloro-16-(4-propylcyclohexyl)-17,18,19,20-tetranor-11a-carbathromb-5Z-enoic acid, (307) 9α,11α-dimethylmethano-13-aza-14-oxo-15-chloro-16-(4-butylcyclohexyl)-17,18,19,20-tetranor-11a-carbathromb-5Z-enoic acid, (308) 9α,11α-dimethylmethano-13-aza-14-oxo-16-phenylthio-16-cyclohexyl-17,18,19,20-tetranor-11a-carbathromb-5Z-enoic acid, (309) 9α,11α-dimethylmethano-13-aza-14-oxo-16-phenylthio-16-(4-propylcyclohexyl)-17,18,19,20-tetranor-11a-carbathromb-5Z-enoic acid, (310) 9α,11α-dimethylmethano-13-aza-14-oxo-16-phenylthio-16-(4-butylcyclohexyl)-17,18,19,20-tetranor-11a-carbathromb-5Z-enoic acid, (311) 9α,11α-dimethylmethano-13-aza-14-oxo-15-hydroxy-17-cyclohexyl-18,19,20-trinor-11a-carbathromb-5Z-enoic acid, (312) 9α,11α-dimethylmethano-13-aza-14-oxo-15-hydroxy-17-(4-propylcyclohexyl)-18,19,20-trinor-11a-carbathromb-5Z-enoic acid, (313) 9α,11α-dimethylmethano-13-aza-14-oxo-15-hydroxy-17-(4-butylcyclohexyl)-18,19,20-trinor-11a-carbathromb-5Z-enoic acid, (314) 9α,11α-dimethylmethano-13-aza-14-oxo-15-chloro-17-cyclohexyl-18,19,20-trinor-11a-carbathromb-5Z-enoic acid, (315) 9α,11α-dimethylmethano-13-aza-14-oxo-15-chloro-17-(4-propylcyclohexyl)-18,19,20-trinor-11a-carbathromb-5Z-enoic acid, (316) 9α,11α-dimethylmethano-13-aza-14-oxo-15-chloro-17-(4-butylcyclohexyl)-18,19,20-trinor-11a-carbathromb-5Z-enoic acid, (317) 9α,11α-dimethylmethano-13-aza-14-oxo-16-phenylthio-17-cyclohexyl-18,19,20-trinor-11a-carbathromb-5Z-enoic acid, (318) 9α,11α-dimethylmethano-13-aza-14-oxo-16-phenylthio-17-(4-propylcyclohexyl)-18,19,20-trinor-11a-carbathromb-5Z-enoic acid and (319) 9α,11α-dimethylmethano-13-aza-14-oxo-16-phenylthio-17-(4-butylcyclohexyl)-18,19,20-trinor-11a-carbathromb-5Z-enoic acid; and esters thereof (especially methyl ester) and cyclodextrin clathrates thereof and non-toxic salts thereof.

Nomenclature

Throughout the specification and claims, the compounds of the present invention are named as analogues of TXA$_2$ (depicted hereinbefore) or 11a-carbathrombanoic acid which structure is shown in the following. And the compounds having one or two double bond is named as 11a-carbathrombenoic acid or 11a-carbathrombadienoic acid respectively [cf. Prostaglandins, 16(6), 857(1978)].

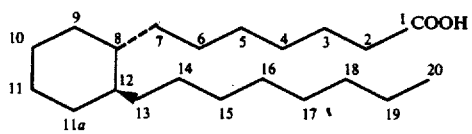

In the structural formula of the specification included claims, the dotted line (--), the thickened line (\) and the wavy line (~) indicate that the respective group attached thereto is in the backside of the plane, i.e. in α-configuration, in the front of the plane, i.e. in β-configuration, and in α- or β-configuration or a mixture thereof, respectively, according to the generally accepted nomenclature rules.

REFERENCE EXAMPLES AND EXAMPLES

The following reference examples and examples are to illustrate the present invention, but not limit the present invention.

In the reference examples and examples, "bp", "mp", "TLC", "NMR", "IR" and "MS" represent "boiling point", "melting point", "Thin layer chromatography", "Nuclear magnetic resonance spectrum", "Infrared absorption spectrum" and "Mass spectrum", respectively.

The solvents in the parentheses show the developing or eluting solvents and the ratios of the solvents used are by volume in chromatographic separations.

Unless otherwise specified, "IR" was measured by the liquid film method and "NMR" was measured in a chloroform-d (CDCl$_3$) solution, respectively.

REFERENCE EXAMPLE 1

Synthesis of (1R,5R)-10-hydroxymethyl-2-pinene

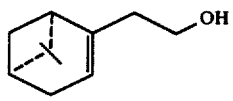

A mixture of β-pinene (32 ml) and paraformaldehyde (4 g) in sealed tube was reacted for 18 hrs at 180° C. The reaction solution was distilled to give the title compound (15.5 g) having the following physical data:
bp: 133° C./30 mmHg;
NMR: δ 5.6–5.1 (2H, m), 3.53 (2H, t), 1.27 (3H, s), 0.85 (3H, s).

REFERENCE EXAMPLE 2

Synthesis of (1R,5R)-10-(tetrahydropyran-2-yloxy)methyl-2-pinene

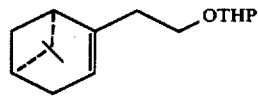

To a solution of pinene (15.5 g) prepared in reference example 1 in methylene chloride (300 ml), 2,3-dihydropyran (9.4 ml) was dropped. After addition of catalytic amount of p-toluenesulphonic acid, the solution was stirred at room temperature. After reaction, triethylamine was added to the solution. The solution was concentrated under reduced pressure. The residue was purified by column chromatography on silica gel (cyclohexane: ethyl acetate=99:1) to give the title compound (20.8 g) having the following physical data:
TLC: Rf 0.42 (cyclohexane: ethyl acetate=20:1).

REFERENCE EXAMPLE 3

Synthesis of (1S,2S,3RS,5R)-10-(tetrahydropyran-2-yloxy)methylpinan-3-ol

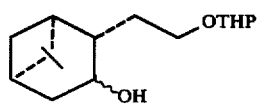

In an atmosphere of nitrogen, to a solution of pinene (20.8 g) prepared in reference example 2 in tetrahydrofuran (100 ml), a 1M solution of diboran in tetrahydrofuran (200 ml) was dropped slowly at 0° C. The solution was stirred for 2 hrs at room temperature. To the reaction mixture, water (15 ml) and a 3N aqueous solution of sodium hydroxide (50 ml) was added and then a 30% aqueous solution of hydroperoxide (33 ml) was dropped slowly. The mixture was stirred for 1 hr at 50° C. The mixture was extracted with diethyl ether. The extract was washed with a saturated aqueous solution of sodium chloride, dried over anhydrous magnesium sulphate and concentrated under reduced pressure. The residue was purified by column chromatography on silica gel (cyclohexane: ethyl acetate=4:1) to give the title compound (20.2 g) having the following physical data:
TLC: Rf 0.31 (cyclohexane: ethyl acetate=2:1);
NMR: δ 4.4 (1H, m), 1.2 (3H, s), 0.9 (3H, s).

REFERENCE EXAMPLE 4

Synthesis of (1S,2S,5R)-10-(tetrahydropyran-2-yloxy)methylpinan-3-one

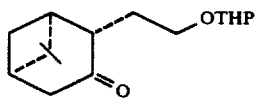

A mixture of pinane (20.2 g) prepared in reference example 3, diethyl ether (300 ml), chromic acid mixture (100 ml; prepared with 3.8 g of chromium trioxide, 12.8 g of manganese sulphate, 4.2 ml of conc. sulphuric acid and 95 ml of water) was stirred for 3 hrs at 0° C. The reaction solution was diluted with diethyl ether. The diluted solution was washed with water, a saturated aqueous solution of sodium bicarbonate and a saturated aqueous solution of sodium chloride, respectively, and then concentrated under reduced pressure. The residue was purified by column chromatography on silica gel (cyclohexane: ethyl acetate=10:1) to give the title compound (11.6 g) having the following physical data:

TLC: Rf 0.30 (cyclohexane: ethyl acetate=5:1);
NMR: δ 4.4 (1H, m), 1.3 (3H, s), 0.87 (3H, s).

REFERENCE EXAMPLE 5

Synthesis of
(1S,2S,3S,5R)-10-(tetrahydropyran-2-yloxy)methylpinan-3-ol

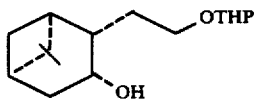

In an atmosphere of nitrogen, to a solution of pinane (11.6 g) prepared in reference example 4 in methanol (200 ml), sodium borohydride (16.5 g) was added at 0° C., and the mixture was stirred for 2 hrs at the same temperature. After addition of acetic acid, the solution was concentrated under reduced pressure. The residue was dissolved into diethyl ether, the solution was washed with water, dried over anhydrous magnesium sulphate and then concentrated under reduced pressure to give the title compound (9.86 g) having the following physical data:

TLC: Rf 0.38 (benzene: ethyl acetate=5:1);
NMR: δ 4.4 (1H, m), 1.15 (3H, s), 1.0 (3H, s).

REFERENCE EXAMPLE 6

Synthesis of
(1S,2S,3S,5R)-5-methylsulphonyloxy-10-(tetrahydropyran-2-yloxy)methylpinane

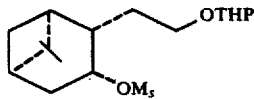

In an atmosphere of nitrogen, to a mixture of pinanol (9.86 g) prepared in reference example 5, methylene chloride (100 ml) and triethylamine (7.5 ml) methanesulphonyl chloride (3 ml) was dropped at −20° C., and the mixture was stirred for 15 min. at the same temperature. The reaction mixture diluted with diethyl ether was washed with water, a saturated aqueous solution of ammonium chloride, and a saturated aqueous sodium chloride, successively. The solution was dried over anhydrous magnesium sulphate and then concentrated under reduced pressure to give the title compound (12.7 g) having the following physical data:

TLC: Rf 0.31 (cyclohexane: ethyl acetate=2:1).

REFERENCE EXAMPLE 7

Synthesis of
(1S,2S,3S,5R)-10-(tetrahydropyran-2-yloxy)methylpinan-3-ylazide

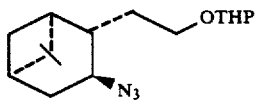

In an atmosphere of nitrogen, to a solution of pinane (12.7 g prepared in reference example 6 in hexamethylphosphoramide (40 ml), sodium azide (2.9 g) was added, and the mixture was stirred for 2 hrs at 50° C. The reaction solution diluted with diethyl ether was washed with water, dried over anhydrous magnesium sulphate and then concentrated under reduced pressure. The residue was purified by column chromatography on silica gel (cyclohexane: ethyl acetate=10:1) to give the title compound (4.03 g) having the following physical data:

TLC: Rf 0.24 (cyclohexane: ethyl acetate=20:1);
NMR: δ 4.4 (1H, m), 1.2 (3H, s), 0.93 (3H, s).

REFERENCE EXAMPLE 8

Synthesis of
N-[(1S,2S,3S,5R)-10-(tetrahydropyran-2-yloxy)methylpinan-3-yl]amine

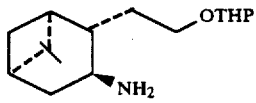

In an atmosphere of nitrogen, to a solution of azide (4.03 g) prepared in reference example 7 in diethyl ether (150 ml), lithium aluminium hydride (524 mg) was added with portions, and the mixture was refluxed for 1 hr. After addition of water, to the mixture, a 3N aqueous solution of sodium hydroxide (150 ml) was added. The mixture was extracted with diethyl ether. The extract was dried over anhydrous magnesium sulphate and then concentrated under reduced pressure to give the title compound (3.73 g) having the following physical data:

TLC: Rf 0.21 (chloroform: tetrahydrofuran:formic acid=5:2:1).

REFERENCE EXAMPLE 9

Synthesis of
N-[(1S,2S,3S,5R)-10-(tetrahydropyran-2-yloxy)methylpinan-3-yl]trifluoroacetamide

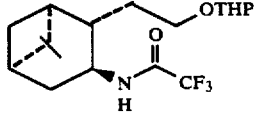

In an atmosphere of nitrogen, to a solution of amine (534 mg) prepared in reference example 8 in methylene chloride (20 ml), pyridine (1.5 ml) and trifluoroacetic anhydride (0.33 ml) was added slowly at 0° C. and the mixture was stirred for 15 min. The reaction solution diluted with diethyl ether was washed with water, dried over anhydrous magnesium sulphate and then concentrated under reduced pressure. The residue was purified by column chromatography on silica gel (cyclohexane: ethyl acetate=9:1) to give the title compound (726 mg) having the following physical data:

TLC: Rf 0.36 (cyclohexane: ethyl acetate=9:1);

NMR: δ 4.55–4.4 (1H, m), 4.4–4.05 (1H, m), 1.24 (3H, s), 1.02 (3H, s).

REFERENCE EXAMPLE 10

Synthesis of N-[(1S,2S,3S,5R)-10-hydroxymethyl-pinan-3-yl]trifluoroacetamide

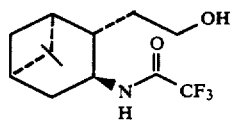

In an atmosphere of nitrogen, a mixture of acetamide (726 mg) prepared in reference example 9, methanol (20 ml) and p-toluenesulphonic acid (catalytic amount) was stirred for 1 hr at room temperature. To the reaction mixture, triethylamine (0.2 ml) was added, and the mixture was concentrated under reduced pressure. The residue was purified by column chromatography on silica gel (cyclohexane: ethyl acetate=4:1) to give the title compound (395 mg) having the following physical data:

TLC: Rf 0.36 (cyclohexane: ethyl acetate=1:1);

NMR: δ 4.55–4.1 (1H, m), 3.62 (2H, t), 1.25 (3H, s), 1.05 (3H, s).

REFERENCE EXAMPLE 11

Synthesis of N-[(1S,2S,3S,5R)-10-formylmethylpinan-3-yl]trifluoroacetamide

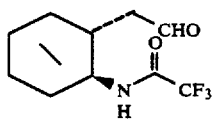

In an atmosphere of nitrogen, to a mixture of alcohol (365 mg) prepared in reference example 10, dimethylsulphoxide (20 ml) and triethylamine (1.8 ml), a solution of anhydrous sulphuric acid-pyridin complex (10.4 g) in dimethylsulphoxide (20 ml) was dropped slowly at room temperature. After stirring for 15 min. at the same temperature, the mixture was poured into ice-water. The mixture was extracted with a mixture of ethyl acetate-diethyl ether (1:1). The extract was washed with a saturated aqueous solution of sodium chloride, dried over anhydrous magnesium sulphate and then concentrated under reduced pressure. The residue was purified by column chromatography on silica gel (cyclohexane: ethyl acetate=4:1) to give the title compound (355 mg) having the following physical data:

TLC: Rf 0.44 (cyclohexane: ethyl acetate=2:1);

NMR: δ 9.73 (1H, s), 4.5–4.1 (1H, m), 1.25 (3H, s), 1.05 (3H, s).

REFERENCE EXAMPLE 12

Synthesis of (5Z)-6-[(1S,2S,3S,5R)-3-trifluoroacetylaminopinan-10-yl]hex-5-enoic acid

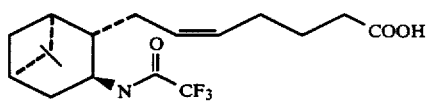

In an atmosphere of nitrogen, a suspension of sodium hydride (1.52 g; content 63%) in dimethylsulphoxide (20 ml) was stirred for 1 hr at 70° C. The solution was dropped to a solution of 4-carboxybutyl triphenyl phosphonium bromide (2.22 g) in dimethylsulphoxide (10 ml) at room temperature. After stirring for 15 min. to the reaction mixture, a solution of aldehyde (355 mg) prepared in reference example 11 in dimethylsulphoxide (5 ml) was dropped. After stirring for 30 min. at room temperature, the reaction mixture was poured into icewater. The mixture was acidified with oxalic acid. The mixture was extracted with a mixture of ethyl acetate diethyl ether (1:1). The extract was dried over anhydrous magnesium sulphate and then concentrated under reduced pressure to give the title compound (450 mg) having the following physical data:

TLC: Rf 0.42 (cyclohexane: ethyl acetate=1:2).

REFERENCE EXAMPLE 13

Synthesis of (5Z)-6-[(1S,2S,3S,5R)-3-trifluoro-acetylaminopinan-10-yl]hex-5-enoic acid methyl ester

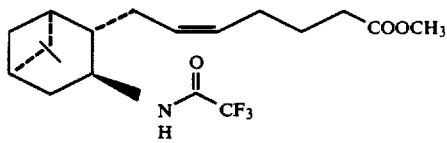

To a solution of carboxylic acid (450 mg) prepared in reference example 12 in methanol, diazomethane etherate was added till the solution was shown pale yellow. The mixture was concentrated under reduced pressure. The residue was purified by column chromatography on silica gel (cyclohexane: ethyl acetate=4:1) to give the title compound (411 mg) having the following physical data:

TLC: Rf 0.49 (cyclohexane: ethyl acetate=2:1);

NMR: δ 5.45–5.3 (2H, m), 4.5–4.1 (1H, m), 3.67 (3H, s), 1.24 (3H, s), 1.07 (3H, s);

IR: ν 3300, 3080, 1740, 1720–1690 cm$^{-1}$.

REFERENCE EXAMPLE 14

Synthesis of (5Z)-6-[(1S,2S,3S,5R)-3-aminopinan-10-yl]hex-5-enoic acid methyl ester

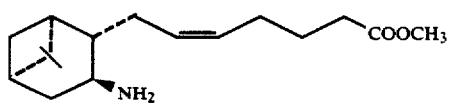

A mixture of amide (373 mg) prepared in reference example 13 and a 10% (w/v) aqueous solution of sodium hydroxide (2 ml) was stirred for 18 hrs at room temperature, and then refluxed for 1 hr. The reaction mixture was allowed to stand and acidified with 10% hydrochloric acid. After addition of excess aqueous ammonia, the mixture was filtered off. The filtrate was concentrated and the residue was dissolved into small amount of methanol. To the solution, diazomethane etherate was added till the solution was shown pale yellow. The mixture was concentrated under reduced pressure to give the title compound (180 mg) having the following physical data:

NMR: δ 5.6–5.2 (2H, m), 3.67 (3H, s), 3.3–3.0 (1H, m), 1.2 (3H, s), 0.99 (3H, s);
IR: ν 1740 cm$^{-1}$.

REFERENCE EXAMPLE 15

Synthesis of N-[(1S,2S,3S,5R)-10-(tetrahydropyran-2-yloxy) methylpinan-3-yl]hexanamide

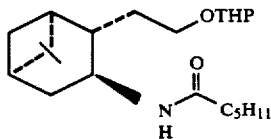

In a atmosphere of argon, to a mixture of (1S,2S, 3S,5R)-10-(tetrahydropyran-2-yloxy)methylpinan-3-ylamine (20 g; prepared in reference example 8), triethylamine (25 ml) and anhydrous tetrahydrofuran (200 ml), a solution of caproyl chloride (13 ml) in anhydrous tetrahydrofuran (30 ml) was dropped and the mixture was stirred for 2 hrs at room temperature. The diluted solution with diethyl ether was washed with water and a saturated aqueous solution of sodium chloride, successively, dried over anhydrous sodium sulphate and then concentrated under reduced pressure to give the title compound (28 g) having the following physical data:

TLC: Rf 0.27 (cyclohexane: ethyl acetate=2:1);
NMR: δ 5.6–5.2 (1H, m), 4.6–4.4 (1H, m), 1.2 (3H, s), 1.0 (3H, s);
MS: m/e 365(M+), 281, 264;
Appearance: yellow oily.

REFERENCE EXAMPLE 16

Synthesis of N-[(1S,2S,3S,5R)-10-hydroxymethylpinan-3-yl]hexanamide

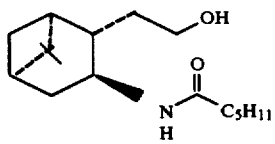

A mixture of the compound (28 g) prepared in reference example 15, p-toluensulphonic acid monohydrate (580 mg) and methanol (140 mg) was stirred for 1.5 hrs at 40° C. To the mixture, triethylamine (1 ml) was added. The mixture was washed with water and a saturated aqueous solution of sodium chloride successively, dried over anhydrous sodium sulphate and then concentrated under reduced pressure. The residue was purified by recrystallization from a mixed solvent (pentanediethyl ether) to give the title compound (10.1 g) having the following physical data:

TLC: Rf 0.10 (cyclohexane: ethyl acetate=1:1);
NMR: δ 5.7–5.3 (1H, m), 4.4–4.1 (1H, m), 3.65 (2H, t), 1.2 (3H, s), 1.0 (3H, s);
MS: m/e 281(M+), 263, 212;
Appearance: pale yellow crystal.

REFERENCE EXAMPLE 17

Synthesis of N-[(1S,2S,3S,5R)-10-formylpinan-3-yl]hexanamide

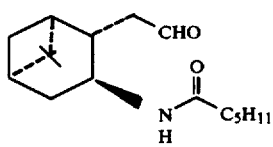

In an atmosphere of argon, to an oxidizing reagent prepared with a solution of oxalyl chloride (3.7 ml) in methylene chloride (85 ml) and a solution of dimethyl sulphoxide (6 ml) in methylene chloride (5 ml), a solution of the compound (10.1 g) prepared in reference example 16 in methylene chloride (20 ml) was dropped at −78° C. The solution was stirred for 20 min. After reaction, to the solution, triethylamine (17.5 ml) was dropped and the solution was allowed to stand to 0° C. After addition of ice-water, the mixture was stirred for 20 min. The oily layer separated was washed with water and a saturated aqueous solution of sodium chloride, successively, dried over anhydrous sodium sulphate and then concentrated under reduced pressure to give the title compound (10 g) having the following physical data:

TLC: Rf 0.34 (cyclohexane: ethyl acetate=1:1);
NMR: δ 9.7 (1H, s), 5.6–5.3 (1H, m), 4.5–4.1 (1H, m), 1.2 (3H, s), 1.0 (1H, s);
MS: m/e 279(M+), 261, 210;
Appearance: colorless oily.

REFERENCE EXAMPLE 18

Synthesis of 2-hydroxycyclopentylacetic acid

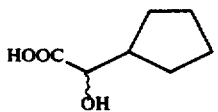

In an atmosphere of argon, to a solution of LDA (lithium diisopropylamide) prepared with a solution of diisopropylamine (60 ml) in anhydrous tetrahydrofuran (500 ml) and a 1.45M solution of butyl lithium in n-hexane (297 ml), a solution of cyclopentylacetic acid (25 g) in anhydrous toluene (100 ml) was dropped. The solution was stirred for 30 min. at room temperature and for 1 hr at 45° C. With blowing of air dried through phosphorus pentaoxide, the solution was stirred for 16 hrs. After reaction, the supernatant separated by decantation was diluted with water. The diluted solution was washed with diethyl ether, adjusted pH 2 with 6N hydrochloric acid and then extracted with ethyl acetate. The extract was washed with a saturated aqueous solution of sodium chloride and then concentrated under reduced pressure. The residue was purified by recrystal-

REFERENCE EXAMPLE 19

Synthesis of
N-[(1S,2S,3S,5R)-10-(tetrahydropyran-2-yloxy)
methylpinan-3-yl]-α-pivaloyloxycyclopentaneacetamide

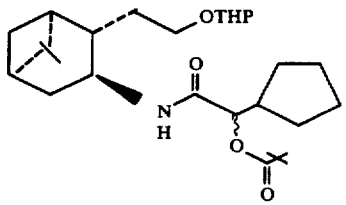

In an atmosphere of argon, to a mixture of the compound (22.7 g) prepared in reference example 18, triethylamine (90 ml) and anhydrous tetrahydrofuran (600 ml), pivaloyl chloride (39 ml) was added, at 0° C. The mixture was stirred for 40 min. at room temperature and filtered off. The filtrate was concentrated under reduced pressure. The residue was evaporated azeotropically with toluene. The obtained oil was dissolved in anhydrous tetrahydrofuran (300 ml). In an atmosphere of argon, to the solution, a solution of (1S,2S,3S,5R)-10-(tetrahydropyran-2-yloxy)methylpinan-3-ylamine (30 g; prepared in reference example 8) in anhydrous tetrahydrofuran (100 ml) was added over a period of 1 hr, and the mixture was stirred for 1.5 hrs at room temperature. The reaction solution was concentrated under reduced pressure. The residue was diluted with diethyl ether and the solution was washed with dil. hydrochloric acid, water, a 1N aqueous solution of sodium hydroxide, water and a saturated aqueous sodium chloride, successively, dried over anhydrous sodium sulphate and then concentrated under reduced pressure to give the title compound (57 g) having the following physical data:

TLC: Rf 0.42 (cyclohexane: ethyl acetate=2:1);
NMR: δ 6.0–5.7 (1H, m), 5.2–4.9 (1H, m), 4.6–4.4 (1H, m), 1.27 (9H, s), 1.2 (3H, s), 1.0 (3H, s);
MS: m/e 477(M+), 393, 376;
Appearance: pale yellow oily.

REFERENCE EXAMPLE 20

Synthesis of
N-[(1S,2S,3S,5R)-10-hydroxymethylpinan-3-yl]-α-pivaloyloxycyclopentaneacetamide

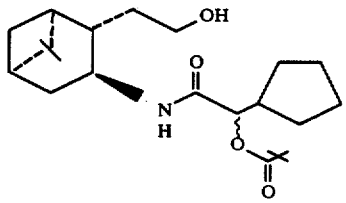

By the same procedure as reference example 16, the title compound (41 g) having the following physical data was given, with using the compound (57 g) prepared in reference example 19.

TLC: Rf 0.19 & 0.23 (cyclohexane: ethyl acetate=2:1);
NMR: δ 6.1–5.7 (1H, m), 5.00 & 4.81 (1H, two d), 4.4–4.1 (1H, m), 1.25 (9H, two d), 1.2 (3H, s), 1.0 (3H, s);
MS: m/e 393(M+), 375, 324;
Appearance: yellow wax.

REFERENCE EXAMPLE 21

Synthesis of
N-[(1S,2S,3S,5R)-10-formylpinan-3-yl]-α-pivaloyloxycyclopentaneacetamide

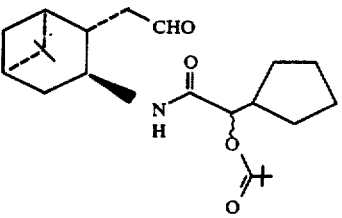

By the same procedure as reference example 17, the title compound (41 g) having the following physical data was given, with using the compound (41 g) prepared in reference example 20:

TLC: Rf 0.3 (cyclohexane: ethyl acetate=2:1);
NMR: δ 9.8–9.6 (1H, m), 6.0–5.7 (1H, m), 5.1–4.9 (1H, m), 1.27 (9H, s), 1.2 (3H, s), 1.0 (3H, s);
Appearance: yellow oily.

EXAMPLE 1

Synthesis of
9α,11α-dimethylmethano-13-aza-14-oxo-15α-hydroxy-16-phenyl-17,18,19,20-tetranor-11a-carbathromb-5Z-enoic acid and methyl ester thereof

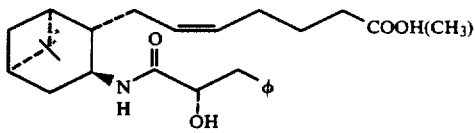

To a mixture of 2S-hydroxy-3-phenylpropionic acid (77 mg; 0.5 mmol), triethylamine (0.2 ml; 2 mmol) and anhydrous tetrahydrofuran (2 ml), pivaloyl chloride (144 μl; 0.5 mmol) was dropped at room temperature. After stirring for 1 hr at room temperature, the solution was filtered. The filtrate was concentrated. The residue was dehydrated by azeotropic evaporation with toluene to give the corresponding mixed acid anhydride. To a solution of the obtained compound dissolved in anhydrous tetrahydrofuran (1 ml), a solution of the amine (60 mg; 0.215 mmol) prepared in reference example 14 in tetrahydrofuran (0.5 ml) was dropped at room temperature. After stirring for 1 hr, the mixture was concentrated under reduced pressure. The residue was purified by column chromatography on silica gel (hexane-ethyl acetate) to give the title compound (methyl ester; 56 mg).

A 2N aqueous solution of sodium hydroxide (0.2 ml) and methanol (1 ml) were added to the obtained methyl ester. After stirring for 1 hr at 60° C., the mixture was diluted with water. The diluted solution was adjusted pH 2 with 2N hydrochloric acid and then extracted with ethyl acetate. The extract was washed with water and a saturated aqueous solution of sodium chloride successively, dried over anhydrous sodium sulphate and then concentrated under reduced pressure. The residue was purified by column chromatography on silica gel (hexane-ethyl acetate) to give the title compound (acid; 35 mg) having the following physical data:

TLC: Rf 0.21 (chloroform: methanol=10:1);

NMR: δ 7.3–7.2 (5H, m), 6.6–6.5 (1H, m), 5.5–5.2 (2H, m), 4.5–4.1 (2H, m), 1.21 (3H, s), 1.05 (3H, s);

IR: ν 3400–3300, 2920, 1710, 1630, 1530, 1240, 695 cm$^{-1}$;

MS: m/e 413(M+), 344;

Appearance: colorless oily.

By the same procedure as described above, compounds of general formula:

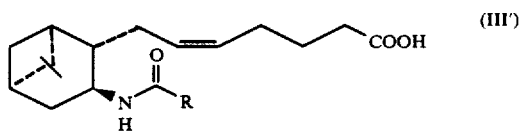

having physical data shown in the following table II were given, with using acids (0.5 mmol) of general formula:

HOOC—R          (IV')

instead of 2S-hydroxy-3-phenylpropionic acid.

TABLE II

| Example No. | Substituent R in the general formula (III') | Rf value in TLC (developing solvent) | NMR (δ) | IR (νcm⁻¹) | MS | Appearance |
|---|---|---|---|---|---|---|
| 1(a) | benzyl with CH(OH) and p-propyl substituent | 0.36 (Cyclohexane: ethyl acetate = 1:2) | 7.1(4H, s), 6.8–6.5(1H, m) 5.5–5.2(2H, m), 4.4–4.0(2H, m) 1.22(3H, q), 1.05(3H, s), 0.92(3H, t) | 3300, 2900, 1700 1620, 1520, 1230 | 469(M⁺) 400 | Colorless oily |
| 1(b) | phenyl with CH(OH)butyl | 0.44 (Cyclohexane: ethyl acetate = 1:2) | 7.4–7.1(5H, m), 6.8–6.6(1H, m) 5.6–5.2(2H, m), 4.4–4.0(2H, m) 1.22(3H, s), 1.07(3H, s) | 3300, 2920, 1700 1630, 1530, 1240 695 | 427(M⁺) 358 | Colorless oily |
| 1(c) | alkyl chain with OH | 0.44 (Cyclohexane: ethyl acetate = 1:2) | 6.8–6.6(1H, m), 5.6–5.2(2H, m) 4.4–4.1(2H, m), 1.23(3H, s) 1.07(3H, s), 1.0–0.8(3H, m) | 3310, 2920, 1700 1625, 1525, 1240 | 393(M⁺) 324 | Colorless oily |
| 1(d) | phenyl-CH(CH₃)- | 0.31 (Cyclohexane: ethyl acetate = 1:1) | 7.3–7.1(5H, m), 5.4–5.0(3H, m) 4.2–4.9(1H, m), 1.21(3H, s) 1.18(3H, s), 1.0(3H, s) | 3280, 2920, 1700 1620, 1530, 1240 730, 690 | 411(M⁺) 342 | Colorless oily |
| 1(e) | p-tolyl-CH(CH₃)- | 0.31 (Cyclohexane: ethyl acetate = 1:1) | 7.05(4H, s), 5.4–5.0(3H, m) 4.2–4.0(1H, m), 2.29(3H, s) 1.2–1.1(6H, m), 1.0(3H, s) | 3300, 2920, 1700 1620, 1530, 1230 800 | 425(M⁺) 356 | Colorless oily |
| 1(f) | cyclohexyl | 0.31 (Cyclohexane: ethyl acetate = 1:1) | 5.6–5.2(2H, m), 4.3–4.1(1H, m) 1.22(3H, s), 1.06(3H, s) | 3280, 2920, 1700 1530, 1440, 1620 1230 | 403(M⁺) 334 | Colorless oily |
| 1(g) | cyclopentyl | 0.31 (Cyclohexane: ethyl acetate = 1:1) | 5.6–5.2(3H, m), 4.3–4.1(1H, m) 1.22(3H, s), 1.05(3H, s) | 3280, 2920, 1700 1620, 1540, 1240 | 389(M⁺) 320 | Colorless oily |
| 1(h) | o-methoxyphenyl | 0.31 (Cyclohexane: ethyl acetate = 1:1) | 7.4–7.2(2H, m), 7.1–6.9(3H, m) 6.6–6.4(1H, m), 5.4–5.2(2H, m) 4.5(2H, s), 4.5–4.2(1H, m) 1.22(3H, s), 1.07(3H, s) | 3300, 2920, 1700 1640, 1230, 1060 750, 690 | 399(M⁺) 330 306 | Colorless oily |

TABLE II-continued

| Example No. | Substituent R in the general formula (III') | Rf value in TLC (developing solvent) | NMR (δ) | IR (νcm⁻¹) | MS | Appearance |
|---|---|---|---|---|---|---|
| 1(i) | [structure: phenylthio-ethyl] | 0.31 (Cyclohexane: ethyl acetate = 1:1) | 7.4–7.1(5H, m), 6.9–6.7(1H, m) 5.4–5.0(2H, m), 4.3–4.0(1H, m) 3.75(2H, d), 1.18(3H, m) 1.01(3H, s) | 3280, 2920, 1700 1630, 1230, 735 690 | 415(M⁺) 346 306 | Pale yellow oily |
| 1(j) | [structure: cyclopentyl chain] | 0.42 (Cyclohexane: ethyl acetate = 1:1) | 5.5–5.2(3H, m), 4.3–4.1(1H, m) 1.22(3H, s), 1.05(3H, s) 1.0–0.8(4H, m) | 3280, 2920, 1705 1620, 1535, 1230 | 417(M⁺) 348 | Colorless oily |
| 1(k) | [structure: p-tolyl chain, CH₃] | 0.23 (Cyclohexane: ethyl acetate = 1:1) | 7.09(4H, s), 5.5–5.2(3H, m) 4.3–4.1(1H, m), 2.30(3H, s) 1.19(3H, s), 1.02(3H, s) | 3280, 2920, 1705 1620, 1540, 1240 810 | 411(M⁺) 342 | Colorless oily |
| 1(l) | [structure: cyclohexyl chain, H] | 0.32 (Cyclohexane: ethyl acetate = 1:1) | 5.6–5.2(3H, m), 4.3–4.1(1H, m) 1.21(3H, s), 1.05(3H, s) | 3270, 2920, 1705 1620, 1540, 1235 | 417(M⁺) 348 | Colorless oily |
| 1(m) | [structure: naphthyl chain] | 0.23 (Cyclohexane: ethyl acetate = 1:1) | 7.9–7.6(4H, m), 7.6–7.3(3H, m) 5.5–5.2(3H, m), 4.3–4.1(1H, m) 3.74(2H, s), 1.17(3H, s) 1.02(3H, s) | 3270, 2910, 1700 1620, 1535, 1230 | 433(M⁺) 364 | Colorless wax |
| 1(n) | [structure: indolyl chain, NH] | 0.29 (Cyclohexane: ethyl acetate = 1:2) | 8.2–8.0(1H, m), 7.6(1H, d) 7.35(1H, d), 7.3–6.9(3H, m) 5.5–5.2(3H, m), 4.4–4.1(1H, m) 1.20(3H, s), 1.04(3H, s) | 3300, 2920, 1705 1615, 1230, 750 | 450(M⁺) | Colorless wax |
| 1(o) | [structure: cyclopentyl chain] | 0.17 (Cyclohexane: ethyl acetate = 1:1) | 6.6–5.2(3H, m), 4.3–4.1(1H, m) 1.22(3H, s), 1.05(3H, s) | 3280, 2900, 1700 1620, 1530, 1240 | 361(M⁺) 292 | Colorless oily |
| 1(p) | [structure: branched isoprenoid chain, CH₃] | 0.22 (Cyclohexane: ethyl acetate = 1:1) | 5.6–5.2(3H, m), 5.2–5.0(1H, m) 4.3–4.1(1H, m), 1.67(3H, s) 1.60(3H, s), 1.22(3H, s) 1.05(3H, s), 0.94(3H, d) | 3280, 2920, 1705 1620, 1540, 1235 | 417(M⁺) 348 | Colorless oily |

TABLE II-continued

| Example No. | Substituent R in the general formula (III') | Rf value in TLC (developing solvent) | NMR (δ) | IR (νcm⁻¹) | MS | Appearance |
|---|---|---|---|---|---|---|
| 1(q) | 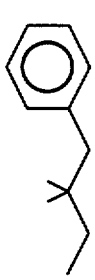 | 0.25 (Cyclohexane: ethyl acetate = 1:1) | 7.4–7.1(5H, m), 5.5–5.2(3H, m) 4.4–4.1(1H, m), 2.68(3H, s) 2.04(3H, s), 1.21(3H, s) 1.05(3H, s), 1.04(3H, s) | 3280, 2900, 1700 1620, 1530, 1230 695 | 439(M⁺) 370 | Colorless oily |
| 1(r) | 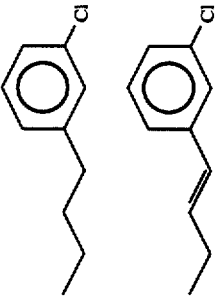 | 0.16 (Cyclohexane: ethyl acetate = 1:1) | 7.6–7.0(4H, m), 5.5–5.2(3H, m) 4.4–4.1(1H, m), 1.22(3H, s) 1.05(3H, s) | 3280, 2900, 1700 1620, 1540, 1240 780, 695 | 445(M⁺) 376 | Colorless oily |
| 1(s) | 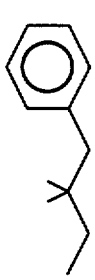 | 0.15 (Cyclohexane: ethyl acetate = 1:1) | 7.4–7.2(4H, m), 6.48(1H, d) 6.33(1H, dd), 5.7–5.3(3H, m) 4.4–4.1(1H, m), 3.15(2H, d) 1.21(3H, s), 1.05(3H, s) | 3280, 2900, 1700 1610, 1530, 1230 775 | 443(M⁺) 374 | Yellow oily |
| 1(t) | 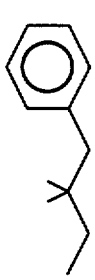 | 0.40 (Cyclohexane: ethyl acetate = 1:2) | 7.1–6.8(1H, m), 5.5–5.2(2H, m) 4.4–4.1(1H, m), 3.25(2H, s) 1.22(3H, s), 1.06(3H, s) | 3280, 2900, 1700 1630, 1530, 1230 | 407(M⁺) 338 | Colorless oily |
| 1(u) | 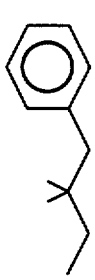 | 0.45 (Cyclohexane: ethyl acetate = 1:2) | 5.6–5.2(3H, m), 4.3–4.1(1H, m) 1.22(3H, s), 1.06(3H, s) | 3270, 2900, 1700 1620, 1530, 1225 | 403(M⁺) 334 | Colorless oily |
| 1(v) | 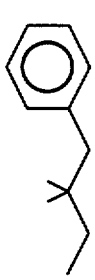 | 0.45 (Cyclohexane: ethyl acetate = 1:2) | 6.83(1H, dd), 5.75(1H, d) 5.6–5.2(3H, m), 4.4–4.2(1H, m) 1.22(3H, s), 1.06(3H, s) | 3270, 2920, 1705 1660, 1610, 1535 1230 | 401(M⁺) 332 | Colorless oily |
| 1(w) | 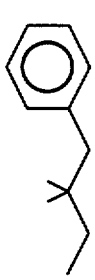 | 0.47 (Cyclohexane: ethyl acetate = 1:2) | 7.4–7.1(5H, m), 5.6–5.2(3H, m) 4.4–4.1(1H, m), 1.21(3H, s) 1.05(3H, s), 0.94(3H, d) | 3280, 2910, 1700 1620, 1540, 1235 735, 690 | 425(M⁺) 356 | Colorless oily |
| 1(x) | 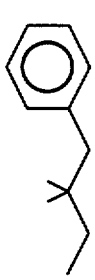 | 0.51 (Cyclohexane: ethyl acetate = 1:1) | 7.6–7.2(5H, m), 6.0–5.7(1H, m) 5.5–5.2(2H, m), 4.3–4.1(1H, m) 3.6–3.4(1H, m), 1.2(3H, s) 1.04(3H, s) | 3280, 2900, 1700 1620, 1535, 1235 745, 690 | 511(M⁺) 442 409 | Colorless oily |

TABLE II-continued

| Example No. | Substituent R in the general formula (III') | Rf value in TLC (developing solvent) | NMR (δ) | IR (νcm⁻¹) | MS | Appearance |
|---|---|---|---|---|---|---|
| 1(y) | cyclopentyl-S-CH₂CH₂CH₂- | 0.20 (Cyclohexane: ethyl acetate = 1:1) | 6.0–5.8(1H, m), 5.5–5.2(2H, m) 4.4–4.1(1H, m), 1.22(3H, s) 1.05(3H, s) | 3280, 2920, 1705 1630, 1540, 1230 | 421(M⁺) 352 | Colorless oily |
| 1(z) | cyclopentyl-S-CH₂CH₂CH₂CH₂- | 0.20 (Cyclohexane: ethyl acetate = 1:1) | 5.8–5.6(1H, m), 5.5–5.2(2H, m) 4.3–4.1(1H, m), 1.22(3H, s) 1.05(3H, s), 1.21(3H, s), 1.05(3H, s) | 3280, 2920, 1705 1620, 1540, 1440 1235 | 435(M⁺) 367 | Colorless oily |
| 1(aa) | Ph-S-CH₂CH₂CH₂- | 0.20 (Cyclohexane: ethyl acetate = 1:1) | 7.4–7.1(5H, m), 5.7–5.2(3H, m) 4.3–4.1(1H, m), 3.23(2H, t) 1.21(3H, s), 1.05(3H, s) | 3280, 2910, 1700 1620, 1540, 1230 730, 685 | 429(M⁺) 360 | Colorless oily |
| 1(bb) | cyclopentyl(OH)- | 0.13 (Cyclohexane: ethyl acetate = 1:1) | 7.0–6.9(1H, m), 5.5–5.2(2H, m) 4.3–4.1(1H, m), 1.23(3H, s) 1.07(3H, s) | 3400, 3300, 2900 1705, 1620, 1520 1190 | 377(M⁺) 359 308 | Colorless wax |
| 1(cc) | indanyl- | 0.23 (Cyclohexane: ethyl acetate = 1:1) | 7.3–7.1(4H, m), 5.7–5.2(3H, m) 4.4–4.2(1H, m), 1.22(3H, s) 1.06(3H, s) | 3280, 2920, 1700 1620, 1535, 1230 738 | 423(M⁺) 354 307 | Colorless wax |
| 1(dd) | CH₃-CH(CH₂-)- branched alkyl | 0.23 (Cyclohexane: ethyl acetate = 1:1) | 5.6–5.2(3H, m), 4.4–4.1(1H, m) 1.21(3H, s), 1.05(3H, m) 1.0–0.8(7H, m) | 3280, 2910, 1705 1620, 1540, 1240 | 363(M⁺) 294 | Colorless oily |
| 1(ee) | isobutyl- | 0.19 (Cyclohexane: ethyl acetate = 1:1) | 5.6–5.2(3H, m), 4.4–4.1(1H, m) 1.22(3H, s), 1.06(3H, s) 0.97(6H, d) | 3280, 2920, 1700 1620, 1530, 1360 1235 | 349(M⁺) 380 | Colorless oily |
| 1(ff) | isobutyl-CH(OH)CH₂- | 0.22 (Hexane: ethyl acetate = 1:2) | 6.8–6.6(1H, m), 5.6–5.2(2H, m) 4.4–4.0(2H, m), 1.22(3H, s) 1.06(3H, s), 0.9(3H, t) | 3300, 2920, 1705 1630, 1530, 1240 | 379(M⁺) 310 | Colorless oily |
| 1(gg) | isobutyl-CH(OH)- | 0.26 (Hexane: ethyl acetate = 1:2) | 6.8–6.6(1H, m), 5.6–5.2(2H, m) 4.4–4.0(2H, m), 1.23(3H, s) 1.07(3H, s), 0.96(6H, d) | 3300, 2900, 1700 1620, 1520, 1230 1140 | 379(M⁺) 310 | Colorless oily |
| 1(hh) | isobutyl-CH₂- | 0.32 (Hexane: ethyl acetate = 1:2) | 5.6–5.2(3H, m), 4.3–4.1(1H, m) 1.21(3H, s), 1.05(3H, s) 0.91(6H, d) | 3270, 2900, 1700 1620, 1530, 1230 | 363(M⁺) 294 | Colorless oily |

TABLE II-continued

| Example No. | Substituent R in the general formula (III') | Rf value in TLC (developing solvent) | NMR (δ) | IR (νcm⁻¹) | MS | Appearance |
|---|---|---|---|---|---|---|
| 1(ii) | (structure: chain with Cl) | 0.21 (Hexane: ethyl acetate = 1:2) | 5.6-5.2(3H, m), 4.4-4.2(1H, m), 3.55(2H, t), 1.21(3H, s), 1.05(3H, s) | 3270, 2900, 1700, 1620, 1530, 1230 | 383(M⁺) 347 314 | Colorless oily |
| 1(jj) | (structure with OH, more polar) | 0.37 (Chloroform: tetrahydrofuran: acetic acid = 20:2:1) | 6.6-6.4(1H, m), 5.5-5.2(2H, m), 4.4-4.2(1H, m), 3.99(1H, d), 1.22(3H, s), 1.06(3H, s), 1.02(3H, d), 0.89(3H, d) | 3300, 2920, 1700, 1620, 1520, 1230 | 365(M⁺) 296 | Colorless oily |
| 1(kk) | (structure with OH, less polar) | 0.39 (Chloroform: tetrahydrofuran: acetic acid = 20:2:1) | 6.8-6.4(1H, m), 5.6-5.2(2H, m), 4.4-4.2(1H, m), 4.07(1H, d), 1.22(3H, s), 1.06(3H, s), 1.02(3H, d), 0.88(3H, d) | 3300, 2900, 1700, 1630, 1520, 1240 | 365(M⁺) 296 | Colorless oily |
| 1(ll) | (structure with OH) | 0.17 (Hexane: ethyl acetate = 1:2) | 6.8-6.6(1H, m), 5.6-5.2(2H, m), 4.4-4.0(2H, m), 1.22(3H, s), 1.06(3H, s), 0.99(3H, t) | 3300, 2900, 1705, 1620, 1520, 1225 | 351(M⁺) 282 | Colorless oily |
| 1(mm) | (structure with CH₃ and cyclopentyl) | 0.43 (Hexane: ethyl acetate = 1:2) | 5.6-5.2(3H, m), 4.4-4.1(1H, m), 1.21(3H, s), 1.05(3H, s), 1.0-0.8(7H, m) | 3280, 2910, 1705, 1620, 1535, 1230 | 377(M⁺) 308 | Colorless oily |
| 1(nn) | (structure with CH₃ and cyclopentyl) | 0.47 (Hexane: ethyl acetate = 1:2) | 5.6-5.2(3H, m), 4.4-4.1(1H, m), 1.21(3H, s), 1.05(3H, s), 0.93(3H, d) | 3280, 2930, 1710, 1620, 1540, 1230 | 403(M⁺) 334 | Colorless oily |
| 1(oo) | (structure with CH₃ groups) | 0.23 (Hexane: ethyl acetate = 1:2) | 5.6-5.2(3H, m), 4.4-4.1(1H, m), 1.21(3H, s), 1.05(3H, s), 1.0-0.8(7H, m) | 3280, 2920, 1705, 1540, 1375 | 377(M⁺) 308 | Colorless oily |
| 1(pp) | (structure with CH₃ and cyclopentyl) | 0.33 (Hexane: ethyl acetate = 1:2) | 5.6-5.2(3H, m), 4.4-4.1(1H, m), 1.22(3H, s), 1.05(3H, s), 0.94(3H, d) | 3280, 2940, 1705, 1620, 1540, 1240 | 417(M⁺) 348 | Pale yellow oily |
| 1(qq) | (structure with CH₃ and cyclopentyl) | 0.31 (Hexane: ethyl acetate = 1:2) | 5.6-5.2(3H, m), 4.4-4.1(1H, m), 1.22(3H, s), 1.05(3H, s), 0.88(3H, d) | 3270, 2930, 1705, 1620, 1535, 1370, 1230 | 417(M⁺) 348 | Colorless oily |

TABLE II-continued

| Example No. | Substituent R in the general formula (III') | Rf value in TLC (developing solvent) | NMR (δ) | IR (νcm⁻¹) | MS | Appearance |
|---|---|---|---|---|---|---|
| 1(rr) | CH₃ with phenylpropyl branch | 0.26 (Hexane: ethyl acetate = 1:2) | 7.3–7.1(3H, m), 5.6–5.2(3H, m), 4.4–4.1(1H, m), 1.21(3H, s), 1.05(3H, s), 1.01(3H, d) | 3280, 2920, 1705, 1630, 1540, 1240, 695 | 439(M⁺) 370 | Colorless oily |
| 1(ss) | isohexyl branch | 0.45 (Hexane: ethyl acetate = 1:2) | 5.6–5.2(3H, m), 4.4–4.1(1H, m), 1.20(3H, s), 1.04(3H, s), 0.87(6H, d) | 3270, 2920, 1700, 1620, 1535, 1375 | 377(M⁺) 308 | Colorless oily |
| 1(tt) | CH₃ with alkyl branch | 0.50 (Hexane: ethyl acetate = 1:2) | 5.6–5.2(3H, m), 4.4–4.1(1H, m), 1.21(3H, s), 1.05(3H, s), 1.0–0.8(10H, m) | 3280, 2940, 1705, 1620, 1540, 1240 | 391(M⁺) 322 | Colorless oily |

EXAMPLE 2

Synthesis of 9α,11α-dimethylmethano-13-aza-14-oxo-15,15-dimethyl-17-phenyl-18,19,20-trinor-11a-carbathromb-5Z-enoic acid and methyl ester thereof

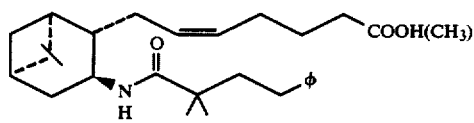

In an atmosphere of argon, a mixture of 2,2-dimethyl-4-phenylbutanoic acid (194 mg; 1 mmol) and thionyl chloride (0.3 ml; 4 mmol) was refluxed for 5 hrs and then concentrated. The solution was dehydrated by azeotropic evaporation with toluene to give the corresponding acid chloride. In an atmosphere of argon, to a mixture of the amine (100 mg; 0.36 mmol) prepared in reference example 14, triethylamine (0.2 ml; 2 mmol) and anhydrous diethyl ether (1 ml), a solution of the acid chloride prepared above in anhydrous diethyl ether (0.5 ml) was dropped at room temperature, and the mixture was stirred for 16 hrs at the same temperature. Crystals deposited were removed by filtration and the filtrate was washed with a 1N aqueous solution of sodium hydroxide, water and a saturated aqueous solution of sodium chloride successively, dried over anhydrous magnesium sulphate and then concentrated under reduced pressure. The residue was purified by column chromatography on silica gel (hexane-ethyl acetate) to give the title compound (methyl ester; 117 mg).

The methyl ester obtained was hydrolized by the same procedure as described in example 1 to give the title compound (acid; 65 mg) having the following physical data:

TLC: Rf 0.16 (chlorohexane: ethyl acetate=2:1);

NMR: δ 7.3–7.1 (5H, m), 5.6–5.5 (1H, m), 5.4–5.2 (2H, m), 4.3–4.1 (1H, m), 1.24 (6H, s), 1.22 (3H, s), 1.06 (3H, s);

IR: ν 3340, 2920, 1705, 1620, 1520, 1230, 695 cm$^{-1}$;

MS: m/e 439(M+), 370;

Appearance: colorless oily.

By the same procedure as described above, compounds of general formula:

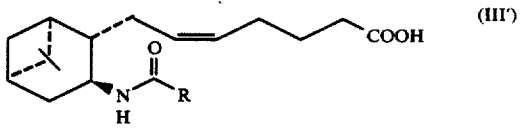

having physical data shown in the following table III were given, with using acids (1 mmol) of general formula:

$$HOOC-R \qquad (IV')$$

instead of 2,2-dimethyl-4-phenylbutanoic acid.

TABLE III

| Example No. | Substituent R in the general formula (III') | Rf value in TLC (developing solvent) | NMR (δ) | IR (νcm⁻¹) | MS | Appearance |
|---|---|---|---|---|---|---|
| 2(a) |  | 0.16 (Cyclohexane:ethyl acetate = 2:1) | 7.3–7.1(5H, m), 5.6–5.1(3H, m) 4.3–4.0(1H, m), 1.21(3H, s) 1.15(6H, s), 1.04(3H, s) | 3340, 2920, 1705 1620, 1520, 1230 750, 695 | 453(M⁺) 384 | Colorless oily |
| 2(b) | 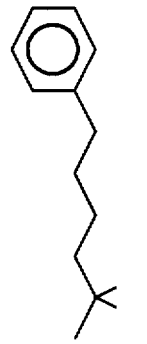 | 0.17 (Cyclohexane:ethyl acetate = 2:1) | 7.3–7.1(5H, m), 5.6–5.5(1H, m) 5.4–5.2(2H, m), 4.3–4.1(1H, m) 1.21(3H, s), 1.15(6H, s) 1.04(3H, s) | 3350, 2920, 1705 1620, 1520, 1240 695 | 467(M⁺) 398 | Colorless oily |
| 2(c) |  | 0.25 (Cyclohexane:ethyl acetate = 2:1) | 5.6–5.5(1H, m), 5.4–5.2(2H, m) 4.3–4.1(1H, m), 1.21(3H, s) 1.16(6H, s), 1.05(3H, s) | 3350, 2920, 1710 1625, 1525, 1450 1240 | 473(M⁺) 404 | Colorless oily |
| 2(d) |  | 0.33 (Cyclohexane:ethyl acetate = 2:1) | 6.2–6.0(1H, m), 5.4–5.2(2H, m) 4.3–4.0(1H, m), 1.79(3H, t) 1.23(9H, m), 1.04(3H, s) | 3340, 2920, 1705 1620, 1520, 1230 | 387(M⁺) 372 318 | Yellow oily |
| 2(e) |  | 0.41 (Cyclohexane:ethyl acetate = 1:1) | 5.6–5.5(1H, m), 5.4–5.2(2H, m) 4.3–4.1(1H, m), 1.21(3H, s) 1.15(6H, s), 1.04(3H, s) 1.0–0.8(4H, m) | 3340, 2900, 1705 1620, 1520, 1230 | 391(M⁺) 322 | Yellow oily |
| 2(f) | 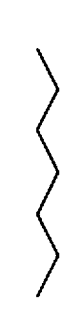 | 0.28 (Cyclohexane:ethyl acetate = 1:1) | 5.6–5.2(3H, m), 4.3–4.1(1H, m) 1.21(3H, s), 1.05(3H, s) 1.0–0.8(4H, m) | 3280, 2920, 1705 1620, 1540, 1240 | 377(M⁺) 308 | Colorless oily |
| 2(g) |  | 0.26 (Cyclohexane:ethyl acetate = 1:1) | 5.6–5.2(3H, m), 4.4–4.1(1H, m) 1.22(3H, s), 1.05(3H, s) | 3280, 2920, 1705 1630, 1540, 1240 | 375(M⁺) 306 | Colorless oily |
| 2(h) |  | 0.28 (Cyclohexane:ethyl acetate = 1:1) | 6.5–6.3(1H, m), 5.5–5.2(2H, m) 4.36(1H, dd), 4.3–4.1(1H, m) 1.23(3H, s), 1.06(3H, s) | 3270, 2900, 1700 1660–1620, 1540 1230 | 409(M⁺) 340 | Colorless oily |
| 2(i) |  | 0.07 (Cyclohexane:ethyl acetate = 1:1) | 5.6–5.2(2H, m), 4.4–4.1(1H, m) 4.36(1H, dd), 1.06(3H, s) 0.96(3H, t) | 3270, 2900, 1700 1610, 1540, 1230 | 335(M⁺) 266 | Colorless oily |

TABLE III-continued

| Example No. | Substituent R in the general formula (III') | Rf value in TLC (developing solvent) | NMR (δ) | IR (νcm⁻¹) | MS | Appearance |
|---|---|---|---|---|---|---|
| 2(j) | (n-pentyl chain) | 0.11 (Cyclohexane:ethyl acetate = 1:1) | 5.6-5.2(3H, m), 4.4-4.1(1H, m) 1.22(3H, s), 1.05(3H, s) 0.92(3H, t) | 3270, 2900, 1695 1610, 1530, 1225 | 349(M$^+$) 280 | Colorless oily |
| 2(k) | (cyclopentylmethyl with Cl) | 0.38 (Cyclohexane:ethyl acetate = 1:1) | 6.6-6.3(1H, m), 5.5-5.2(2H, m) 4.4-4.1(2H, m), 1.23(3H, s) 1.06(3H, s) | 3270, 2920, 1700 1640, 1530, 1440 1230 | 423(M$^+$) 354 | Colorless Oily |

EXAMPLE 3

Synthesis of 9α,11α-dimethylmethano-13-aza-14-oxo-16-(4-methoxyphenyl)-17,18,19,20-tetranor-11a-carbathromb-5Z-enoic acid and methyl ester thereof

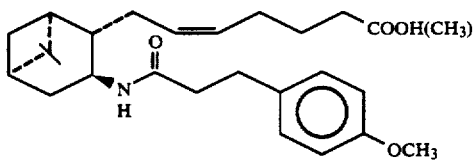

In an atmosphere of argon, to a solution of 3-(4-methoxyphenyl)propionic acid (108 mg; 0.6 mmol) in anhydrous methylene chloride (3 ml), DCC (154 mg; 0.75 mmol;dicyclohexylcarbodiimide) was added and the mixture was stirred for 1 hr at 0° C. To the solution, a solution of the amine (80 mg; 0.29 mmol) prepared in reference example 14 in pyridine (0.7 ml) was dropped and the mixture was stirred for 2 hrs. The reaction solution was filtered off and the filtrate was diluted with ethyl acetate. The diluted solution was washed with dil. hydrochloric acid, water and a saturated aqueous solution of sodium chloride, successively, dried over anhydrous sodium sulphate and then concentrated under reduced pressure. The residue was purified by column chromatography on silica gel (hexane-ethyl acetate) to give the title compound (methyl ester; 80 mg).

The methyl ester obtained was hydrolized by the same procedure as described in example 1 to give the title compound (acid; 38 mg) having the following physical data:

TLC: Rf 0.25 (chlorohexane: ethyl acetate = 1:2);
NMR: δ 7.1 (2H, d), 6.8 (2H, d), 5.5–5.2 (3H, m), 4.3–4.0 (1H, m), 3.77 (3H, s), 1.18 (3H, s 1.02 (3H, s);
IR: ν3290, 2920, 1710, 1610, 1510, 1240, 820 cm$^{-1}$;
Appearance: colorless oily.

By the same procedure as described above, compounds of general formula:

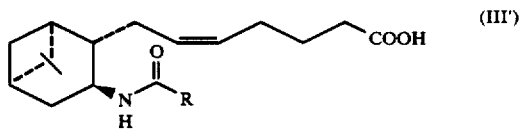

(III')

having physical data shown in the following table IV were given, with using acids (0.6 mmol) of general formula:

HOOC—R (IV')

instead of 3-(4-methoxyphenyl)propoinic acid.

TABLE IV

| Example No. | Substituent R in the general formula (III') | Rf value in TLC (developing solvent) | NMR (δ) | IR (νcm⁻¹) | MS | Appearance |
|---|---|---|---|---|---|---|
| 3(a) | (phenyl-CH(OH)-CH-) | 0.21 (Chloroform:methyl = 10:1) | 7.4-7.2(5H, m), 6.6-6.3(1H, m) 5.5-5.2(2H, m), 4.4-4.1(2H, m) 3.20(1H, s), 2.94(1H, dd) 1.2(3H, s), 1.04(3H, s) | 3300, 2920, 1700 1630, 1530, 1090 750, 690 | 413(M⁺) 395 | Colorless oily |
| 3(b) | (phenyl-CH₂-CH₂-CH-) | 0.29 (Cyclohexane: ethyl acetate = 1:2) | 7.3-7.1(5H, m), 5.5-5.2(3H, m) 4.3-4.1(1H, m), 2.95(2H, t) 1.18(3H, s), 1.03(3H, s) | 3290, 2920, 1710 1620, 1545, 1240 695 | 397(M⁺) 328 | Colorless oily |
| 3(c) | (phenyl-CH₂-CH₂-CH₂-CH-) | 0.31 (Cyclohexane: ethyl acetate = 1:2) | 7.3-7.1(5H, m), 5.5-5.2(3H, m) 4.3-4.1(1H, m), 1.21(3H, s) 1.05(3H, s) | 3290, 2920, 1705 1620, 1540, 1230 695 | 411(M⁺) 342 | Colorless oily |
| 3(d) | (4-benzyl-pentenyl) | 0.35 (Cyclohexane: ethyl acetate = 1:2) | 7.25(2H, s), 7.09(2H, s) 5.4-5.2(3H, m), 4.3-4.1(1H, s) 1.18(3H, s), 1.01(3H, s) 0.90(3H, t) | 3290, 2920, 1705 1630, 1540 | 453(M⁺) 384 | Colorless oily |
| 3(e) | (phenyl-CH₂-C(CH₃)=CH-) | 0.40 (Cyclohexane:ethyl acetate = 1:2) | 7.4-7.2(6H, m), 6.0-5.7(1H, m) 5.5-5.2(2H, m), 4.5-4.2(1H, m) 2.10(3H, d), 1.23(3H, s) 1.08(3H, s) | 3290, 2920, 1705 1640, 1600, 1525 1230, 695 | 409(M⁺) 340 | Colorless oily |
| 3(f) | (phenyl-CH₂-C(CH₃)₂-CH-) | 0.44 (Cyclohexane:ethyl acetate = 1:2) | 7.3-7.1(5H, m), 5.5-5.2(3H, m) 4.3-4.1(1H, m), 2.83(2H, dd) 1.20(3H, s), 1.19(3H, s) 1.14(3H, s), 1.05(3H, s) | 3350, 2910, 1710 1620, 1240, 745 705 | 425(M⁺) 356 | Hemi-crystalline |
| 3(g) | (phenyl-pentyl-CH-) | 0.25 (Cyclohexane:ethyl acetate = 1:1) | 7.4-7.1(5H, m), 5.6-5.4(1H, m) 5.4-5.2(2H, s), 4.4-4.1(1H, m) 1.21(3H, s), 1.04(3H, s) | 3290, 2920, 1700 1620, 1540, 1235 745, 690 | 425(M⁺) 356 | Colorless oily |

EXAMPLE 4

Synthesis of
9α,11α-dimethylmethano-13,15-diaza-14-oxo-20-nor-11a-carbathromb-5Z-enoic acid and methyl ester thereof

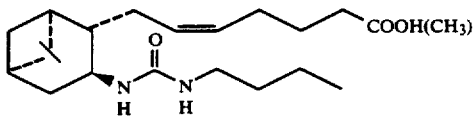

In an atmosphere of argon, to a solution of n-butyl isocyanate (60 μl) in anhydrous methylene chloride (1 ml), a solution of the amine (100 mg) prepared in reference example 14 in anhydrous methylene chloride (0.5 ml) was dropped at 0° C., and the mixture was stirred for 1 hr. The reaction solution was concentrated under reduced pressure, and the residue was purified by column chromatography on silica gel (hexane:ethyl acetate=3:1) to give the title compound (methyl ester; 100 mg).

To the methyl ester obtained, a mixture of a 2N aqueous solution of sodium hydroxide (0.5 ml) and methanol (1 ml) was added, and then the mixture was stirred for 1 hr at 50° C. The solution diluted with water was adjusted to pH 2 with dil. hydrochloric acid. The solution was extracted with ethyl acetate. The extract was washed with water and a saturated aqueous solution of soduum chloride, dried over anhydrous sodium sulphate and then concentrated under reduced pressure. The residue was purified by column chromatography on silica gel (hexane:ethyl acetate=1:1) to give the title compound (acid; 73 mg) having the following physical data:

TLC: Rf 0.20 (hexane:ethyl acetate=1:2);

NMR: δ5.6–5.3 (2H, m), 3.9–3.7 (1H, m), 3.3–3.1 (2H, m), 1.22 (3H, s), 1.03 (3H, s), 0.93 (3H, t);

IR: ν3400–3300, 3000–2850, 1700, 1640–1540, 1225 cm$^{-1}$;

MS: m/e 364(M+), 295;

Appearance: colorless oily.

EXAMPLE 5 (i)

Synthesis of
9α,11α-dimethylmethano-13-aza-14-oxo-15β-benzyloxycarbonylamino-16-phenyl-17,18,19,20-tetranor-11a-carbathromb-5Z-enoic acid methyl ester

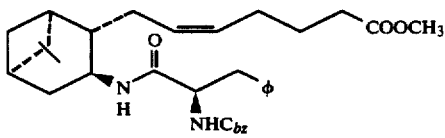

In an atmosphere of argon, to a solution of 2-benzyloxycarbonylamino-3-phenylpropionic acid (600 mg) in anhydrous tetrahydrofuran (10 ml), triethylamine (370 μl) was added and the mixture was stirred at 0° C. To the stirring solution, pivaloyl chloride (268 μl) was dropped, and the mixture was stirred for 1 hr at room temperature. To the reaction solution, a solution of the amine (400 mg) prepared in reference example 14 in anhydrous tetrahydrofuran (3 ml) was dropped at room temperature, and the mixture was stirred for 1.5 hrs. The reaction solution was diluted with water. The diluted solution was extracted with ethyl acetate. The extract was washed with dil. hydrochloric acid, a saturated aqueous solution of sodium bicarbonate and a saturated aqueous solution of sodium chloride, successively, dried over anhydrous magnesium sulphate and then concentrated under reduced pressure. The residue was purified by column chromatography on silica gel (hexane:ethyl acetate=4:1) to give the title compound (250 mg) having the following physical data:

TLC: Rf 0.41 (cyclohexane:ethyl acetate=4:1);

NMR: δ7.4–7.1 (10H, m), 5.6–5.4 (2H, m), 5.4–5.2 (2H, m), 5.08 (2H, s), 4.4–4.0 (2H, m), 3.64 (3H, s), 3.3–2.9 (2H, m), 1.17 (3H, s), 1.0 (3H, s);

IR: ν3300, 2920, 1730–1690, 1650, 1530, 1250, 750, 690 cm$^{-1}$;

MS: m/e 560(M+), 529, 469, 453, 425;

Appearance: yellow oily.

EXAMPLE 5 (ii)

Synthesis of
9α,11α-dimethylmethano-13-aza-14-oxo-15β-benzyloxycarbonylamino-16-phenyl-17,18,19,20-tetranor-11a-carbathromb-5Z-enoic acid

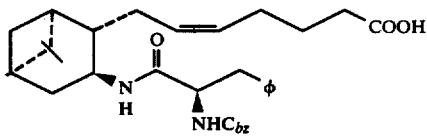

A mixture of the amide (245 mg) prepared in example 5 (i), a 2N aqueous solution of sodium hydroxide (1.2 ml) and methanol (4 ml) was stirred for 16 hrs at room temperature, and then concentrated. The concentrate was diluted with water, the diluted solution was adjusted to pH 3 with an aqueous solution of oxalic acid, and extracted with ethyl acetate. The extract was washed with water and a saturated aqueous solution of sodium chloride, dried over anhydrous magnesium sulphate, and then concentrated. The residue was purified by column chromatography (hexane:ethyl acetate=2:1) to give the title compound (175 mg) having the following physical data:

TLC: Rf 0.52 (chloroform:methanol=10:1);

Appearance: colorless wax.

EXAMPLE 5 (iii)

Synthesis of
9α,11α-dimethylmethano-13-aza-14-oxo-15β-amino-16-phenyl-17,18,19,20-tetranor-11a-carbathromb-5Z-enoic acid

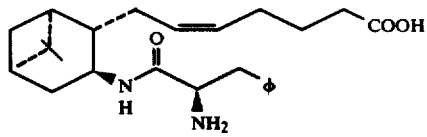

In an atmosphere of argon, a mixture (1.5 ml) of hydrobromic acid - acetic acid (3:7) was added to the compound (165 mg; 0.30 mmol) prepared in example 5 (ii), and the mixture was stirred for 30 min. at 0° C. The mixture was diluted with ice-water. The extract diluted with ethyl acetate was washed with water and a saturated aqueous solution of sodium chloride, successively, dried over anhydrous magnesium sulphate, and then concentrated under reduced pressure. The residue obtained was purified by column chromatography on silica gel (chloroform:methanol=98:2) to give the title compound (66 mg) having the following physical data:

TLC: Rf 0.14 (chloroform:methanol=10:1);

NMR: δ7.4–7.1 (5H, m), 6.4–6.2 (1H, m), 5.6–5.2 (2H, m), 4.4–4 (1H, m) 3.9–3.7 (1H, m), 3.2–2.8 (2H, m), 1.20 (3H, s), 1.03 (3H, s);

IR (KBr tablet method): ν3300, 2920, 2700, 1660, 1530, 1390, 750, 690 cm$^{-1}$;

MS: m/e 412(M+), 395, 321;

Appearance: colorless wax.

EXAMPLE 6

Synthesis of
9α,11α-dimethylmethano-13-aza-14-oxo-20-nor-11a-carbathromb-5Z-enoic acid

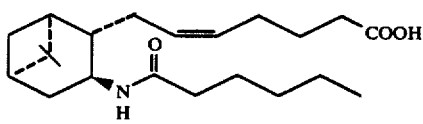

In an atmosphere of argon, 4-carboxybutyl triphenyl phosphonium bromide (31.5g) and potassium t-butoxide (14.35 g) were added into toluene (320 ml), the mixture was stirred for 40 min. at 80° C. To the solution cooled to 20° C., a solution of the aldehyde (10 g) prepared in reference example 17 in toluene was added all at once, and the mixture was allowed to stand for 30 min. After reaction, a 1N aqueous solution of sodium hydroxide was added to the mixture and the mixture was stirred. The aqueous layer separated was washed with diethyl ether, and aqueous solution was adjusted to pH 3 with 2N hydrochloric acid. The solution was extracted with ethyl acetate. The extract was washed with water and a saturated aqueous solution of sodium chloride, successively, dried over anhydrous magnesium sulphate and then concentrated under reduced pressure. The residue was purified by column chromatography on silica gel (hexane:ethyl acetate=3:2) to give the title compound (8.9 g) having the following physical data:

TLC: Rf 0.28 (hexane:ethyl acetate=1:2);

NMR: δ5.6–5.2 (3H, m), 4.4–4.1 (1H, m), 1.22 (3H, s), 1.06 (3H, s);

IR: ν3270, 2870, 2600, 1700, 1610, 1535, 1230 cm$^{-1}$;

MS: m/e 363(M+), 294;

Appearance: colorless oily.

EXAMPLE 6 (a)

Synthesis of
9α,11α-dimethylmethano-13-aza-14-oxo-15αβ-hydroxy-15-cyclopentyl-16,17,18,19,20-pentanor-11a-carbathromb-5Z-enoic acid

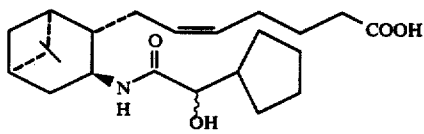

In an atmosphere of argon, a mixture of 4-carboxybutyl triphenyl phosphonium bromide (92 g), potasium t-butoxide (42 g) and toluene (900 ml) was stirred for 50 min. at from 70° C. to 80° C. To the solution cooled to 20° C., a solution of the aldehyde (41 g) prepared in reference example 21 in toluene was added all at once and the mixture was allowed to stand for 30 min. To the reaction mixture, 1 l of a 0.5N aqueous solution of sodium hydroxide, and the mixture was stirred for 2 hrs at from 50° C. to 60° C. The organic layer separated was adjusted to pH 3 with 2N hydrochloric acid and then extracted with ethyl acetate. The extract was washed with water and a saturated aqueous solution of sodium chloride, successively, dried over anhydrous magnesium sulphate and then concentrated under reduced pressure to give the crude title compound (38 g) having the following physical data:

TLC: Rf 0.39 & 0.43 (chloroform:tetrahydrofuran:ethyl acetate=20:2:1).

EXAMPLE 7

Separation of more polar isomer and less polar isomer of
9α,11α-dimethylemethano-13-aza-14-oxo-15αβ-hydroxy-15-cyclopentyl-16,17,18,19,20-pentanor-11a-carbathromb-5Z-enoic acid The compound (38 g) prepared in example 6 (a) was dissolved in ethyl acetate, a solution of diazomethane in ether was dropped to the solution till generation of bubbles was ceased. The solution was concentrated under reduced pressure. The residue was separated by column chromatography on silica gel (hexane-ethyl acetate) to give methyl ester of less polar isomer (11.6 g) and methyl ester of more polar isomer (14.0 g). Each of them was treated in a mixture of a 2N aqueous solution of sodium hydroxide and methanol for 2.5 hrs at 40° C. Each of the solution was concentrated and each of the concentrates was diluted with water. Each of the diluted solutions was adjusted to pH 3 with 2N hydrochloric acid and then extracted with ethyl acetate. Each of the extracts was washed with water, and a saturated aqueous solution of sodium chloride, successively, dried over anhydrous magnesium sulphate and then concentrated under reduced pressure. Each of the residues was purified by column chromatography on silica gel (methylene chloride-methanol) to give the two title compounds having the following physical data:

(a) more polar isomer (15β-hydroxy compound)
Yield: 8.4 g;

TLC: Rf 0.39 (chloroform:tetrahydrofuran:acetic acid=20:2:1);

NMR: δ6.6–6.4 (1H, m), 5.5–5.2 (2H, m), 4.4–4.1 (1H, m), 4.07 (1H, d), 1.22 (3H, s), 1.06 (3H, s);

IR: ν3400–2900, 1700, 1620, 1520, 1230 cm$^{-1}$;

MS: m/e 391(M+), 373, 322;

Appearance: colorless oily.

(b) less polar isomer (15α-hydroxy compound)
Yield: 5.5 g;

TLC: Rf 0.43 (chloroform:tetrahydrofuran:acetic acid=20:2:1);

NMR: δ6.8–6.5 (1H, m), 5.6–5.2 (2H, m) 4.4–4.0 (2H, m), 4.16 (1H, d), 1.23 (3H, s), 1.06 (3H, s);

MS: m/e 391(M+), 373, 322;

Appearance: colorless oily.

EXAMPLE 8

Synthesis of sodium salt of 9α,11α-dimethylmethano-13-aza-14-oxo-20-nor-11a-carbathromb-5Z-enoic acid

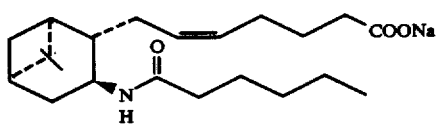

The compound (1.71 g) prepared in example 6 was dissolved into a 1N aqueous solution of sodium hydroxide (4.8 ml) with heating. The solution was filtered off and the filtrate was concentrated under reduced pressure. The residue was evaporated azeotropically with ethanol and the solution was concentrated to dryness. The solid obtained was suspended into acetone (50 ml). The solids suspended were gathered by filtration, dried to give the title compound (1.60 g) having the following physical data:

mp: 130°–140° C.;

NMR (methanol-d₄ solution): δ5.5–5.2 (2H, m), 4.3–4.1 (1H, m), 1.22 (3H, s), 1.08 (3H, s), 1.0–0.8 (3H, m);

IR (KBr tablet method): ν3280, 2910, 2855, 1630, 1550, 1410 cm⁻¹;

Appearance: white powder.

EXAMPLE 8 (a)

Synthesis of sodium salt of 9α,11α-dimethylmethano-13-aza-14-oxo-15β-hydroxy-15-cyclopentyl-16,17,18,19,20-pentanor-11a-carbathromb-5Z-enoic acid

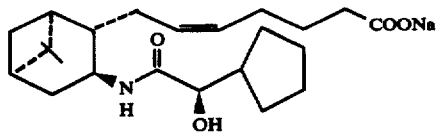

By the same procedure as described in example 8, with using the more polar compound (1.43 g) prepared in example 7 (a), the title compound (1.16 g) having the following physical data was given. With the proviso that, instead of acetone, diethyl ether was used at suspending.

mp: 110°–120° C.;

NMR (methanol-d₄ solution): δ5.5–5.2 (2H, m), 4.4–4.2 (1H, m), 3.92 (1H, d), 1.24 (3H, s), 1.10 (3H, s);

IR (KBr tablet method): ν3400–3300, 2930, 2855, 1640, 1560, 1400 cm⁻¹;

Appearance: white powder.

EXAMPLE 8 (b)

Synthesis of sodium salt of 9α,11α-dimethylmethano-13-aza-14-oxo-15β-hydroxy-16-phenyl-17,18,19,20-tetranor-11a-carbathromb-5Z-enoic acid

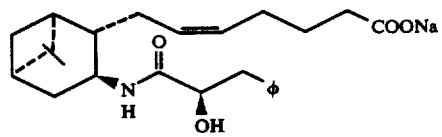

By the same procedure as described in example 8, with using the compound (520 mg) prepared in example 3 (a), the title compound (525 mg) having hhe following physical data was given:

NMR (methanol-d₄ solution): δ7.3–7.1 (5H, m), 6.3–6.1 (1H, m), 5.4–5.2 (2H, m), 4.3–4.15 (1H, m), 4.15–4.0 (1H, m), 1.13 (3H, s), 0.94 (3H, s);

IR: ν3400, 2910, 1640, 1560, 1400, 1085, 695 cm⁻¹;

Appearance: white solid.

EXAMPLE 9

Synthesis of N-methyl-D-glucamine salt of 9α,11α-dimethylmethano-13-aza-14-oxo-20-nor-11a-carbathromb-5Z-enoic acid

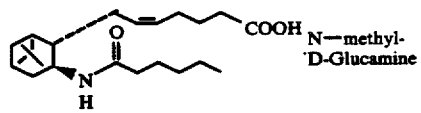

The compound (145 mg) prepared in example 6 and N-methyl-D-glucamine (55 mg) were dissolved into distilled water (0.6 ml). After stirring well, the solution was concentrated and dried in vacuo to give the title compound (141 mg) having the following physical data:

NMR (methanol-d₄ solution): δ5.5–5.2 (2H, m), 4.4–4.1 (1H, m), 4.1–3.9 (1H, m), 3.1 (2H, d), 2.66 (3H, s), 1.22 (3H, s), 1.08 (3H, s), 1.00–0.80 (3H, m);

IR (KBr tablet method): ν3400–3250, 2910, 1630, 1540, 1390, 1070 cm⁻¹;

Appearance: colorless wax.

EXAMPLE 9 (a)

Synthesis of N-methyl-D-glucamine salt of 9α,11α-dimethyl-methano-13-aza-14-oxo-15β-hydroxy-15-cyclopentyl-16,17,18,19,20-pentanor-11a-carbathromb-5Z-enoic acid

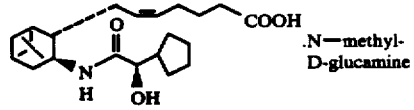

By the same procedure as described in example 9, with using the more polar compound (142 mg) prepared in example 7 (a), the title compound (133 mg) having the following physical data was given:

NMR (methanol-d₄ solution): δ5.5–5.2 (2H, m), 4.4–4.1 (1H, m), 4.1–3.9 (1H, m), 3.91 (1H, d), 3.1 (2H, d), 2.66 (3H, s), 1.23 (3H, s), 1.09 (3H, s);

IR (KBr tablet method): ν3350, 2920, 2855, 1630, 1550, 1490, 1070 cm⁻¹;

Appearance: colorless wax.

EXAMPLE 10

Preparation of Tablets

The following compounds were admixed in conventional manner and were made granules by freeze-drying. To the obtained granules, 100 mg of magnesium stearate (lubricator) was added, and the mixture was mixed and punched out in conventional manner to give 100 tablets each containing 100 mg of active ingredient.

| | |
|---|---|
| 9α,11α-dimethylmethano-13-aza-14-oxo-15β-hydroxy-15-cyclopentyl-16,17,18,19,20-pentanor-11a-carbathromb-5Z—enoic acid (abbreviated as compound A hereafter) | 10 g |
| L-arginine (assistant for dissolving) | 5.2 g |
| Lactose | 10 g |
| Microcrystalline cellulose | 4.7 g |

(they were previously dissolved, in 200 ml of water)

EXAMPLE 11

Preparation for Injection

Sufficient distilled water was added to a mixture of the following compounds to give 500 ml of solution. The solution was sterilized by bacteria-retaining filter, and placed into 5 ml portions in 20 ml ampules in conventional manner. The solution in each ampules was dried by freezing to give 1000 ampules for injection each containing 50 mg of the active ingredient.

| | |
|---|---|
| Compound A | 5 g |
| L-arginine (assistant for dissolving) | 2.6 g |
| mannitol | 50 g |

What is claimed is:

1. A novel 13-aza-14-oxo-TXA$_2$ analogue of general formula:

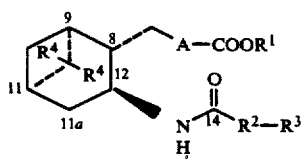

(III)

wherein
symbol A represents
(i) a group of general formula: —CH$_2$CH$_2$—(CH$_2$.)$_m$—.
(ii) a group of general formula: cis—CH═CH—(CH$_2$)$_m$—,
(iii) a group of general formula: —CH$_2$O—(CH$_2$)$_m$—,
(iv) a group of general formula: —S—(CH$_2$)$_m$— (wherein m represents an integer of from 1 to 6) or
(v) a group of general formula:

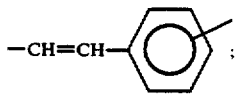

R$^1$ represents a hydrogen atom or a straight or branched alkyl group of from 1 to 12 carbon atom(s);
R$^2$ represents a bond or a straight or branched alkylene or alkenylene group of from 1 to 10 carbon atom(s) unsubstituted or substituted by at least one of hydroxy group, amino group, halogen atom or phenylthio group;
R$^3$ represents
  (i) a phenyl, phenoxy or phenylthio group unsubstituted or substituted by at least one of straight or branched alkyl or alkoxy group of from 1 to 6 carbon atom(s), halogen atom or hydroxy group,
  (ii) a straight or branched alkyl, alkenyl or alkynyl group of from 1 to 6 carbon atom(s) unsubstituted or substituted by at least one of hydroxy group,
  (iii) a cycloalkyl, cycloalkyloxy or cycloalkylthio group of from 4 to 7 carbon atoms unsubstituted or substituted by at least one of straight or branched alkyl group of from 1 to 6 carbon atom(s), halogen atom or hydroxy group,
  (iv) a naphthyl, indolyl or indanyl group; and
R$^4$ represents a hydrogen atom or a methyl group;
with proviso that R$^2$ represents said alkylene or alkeneylene group of from 1 to 10 carbon atom(s) wherein the carbon atom neighboured with R$^3$ in R$^2$ has no substituents, where R$^3$ represents a phenoxy, phenylthio, cycloalkyloxy or cycloalkylthio group unsubstituted or substituted;
and cyclodextrin clathrates thereof and non-toxic salts thereof wherein R$^1$ represents a hydrogen atom.

2. A compound according to claim 1, wherein symbol A is (i) a group of general formula: —CH$_2$CH$_2$—(CH$_2$.)$_m$— or (ii) a group of general formula: cis—CH═CH—(CH$_2$)$_m$— (wherein m is as the same meaning in claim 1).

3. A compound according to claim 1, wherein R$^4$ is a methyl group.

4. A compound according to claim 1, wherein R$^2$ is a bond or a straight or branched alkylene or alkenylene group of from 1 to 10 carbon atom(s).

5. A compound according to claim 2, wherein R$^3$ is a phenyl, phenoxy or phenylthio group unsubstituted or substituted by at least one of straight or branched alkyl or alkoxy group of from 1 to 6 carbon atom(s) or halogen atom or hydroxy group.

6. A compound according to claim 5, which is 9α,1-1α-dimethylmethano-13-aza-14-oxo-16-(4-methoxyphenyl)-17,18,19,20-tetranor-11a-carbathromb-5Z-enoic acid or non-toxic salts thereof.

7. A compound according to claim 5, which is 9α,1-1α-dimethylmethano-13-aza-14-oxo-16-phenyl-17,18,19,20-tetranor-11a-carbathromb-5Z-enoic acid or non-toxic salts thereof.

8. A compound according to claim 5, which is 9α,1-1α-dimethylmethano-13-aza-14-oxo-17-phenyl-18,19,20-trinor-11a-carbathromb-5Z-enoic acid or non-toxic salts thereof.

9. A compound according to claim 5, which is 9α,1-1α-dimethylmethano-13-aza-14-oxo-16-(4-butylphenyl)-17,18,19,20-tetranor-11a-carbathromb-5Z-enoic acid or non-toxic salts thereof.

10. A compound according to claim 5, which is 9α,1-1α-dimethylmethano-13-aza-14-oxo-15-methyl-16-phenyl-17,18,19,20-tetranor-11a-carbathromb-5Z-enoic acid or non-toxic salts thereof.

11. A compound according to claim 5, which is 9α,1-1α-dimethylmethano-13-aza-14-oxo-15,15-dimethyl-16- phenyl-17,18,19,20-tetranor-11a-carbathromb-5Z-enoic acid or non-toxic salts thereof.

12. A compound according to claim 5, which is 9α,1-1α-dimethylmethano-13-aza-14-oxo-18-phenyl-19,20-dinor-11a-carbathromb-5Z-enoic acid or non-toxic salts thereof.

13. A compound according to claim 5, which is 9α,1-1α-dimethylmethano-13-aza-14-oxo-15,15-dimethyl-17-phenyl-18,19,20-trinor-11a-carbathromb-5Z-enoic acid or non-toxic salts thereof.

14. A compound according to claim 5, which is 9α,1-1α-dimethylmethano-13-aza-14-oxo-15,15-dimethyl-18-phenyl-19,20-dinor-11a-carbathromb-5Z-enoic acid or non-toxic salts thereof.

15. A compound according to claim 5, which is 9α,1-1α-dimethylmethano-13-aza-14-oxo-15,15-dimethyl-19-phenyl-20-nor-11a-carbathromb-5Z-enoic acid or non-toxic salts thereof.

16. A compound according to claim 5, which is 9α,1-1α-dimethylmethano-13-aza-14-oxo-15αβ-methyl-16-phenyl-17,18,19,20-tetranor-11a-carbathromb-5Z-enoic acid or non-toxic salts thereof.

17. A compound according to claim 5, which is 9α,1-1α-dimethylmethano-13-aza-14-oxo-15αβ-methyl-16-(4-methyl phenyl)-17,18,19,20-tetranor-11a-carbathromb-5Z-enoic acid or non-toxic salts thereof.

18. A compound according to claim 5, which is 9α,1-1α-dimethylmethano-13-aza-14-oxo-15-phenoxy-16,17,18,19,20-pentanor-11a-carbathromb-5Z-enoic acid or non-toxic salts thereof.

19. A compound according to claim 5, which is 9α,1-1α-dimethylmethano-13-aza-14-oxo-15-phenylthio-16,17,18,19,20-pentanor-11a-carbathromb-5Z-enoic acid or non-toxic salts thereof.

20. A compound according to claim 5, which is 9α,1-1α-dimethylmethano-13-aza-14-oxo-16-(4-methylphenyl)-17,18,19,20-tetranor-11a-carbathromb-5Z-enoic acid or non-toxic salts thereof.

21. A compound according to claim 5, which is 9α,1-1α-dimethylmethano-13-aza-14-oxo-16,16-dimethyl-17-phenyl-18,19,20-trinor-11a-carbathromb-5Z-enoic acid or non-toxic salts thereof.

22. A compound according to claim 5, which is 9α,1-1α-dimethylmethano-13-aza-14-oxo-17-(3-chlorophenyl)-18,19,20-trinor-11a-carbathromb-5Z-enoic acid or non-toxic salts thereof.

23. A compound according to claim 5, which is 9α,1-1α-dimethylmethano-13-aza-14-oxo-17-(3-chlorophenyl)-18,19,20-trinor-11a-carbathromb-5Z,16E-dienoic acid or non-toxic salts thereof.

24. A compound according to claim 5, which is 9α,11α-dimethylmethano-13-aza-14-oxo-16αβ-methyl-17-phenyl-18,19,20-trinor-11a-carbathromb-5Z-enoic acid or non-toxic salts thereof.

25. A compound according to claim 5, which is 9α,1-1α-dimethylmethano-13-aza-14-oxo-16-phenylthio-17,18,19,20-tetranor-11a-carbathromb-5Z-enoic acid or non-toxic salts thereof.

26. A compound according to claim 5, which is 9α,1-1α-dimethylmethano-13-aza-14-oxo-16αβ-methyl-18-phenyl-19,20-dinor-11a-carbathromb-5Z-enoic acid or non-toxic salts thereof.

27. A compound according to claim 1, wherein $R^3$ is a straight or branched alkyl, alkenyl or alkynyl group of from 1 to 6 carbon atom(s) unsubstituted or substituted by at least one of hydroxy group.

28. A compound according to claim 27, which is 9α,11α-dimethylmethano-13-aza-14-oxo-15,15-dimethyl-20-nor-11a-carbathromb-5Z-en-17-ynoic acid or non-toxic salts thereof.

29. A compound according to claim 27, which is 9α,11α-dimethylmethano-13-aza-14-oxo-15,15-dimethyl-20-nor-11a-carbathromb-5Z-enoic acid or non-toxic salts thereof.

30. A compound according to claim 27, which is 9α,11α-dimethylmethano-13-aza-14-oxo-11a-carbathromb-5Z-enoic acid or non-toxic salts thereof.

31. A compound according to claim 27, which is 9α,11α-dimethylmethano-13-aza-14-oxo-16αβ,20,20-trimethyl-11a-carbathromb-5Z,19-dienoic acid or non-toxic salts thereof.

32. A compound according to claim 27, which is 9α,11α-dimethylmethano-13-aza-14-oxo-18,19,20-trinor-11a-carbathromb-5Z-enoic acid or non-toxic salts thereof.

33. A compound according to claim 27, which is 9α,11α-dimethylmethano-13-aza-14-oxo-19,20-dinor-11a-carbathromb-5Z-enoic acid or non-toxic salts thereof.

34. A compound according to claim 27, which is 9α,11α-dimethylmethano-13-aza-14-oxo-20-nor-11a-carbathromb-5Z-enoic acid or non-toxic salts thereof.

35. A compound according to claim 27, which is 9α,11α-dimethylmethano-13-aza-14-oxo-16,17,18,19,20-pentanor-11a-carbathromb-5Z-enoic acid or non-toxic salts thereof.

36. A compound according to claim 27, which is 9α,11α-dimethylmethano-13-aza-14-oxo-16αβ-methyl19,20-dinor-11a-carbathromb-5Z-enoic acid or non-toxic salts thereof.

37. A compound according to claim 27, which is 9α,11α-dimethylmethano-13-aza-14-oxo-16-methyl-18,19,20-trinor-11a-carbathromb-5Z-enoic acid or non-toxic salts thereof.

38. A compound according to claim 27, which is 9α,11α-dimethylmethano-13-aza-14-oxo-17-methyl-19,20-dinor-11a-carbathromb-5Z-enoic acid or non-toxic salts thereof.

39. A compound according to claim 27, which is 9α,11α-dimethylmethano-13-aza-14-oxo-17αβ-methyl-20-nor-11a-carbathromb-5Z-enoic acid or non-toxic salts thereof.

40. A compound according to claim 27, which is 9α,11α-dimethylmethano-13-aza-14-oxo-16αβ-methyl-20-nor-11a-carbathromb-5Z-enoic acid or non-toxic salts thereof.

41. A compound according to claim 27, which is 9α,11α-dimethylmethano-13-aza-14-oxo-18-methyl-20-nor-11a-carbathromb-5Z-enoic acid or non-toxic salts thereof.

42. A compound according to claim 27, which is 9α,11α-dimethylmethano-13-aza-14-oxo-16,18-dimethyl-20-nor-11a-carbathromb-5Z-enoic acid or non-toxic salts thereof.

43. A compound according to claim 1, wherein $R^3$ is a cycloalkyl, cycloalkyloxy or cycloalkylthio group of from 4 to 7 carbon atoms unsubstituted or substituted by at least one of straight or branched alkyl group of from 1 to 6 carbon atom(s), halogen atom or hydroxy group.

44. A compound according to claim 43, which is 9α,11α-dimethylmethano-13-aza-14-oxo-15,15-dimethyl-16-(3S-butylcyclopentyl)-17,18,19,20-tetranor-11a-carbathromb-5Z-enoic acid or non-toxic salts thereof.

45. A compound according to claim 43, which is 9α,11α-dimethylmethano-13-aza-14-oxo-15-cyclopentyl-16,17,18,19,20-pentanor-11a-carbathromb-5Z-enoic acid or non-toxic salts thereof.

46. A compound according to claim 43, which is 9α,11α-dimethylmethano-13-aza-14-oxo-16-cyclohexyl-17,18,19,20-tetranor-11a-carbathromb-5Z-enoic acid or non-toxic salts thereof.

47. A compound according to claim 43, which is 9α,11α-dimethylmethano-13-aza-14-oxo-16-cyclopentyl-17,18,19,20-tetranor-11a-carbathromb-5Z-enoic acid or non-toxic salts thereof.

48. A compound according to claim 43, which is 9α,11α-dimethylmethano-13-aza-14-oxo-14-(3S-butylcyclopentyl)-15,16,17,18,19,20-hexanor-11a-carbathromb-5Z-enoic acid or non-toxic salts thereof.

49. A compound according to claim 43, which is 9α,11α-dimethylmethano-13-aza-14-oxo-17-cyclohexyl-18,19,20-trinor-11a-carbathromb-5Z-enoic acid or non-toxic salts thereof.

50. A compound according to claim 43, which is 9α,11α-dimethylmethano-13-aza-14-oxo-14-cyclopentyl-15,16,17,18,19,20-hexanor-11a-carbathromb-5Z-enoic acid or non-toxic salts thereof.

51. A compound according to claim 43, which is 9α,11α-dimethylmethano-13-aza-14-oxo-15-cyclopentylthio-16,17,18,19,20-pentanor-11a-carbathromb-5Z-enoic acid or non-toxic salts thereof.

52. A compound according to claim 43, which is 9α,11α-dimethylmethano-13-aza-14-oxo-17-cyclopentyl-18,19,20-trinor-11a-carbathromb-5Z-enoic acid or non-toxic salts thereof.

53. A compound according to claim 43, which is 9α,11α-dimethylmethano-13-aza-14-oxo-16-cyclopentylthio-17,18,19,20-tetranor-11a-carbathromb-5Z-enoic acid or non-toxic salts thereof.

54. A compound according to claim 43, which is 9α,11α-dimethylmethano-13-aza-14-oxo-17-cyclopentylthio-18,19,20-trinor-11a-carbathromb-5Z-enoic acid or non-toxic salts thereof.

55. A compound according to claim 43, which is 9α,11α-dimethylmethano-13-aza-14-oxo-14-(1-hydroxycyclopentyl)-15,16,17,18,19,20-hexanor-11a-carbathromb-5Z-enoic acid or non-toxic salts thereof.

56. A compound according to claim 43, which is 9α,11α-dimethylmethano-13-aza-14-oxo-16αβ-methyl-16-cyclopentyl-17,18,19,20-tetranor-11a-carbathromb-5Z-enoic acid or non-toxic salts thereof.

57. A compound according to claim 43, which is 9α,11α-dimethylmethano-13-aza-14-oxo-16αβ-methyl-17-cyclopentyl-18,19,20-trinor-11a-carbathromb-5Z-enoic acid or non-toxic salts thereof.

58. A compound according to claim 43, which is 9α,11α-dimethylmethano-13-aza-14-oxo-17αβ-methyl-17-cyclopentyl-18,19,20-trinor-11a-carbathromb-5Z-enoic acid or non-toxic salts thereof.

59. A compound according to claim 1, wherein $R^3$ is a naphthyl, indolyl or indanyl group.

60. A compound according to claim 59, which is 9α,11α-dimethylmethano-13-aza-14-oxo-15-(2-naphthyl)-16,17,18,19,20-pentanor-11a-carbathromb-5Z-enoic acid or non-toxic salts thereof.

61. A compound according to claim 59, which is 9α,11α-dimethylmethano-13-aza-14-oxo-17-(3-indolyl)-18,19,20-trinor-11a-carbathromb-5Z-enoic acid or non-toxic salts thereof.

62. A compound according to claim 59, which is 9α,11α-dimethylmethano-13-aza-14-oxo-15-(2-indanyl)-16,17,18,19,20 -pentanor-11a-carbathromb-5Z-enoic acid or non-toxic salts thereof.

63. A compound according to claim 1, wherein $R^2$ is a straight or branched alkylene or alkenylene group of from 1 to 10 carbon atom(s) unsubstituted or substituted by at least one of hydroxy group, amino group, halogen atom or phenylthio group.

64. A compound according to claim 63, wherein $R^3$ is a phenyl group unsubstituted or substituted by at least one of straight or branched alkyl or alkoxy group of from 1 to 6 carbon atom(s), halogen atom or hydroxy group.

65. A compound according to claim 64, which is 9α,11α-dimethylmethano-13-aza-14-oxo-15β-hydroxy-16-phenyl-17,18,19,20-tetranor-11a-carbathromb-5Z-enoic acid or non-toxic salts thereof.

66. A compound according to claim 64, which is 9α,11α-dimethylmethano-13-aza-14-oxo-15β-amino-16-phenyl-17,18,19,20-tetranor-11a-carbathromb-5Z-enoic acid or non-toxic salts thereof.

67. A compound according to claim 64, which is 9α,11α-dimethylmethano-13-aza-14-oxo-15α-hydroxy-16-phenyl- 17,18,19,20-tetranor-11a-carbathromb-5Z-enoic acid or non-toxic salts thereof.

68. A compound according to claim 64, which is 9α,11α-dimethylmethano-13-aza-14-oxo-15αβ-hydroxy-17-(4-propylphenyl)-18,19,20-trinor-11a-carbathromb-5Z-enoic acid or non-toxic salts thereof.

69. A compound according to claim 64, which is 9α,11α-dimethylmethano-13-aza-14-oxo-15αβ-hydroxy-17-phenyl-18,19,20-trinor-11a-carbathromb-5Z-enoic acid or non-toxic salts thereof.

70. A compound according to claim 64, which is 9α,11α-dimethylmethano-13-aza-14-oxo-15α-hydroxy-16-phenyl-17,18,19,20-tetranor-11a-carbathromb-5Z-enoic acid methyl ester.

71. A compound according to claim 63, wherein $R^3$ is a straight or branched alkyl, alkenyl or alkynyl group of from 1 to 6 carbon atom(s) unsubstituted or substituted by at least one of hydroxy group.

72. A compound according to claim 71, which is 9α,11α-dimethylmethano-13-aza-14-oxo-15αβ-hydroxy-11a-carbathromb-5Z-enoic acid or non-toxic salts thereof.

73. A compound according to claim 71, which is 9α,11α-dimethylmethano-13-aza-14-oxo-15αβ-hydroxy-17-methyl-20-nor-11a-carbathromb-5Z-enoic acid or non-toxic salts thereof.

74. A compound according to claim 71, which is 9α,11α-dimethylmethano-13-aza-14-oxo-15αβ-hydroxy-17-methyl- 19,20-dinor-11a-carbathromb-5Z-enoic acid or non-toxic salts thereof.

75. A compound according to claim 71, which is 9α,11α-dimethylmethano-13-aza-14-oxo-15α-hydroxy-16-methyl-18,19,20-trinor-11a-carbathromb-5Z-enoic acid or non-toxic salts thereof.

76. A compound according to claim 71, which is 9α,11α-dimethylmethano-13-aza-14-oxo-15β-hydroxy-16-methyl-18,19,20-trinor-11a-carbathromb-5Z-enoic acid of non-toxic salts thereof.

77. A compound according to claim 71, which is 9α,11α-dimethylmethano-13-aza-14-oxo-15αβ-hydroxy-18,19,20-trinor-11a-carbathromb-5Z-enoic acid or non-toxic salts thereof.

78. A compound according to claim 63, wherein $R^3$ is a cycloalkyl group of from 4 to 7 carbon atoms unsubstituted or substituted by at least one of straight or branched alkyl group of from 1 to 6 carbon atom(s), halogen atom or hydroxy group.

79. A compound according to claim 78, which is 9α,11α-dimethylmethano-13-aza-14-oxo-15αβ-chloro-15-cyclopentyl-16,17,18,19,20-pentanor-11a-carbathromb-5Z-enoic acid or non-toxic salts thereof.

80. A compound according to claim 78, which is 9α,11α-dimethylmethano-13-aza-14-oxo-15αβ-chloro-16-cyclopentyl-17,18,19,20-tetranor-11a-carbathromb-5Z-enoic acid or non-toxic salts thereof.

81. A compound according to claim 78, which is 9α,11α-dimethylmethano-13-aza-14-oxo-15α-hydroxy-15-cyclopentyl-16,17,18,19,20-pentanor-11a-carbathromb-5Z-enoic acid or non-toxic salts thereof.

82. A compound according to claim 78, which is 9α,11α-dimethylmethano-13-aza-14-oxo-15β-hydroxy-15-cyclopentyl-16,17,18,19,20-pentanor-11a-carbathromb-5Z-enoic acid or non-toxic salts thereof.

83. A compound according to claim 78, which is 9α,11α-dimethylmethano-13-aza-14-oxo-16αβ-phenylthio-17-cyclopentyl-18,19,20-trinor-11a-carbathromb-b 5Z-enoic acid or non-toxic salts thereof.

84. A compound according to claim 1, wherein non-toxic salt is a N-methylglucamine salt.

85. A compound according to claim 1, wherein non-toxic salt is a sodium salt.

86. A pharmaceutical composition for the prevention and/or treatment of hypertension, thrombus, cerebral apoplexy, asthma, cardiac infarction, angina pectoris, cerebral infarction, or acute cardiac diseases, which comprises, as active ingredient, an effective amount of at least one compound of the general formula (III) depicted in claim 1, wherein various symbols are as defined in claim 1, or a cyclodextrin clathrate thereof, or, when $R^1$ represents a hydrogen atom, a non-toxic salt thereof, together with a pharmaceutical carrier or coating.

87. A method for the prevention and/or treatment of hypertension, thrombus, cerebral apoplexy, asthma, cardiac infarction, angina pectoris, cerebral infarction, or acute cardiac diseases, which comprises the oral, rectal, or parenteral administration of an effective amount of a compound as claimed in claim 1, a cyclodextrin clathrate thereof, or, when $R^1$ in formula (III) depicted in claim 1 represents a hydrogen atom, a non-toxic salt thereof.

* * * * *